US011116407B2

(12) United States Patent
Dickie et al.

(10) Patent No.: US 11,116,407 B2
(45) Date of Patent: Sep. 14, 2021

(54) ANATOMICAL SURFACE ASSESSMENT METHODS, DEVICES AND SYSTEMS

(71) Applicant: ARANZ Healthcare Limited, Christchurch (NZ)

(72) Inventors: Oliver John Dickie, Wellington (NZ); Philip John Barclay, Christchurch (NZ); Brent Stephen Robinson, Christchurch (NZ); Russell William Watson, Christchurch (NZ)

(73) Assignee: ARANZ Healthcare Limited, Christchurch (NZ)

( * ) Notice: Subject to any disclaimer, the term of this patent is extended or adjusted under 35 U.S.C. 154(b) by 0 days.

(21) Appl. No.: 15/816,862

(22) Filed: Nov. 17, 2017

(65) Prior Publication Data

US 2018/0132726 A1 May 17, 2018

Related U.S. Application Data

(60) Provisional application No. 62/423,709, filed on Nov. 17, 2016.

(51) Int. Cl.
*A61B 5/00* (2006.01)
*H04N 5/232* (2006.01)
(Continued)

(52) U.S. Cl.
CPC ............ *A61B 5/0077* (2013.01); *A61B 5/002* (2013.01); *A61B 5/445* (2013.01); *A61B 5/6844* (2013.01);
(Continued)

(58) Field of Classification Search
CPC ..... A61B 5/002; A61B 5/0017; A61B 5/0077; A61B 5/445; A61B 5/6844; A61B 5/6898
See application file for complete search history.

(56) References Cited

U.S. PATENT DOCUMENTS 3,259,612 A 7/1966 Peter
3,335,716 A 8/1967 Alt et al.
(Continued)

FOREIGN PATENT DOCUMENTS

AT 549703 3/2012
CN 110326029 10/2019
(Continued)

OTHER PUBLICATIONS

Afromowitz, et al., "Multispectral Imaging of Burn Wounds: A New Clinical Instrument for Evaluating Burn Depth", IEEE Transactions on Biomedical Engineering, vol. 35, No. 10, pp. 842-850; Oct. 1988.
(Continued)

*Primary Examiner* — Boubacar Abdou Tchoussou
(74) *Attorney, Agent, or Firm* — Perkins Coie LLP

(57) ABSTRACT

A method of assessing a feature on a patient's skin surface includes capturing (i) an image of the patient's skin surface with a camera of a portable capture device and (ii) range information with an auxiliary range measurement device that is attached to the portable capture device. Based on the range information, a single range value can be determined between the capture device and the patient's skin surface. In some embodiments, a scale can be associated with the image based on the single range value.

19 Claims, 20 Drawing Sheets

(51) Int. Cl.
*H04N 5/265* (2006.01)
*G06T 7/00* (2017.01)
*G06T 7/62* (2017.01)
*G06T 7/80* (2017.01)
*H04N 17/00* (2006.01)
*H04N 5/222* (2006.01)
*G01S 17/88* (2006.01)
*G01S 17/86* (2020.01)
*H04Q 9/00* (2006.01)

(52) U.S. Cl.
CPC ............ *A61B 5/6898* (2013.01); *G01S 17/86* (2020.01); *G01S 17/88* (2013.01); *G06T 7/0016* (2013.01); *G06T 7/62* (2017.01); *G06T 7/80* (2017.01); *H04N 5/2226* (2013.01); *H04N 5/23222* (2013.01); *H04N 5/23293* (2013.01); *H04N 5/265* (2013.01); *H04N 17/002* (2013.01); *H04Q 9/00* (2013.01); *A61B 5/444* (2013.01); *A61B 2560/0214* (2013.01); *A61B 2560/0223* (2013.01); *A61B 2562/0233* (2013.01); *A61B 2562/0257* (2013.01); *A61B 2576/02* (2013.01); *G06T 2207/10028* (2013.01); *G06T 2207/30004* (2013.01); *G06T 2207/30088* (2013.01); *H04Q 2209/43* (2013.01)

(56) References Cited

U.S. PATENT DOCUMENTS

| | | |
|---|---|---|
| 4,090,501 A | 5/1978 | Chaitin |
| 4,170,987 A | 10/1979 | Anselmo et al. |
| 4,236,082 A | 11/1980 | Butler |
| 4,505,583 A | 3/1985 | Konomi |
| 4,515,165 A | 5/1985 | Carroll |
| 4,535,782 A | 8/1985 | Zoltan |
| 4,556,057 A | 12/1985 | Hiruma et al. |
| 4,724,480 A | 2/1988 | Hecker et al. |
| 4,736,739 A | 4/1988 | Flaton |
| 4,768,513 A | 9/1988 | Suzuki |
| 4,773,097 A | 9/1988 | Suzaki et al. |
| 4,821,117 A | 4/1989 | Sekiguchi |
| 4,839,807 A | 6/1989 | Doi et al. |
| 4,851,984 A | 7/1989 | Doi et al. |
| 4,894,547 A | 1/1990 | Leffell et al. |
| 4,930,516 A | 6/1990 | Alfano et al. |
| 4,957,114 A | 9/1990 | Zeng et al. |
| 4,979,815 A | 12/1990 | Tsikos |
| 4,996,994 A | 3/1991 | Steinhauer et al. |
| D315,901 S | 4/1991 | Knowles |
| 5,003,977 A | 4/1991 | Suzuki et al. |
| 5,016,173 A | 5/1991 | Kenet et al. |
| 5,036,853 A | 8/1991 | Jeffcoat et al. |
| 5,080,100 A | 1/1992 | Trotel |
| 5,157,461 A | 10/1992 | Page |
| 5,174,297 A | 12/1992 | Daikuzono |
| 5,241,468 A | 8/1993 | Kenet |
| 5,270,168 A | 12/1993 | Grinnell |
| 5,319,550 A | 6/1994 | Griffith |
| 5,363,854 A | 11/1994 | Martens et al. |
| 5,369,496 A | 11/1994 | Alfano et al. |
| 5,396,331 A | 3/1995 | Kitoh et al. |
| 5,408,996 A | 4/1995 | Salb |
| 5,421,337 A | 6/1995 | Richards-Kortum et al. |
| 5,515,449 A | 5/1996 | Tsuruoka et al. |
| 5,519,208 A | 5/1996 | Esparza et al. |
| 5,528,703 A | 6/1996 | Lee |
| 5,531,520 A | 7/1996 | Grimson et al. |
| 5,532,824 A | 7/1996 | Harvey et al. |
| 5,561,526 A | 10/1996 | Huber et al. |
| 5,588,428 A | 12/1996 | Smith et al. |
| 5,590,660 A | 1/1997 | MacAulay et al. |
| 5,603,318 A | 2/1997 | Heilbrun et al. |
| 5,627,907 A | 5/1997 | Gur et al. |
| 5,644,141 A | 7/1997 | Hooker et al. |
| 5,648,915 A | 7/1997 | McKinney et al. |
| 5,673,300 A | 9/1997 | Reckwerdt et al. |
| 5,689,575 A | 11/1997 | Sako et al. |
| 5,699,798 A | 12/1997 | Hochman et al. |
| 5,701,902 A | 12/1997 | Vari et al. |
| 5,717,791 A | 2/1998 | Labaere et al. |
| D393,068 S | 3/1998 | Kodama |
| 5,740,268 A | 4/1998 | Nishikawa et al. |
| 5,749,830 A | 5/1998 | Kaneko et al. |
| 5,784,162 A | 7/1998 | Cabib et al. |
| 5,791,346 A | 8/1998 | Craine et al. |
| 5,799,100 A | 8/1998 | Clarke et al. |
| 5,810,014 A | 9/1998 | Davis et al. |
| 5,836,872 A | 11/1998 | Kenet et al. |
| 5,910,972 A | 6/1999 | Ohkubo et al. |
| 5,921,937 A | 7/1999 | Davis et al. |
| 5,946,645 A | 8/1999 | Rioux et al. |
| 5,957,837 A | 9/1999 | Raab |
| 5,967,797 A | 10/1999 | Maldonado |
| 5,967,979 A | 10/1999 | Taylor et al. |
| 5,969,822 A | 10/1999 | Fright et al. |
| 5,974,165 A | 10/1999 | Giger et al. |
| 6,032,070 A | 2/2000 | Flock et al. |
| 6,081,612 A | 6/2000 | Gutkowicz-Krusin et al. |
| 6,081,739 A | 6/2000 | Lemchen |
| 6,091,995 A | 7/2000 | Ingle et al. |
| 6,101,408 A | 8/2000 | Craine et al. |
| 6,208,749 B1 | 3/2001 | Gutkowicz-Krusin et al. |
| 6,215,893 B1 | 4/2001 | Leshem et al. |
| 6,265,151 B1 | 7/2001 | Canter et al. |
| 6,266,453 B1 | 7/2001 | Hibbard et al. |
| 6,272,278 B1 | 8/2001 | Takahata et al. |
| 6,278,793 B1 | 8/2001 | Gur et al. |
| 6,307,957 B1 | 10/2001 | Gutkowicz-Krusin et al. |
| 6,324,417 B1 | 11/2001 | Cotton |
| D453,350 S | 2/2002 | Fenton |
| 6,359,513 B1 | 3/2002 | Kuo et al. |
| 6,359,612 B1 | 3/2002 | Peter |
| D455,166 S | 4/2002 | Raad |
| 6,381,026 B1 | 4/2002 | Schiff et al. |
| 6,381,488 B1 | 4/2002 | Dickey et al. |
| 6,392,744 B1 | 5/2002 | Holec |
| 6,396,270 B1 | 5/2002 | Smith |
| 6,413,212 B1 | 7/2002 | Raab |
| 6,421,463 B1 | 7/2002 | Poggio et al. |
| 6,427,022 B1 | 7/2002 | Craine et al. |
| 6,491,632 B1 | 12/2002 | Taylor |
| 6,567,682 B1 | 5/2003 | Osterweil et al. |
| 6,594,388 B1 | 7/2003 | Gindele et al. |
| 6,594,516 B1 | 7/2003 | Steckner et al. |
| 6,603,552 B1 | 8/2003 | Cline et al. |
| 6,611,617 B1 | 8/2003 | Crampton |
| 6,611,833 B1 | 8/2003 | Johnson |
| 6,631,286 B2 | 10/2003 | Pfeiffer et al. |
| 6,648,820 B1 | 11/2003 | Sarel |
| 6,671,349 B1 | 12/2003 | Griffith |
| 6,678,001 B1 | 1/2004 | Elberbaum |
| 6,690,964 B2 | 2/2004 | Bieger et al. |
| 6,715,675 B1 | 4/2004 | Rosenfeld |
| 6,754,370 B1 | 6/2004 | Hall-Holt et al. |
| 6,770,186 B2 | 8/2004 | Rosenfeld et al. |
| 6,798,571 B2 | 9/2004 | Wetzel et al. |
| 6,809,803 B1 | 10/2004 | O'Brien et al. |
| 6,810,279 B2 | 10/2004 | Mansfield et al. |
| 6,816,606 B2 | 11/2004 | Wetzel et al. |
| 6,816,847 B1 | 11/2004 | Toyama |
| 6,862,410 B2 | 3/2005 | Miyoshi |
| 6,862,542 B2 | 3/2005 | Lockhart et al. |
| 6,873,340 B2 | 3/2005 | Luby |
| 6,873,716 B1 | 3/2005 | Bowker |
| 6,879,394 B2 | 4/2005 | Amblard et al. |
| 6,907,193 B2 | 6/2005 | Kollias et al. |
| 6,915,073 B2 | 7/2005 | Seo |
| 6,922,523 B2 | 7/2005 | Merola et al. |
| 6,941,323 B1 | 9/2005 | Galperin |
| 6,961,517 B2 | 11/2005 | Merola et al. |
| 6,968,094 B1 | 11/2005 | Gallagher |

(56) References Cited

U.S. PATENT DOCUMENTS

| | | |
|---|---|---|
| 6,993,169 B2 | 1/2006 | Wetzel et al. |
| 7,006,223 B2 | 2/2006 | Mullani |
| 7,013,172 B2 | 3/2006 | Mansfield et al. |
| 7,015,906 B2 | 3/2006 | Olschewski et al. |
| 7,027,153 B2 | 4/2006 | Mullani |
| 7,040,536 B2 | 5/2006 | Rosenfeld |
| 7,054,674 B2 | 5/2006 | Cane et al. |
| 7,064,311 B2 | 6/2006 | Jung et al. |
| 7,068,828 B2 | 6/2006 | Kim et al. |
| 7,068,836 B1 | 6/2006 | Rubbert et al. |
| 7,074,509 B2 | 7/2006 | Rosenfeld et al. |
| 7,103,205 B2 | 9/2006 | Wang et al. |
| 7,106,885 B2 | 9/2006 | Osterweil et al. |
| 7,127,094 B1 | 10/2006 | Elbaum et al. |
| 7,127,280 B2 | 10/2006 | Dauga |
| 7,128,894 B1 | 10/2006 | Tannous et al. |
| 7,130,465 B2 | 10/2006 | Muenzenmayer et al. |
| 7,136,191 B2 | 11/2006 | Kaltenbach et al. |
| D533,555 S | 12/2006 | Odhe et al. |
| 7,155,049 B2 | 12/2006 | Wetzel et al. |
| 7,162,063 B1 | 1/2007 | Craine et al. |
| 7,167,243 B2 | 1/2007 | Mullani |
| 7,167,244 B2 | 1/2007 | Mullani |
| 7,181,363 B2 | 2/2007 | Ratti et al. |
| 7,194,114 B2 | 3/2007 | Schneiderman |
| 7,212,660 B2 | 5/2007 | Wetzel et al. |
| 7,227,621 B2 | 6/2007 | Lee et al. |
| 7,233,693 B2 | 6/2007 | Momma |
| D547,347 S | 7/2007 | Kim |
| 7,248,724 B2 | 7/2007 | Gutenev |
| D554,682 S | 11/2007 | Martinez |
| 7,295,226 B1 | 11/2007 | Meron et al. |
| 7,298,881 B2 | 11/2007 | Giger et al. |
| D561,804 S | 2/2008 | Asai |
| 7,347,365 B2 | 3/2008 | Rowe |
| 7,376,346 B2 | 5/2008 | Merola et al. |
| 7,400,754 B2 | 7/2008 | Jung et al. |
| 7,421,102 B2 | 9/2008 | Wetzel et al. |
| 7,426,319 B2 | 9/2008 | Takahashi |
| 7,440,597 B2 | 10/2008 | Rowe |
| 7,450,783 B2 | 11/2008 | Talapov et al. |
| 7,460,250 B2 | 12/2008 | Keightley et al. |
| 7,474,415 B2 | 1/2009 | Lin et al. |
| 7,487,063 B2 | 2/2009 | Tubic et al. |
| 7,489,799 B2 | 2/2009 | Nilsen et al. |
| 7,495,208 B2 | 2/2009 | Czarnek et al. |
| 7,496,399 B2 | 2/2009 | Maschke |
| 7,509,861 B2 | 3/2009 | Masotti et al. |
| 7,538,869 B2 | 5/2009 | Treado et al. |
| 7,545,963 B2 | 6/2009 | Rowe |
| D597,205 S | 7/2009 | Koch |
| 7,580,590 B2 | 8/2009 | Lin et al. |
| 7,581,191 B2 | 8/2009 | Rice et al. |
| 7,587,618 B2 | 9/2009 | Inui et al. |
| 7,595,878 B2 | 9/2009 | Nelson et al. |
| 7,603,031 B1 | 10/2009 | Viaud et al. |
| D603,441 S | 11/2009 | Wada |
| 7,613,335 B2 | 11/2009 | McLennan et al. |
| 7,620,211 B2 | 11/2009 | Browne et al. |
| 7,647,085 B2 | 1/2010 | Cane et al. |
| 7,668,350 B2 | 2/2010 | Rowe |
| 7,684,589 B2 | 3/2010 | Nilsen et al. |
| 7,724,379 B2 | 5/2010 | Kawasaki et al. |
| 7,729,747 B2 | 6/2010 | Stranc et al. |
| 7,735,729 B2 | 6/2010 | Rowe |
| 7,738,032 B2 | 6/2010 | Kollias et al. |
| 7,751,594 B2 | 7/2010 | Rowe et al. |
| 7,765,487 B2 | 7/2010 | Cable |
| 7,819,311 B2 | 10/2010 | Rowe et al. |
| 7,869,641 B2 | 1/2011 | Wetzel et al. |
| 7,876,948 B2 | 1/2011 | Wetzel et al. |
| 7,881,777 B2 | 2/2011 | Docherty et al. |
| 7,894,645 B2 | 2/2011 | Barsky |
| 7,912,320 B1 | 3/2011 | Minor |
| 7,912,534 B2 | 3/2011 | Grinvald et al. |
| 7,916,834 B2 | 3/2011 | Piorek et al. |
| 7,931,149 B2 | 4/2011 | Gilad et al. |
| 7,951,395 B2 | 5/2011 | Lee et al. |
| 8,000,776 B2 | 8/2011 | Gono |
| 8,019,801 B1 | 9/2011 | Robb et al. |
| 8,026,942 B2 | 9/2011 | Payonk et al. |
| 8,071,242 B2 | 12/2011 | Rosenfeld et al. |
| 8,078,262 B2 | 12/2011 | Murphy et al. |
| 8,094,294 B2 | 1/2012 | Treado et al. |
| 8,105,233 B2 | 1/2012 | Abou El Kheir |
| D653,687 S | 2/2012 | Yu |
| 8,123,704 B2 | 2/2012 | Richards |
| 8,150,500 B2 | 4/2012 | Goldman et al. |
| 8,161,826 B1 | 4/2012 | Taylor |
| 8,165,357 B2 | 4/2012 | Rowe |
| 8,184,873 B2 | 5/2012 | Rowe et al. |
| D662,122 S | 6/2012 | Goodwin |
| D664,655 S | 7/2012 | Daniel et al. |
| 8,213,695 B2 | 7/2012 | Zouridakis |
| 8,218,862 B2 | 7/2012 | Demirli et al. |
| 8,218,873 B2 | 7/2012 | Boncyk et al. |
| 8,218,874 B2 | 7/2012 | Boncyk et al. |
| 8,224,077 B2 | 7/2012 | Boncyk et al. |
| 8,224,078 B2 | 7/2012 | Boncyk et al. |
| 8,224,079 B2 | 7/2012 | Boncyk et al. |
| 8,229,185 B2 | 7/2012 | Ennis et al. |
| 8,238,623 B2 | 8/2012 | Stephan et al. |
| 8,306,334 B2 | 11/2012 | Paschalakis et al. |
| 8,326,031 B2 | 12/2012 | Boncyk et al. |
| 8,335,351 B2 | 12/2012 | Boncyk et al. |
| 8,437,544 B2 | 5/2013 | Boncyk et al. |
| 8,457,395 B2 | 6/2013 | Boncyk et al. |
| 8,463,030 B2 | 6/2013 | Boncyk et al. |
| 8,463,031 B2 | 6/2013 | Boncyk et al. |
| 8,465,762 B2 | 6/2013 | Lee et al. |
| 8,467,600 B2 | 6/2013 | Boncyk et al. |
| 8,467,602 B2 | 6/2013 | Boncyk et al. |
| 8,478,036 B2 | 7/2013 | Boncyk et al. |
| 8,478,037 B2 | 7/2013 | Boncyk et al. |
| 8,480,641 B2 | 7/2013 | Jacobs |
| 8,488,880 B2 | 7/2013 | Boncyk et al. |
| 8,494,264 B2 | 7/2013 | Boncyk et al. |
| 8,498,460 B2 | 7/2013 | Patwardhan |
| 8,520,942 B2 | 8/2013 | Boncyk et al. |
| 8,533,879 B1 | 9/2013 | Taylor |
| 8,548,245 B2 | 10/2013 | Boncyk et al. |
| 8,548,278 B2 | 10/2013 | Boncyk et al. |
| 8,582,817 B2 | 11/2013 | Boncyk et al. |
| 8,588,476 B1 | 11/2013 | Spicola, Jr. |
| 8,588,527 B2 | 11/2013 | Boncyk et al. |
| D697,210 S | 1/2014 | Delaney et al. |
| 8,638,986 B2 | 1/2014 | Jiang et al. |
| 8,661,915 B2 | 3/2014 | Taylor |
| 8,712,193 B2 | 4/2014 | Boncyk et al. |
| 8,718,410 B2 | 5/2014 | Boncyk et al. |
| 8,734,342 B2 | 5/2014 | Cable |
| 8,755,053 B2 | 6/2014 | Fright et al. |
| 8,768,052 B2 | 7/2014 | Kawano |
| 8,773,508 B2 | 7/2014 | Daniel et al. |
| 8,774,463 B2 | 7/2014 | Boncyk et al. |
| 8,787,621 B2 | 7/2014 | Spicola, Sr. et al. |
| 8,787,630 B2 | 7/2014 | Rowe |
| 8,795,169 B2 | 8/2014 | Cosentino et al. |
| 8,798,368 B2 | 8/2014 | Boncyk et al. |
| 8,800,386 B2 | 8/2014 | Taylor |
| 8,814,841 B2 | 8/2014 | Hartwell |
| 8,824,738 B2 | 9/2014 | Boncyk et al. |
| 8,837,868 B2 | 9/2014 | Boncyk et al. |
| 8,842,941 B2 | 9/2014 | Boncyk et al. |
| 8,849,380 B2 | 9/2014 | Patwardhan |
| D714,940 S | 10/2014 | Kim |
| 8,855,423 B2 | 10/2014 | Boncyk et al. |
| 8,861,859 B2 | 10/2014 | Boncyk et al. |
| 8,867,839 B2 | 10/2014 | Boncyk et al. |
| 8,873,891 B2 | 10/2014 | Boncyk et al. |
| 8,875,331 B2 | 11/2014 | Taylor |
| 8,885,983 B2 | 11/2014 | Boncyk et al. |
| 8,892,190 B2 | 11/2014 | Docherty et al. |
| 8,904,876 B2 | 12/2014 | Taylor et al. |

(56) References Cited

U.S. PATENT DOCUMENTS

| | | |
|---|---|---|
| 8,913,800 B2 | 12/2014 | Rowe |
| 8,923,563 B2 | 12/2014 | Boncyk et al. |
| D720,864 S | 1/2015 | Behar et al. |
| 8,938,096 B2 | 1/2015 | Boncyk et al. |
| 8,939,918 B2 | 1/2015 | Richards |
| 8,948,459 B2 | 2/2015 | Boncyk et al. |
| 8,948,460 B2 | 2/2015 | Boncyk et al. |
| D724,216 S | 3/2015 | Gant et al. |
| 8,997,588 B2 | 4/2015 | Taylor |
| 9,014,513 B2 | 4/2015 | Boncyk et al. |
| 9,014,514 B2 | 4/2015 | Boncyk et al. |
| 9,014,515 B2 | 4/2015 | Boncyk, V et al. |
| 9,020,305 B2 | 4/2015 | Boncyk et al. |
| 9,025,813 B2 | 5/2015 | Boncyk et al. |
| 9,025,814 B2 | 5/2015 | Boncyk et al. |
| 9,031,278 B2 | 5/2015 | Boncyk et al. |
| 9,036,947 B2 | 5/2015 | Boncyk et al. |
| 9,036,948 B2 | 5/2015 | Boncyk et al. |
| 9,041,810 B2 | 5/2015 | Ecker et al. |
| D735,879 S | 8/2015 | Behar et al. |
| 9,110,925 B2 | 8/2015 | Boncyk et al. |
| 9,116,920 B2 | 8/2015 | Boncyk et al. |
| 9,135,355 B2 | 9/2015 | Boncyk et al. |
| 9,141,714 B2 | 9/2015 | Boncyk et al. |
| 9,148,562 B2 | 9/2015 | Boncyk et al. |
| D740,945 S | 10/2015 | Booth |
| 9,154,694 B2 | 10/2015 | Boncyk et al. |
| 9,154,695 B2 | 10/2015 | Boncyk et al. |
| 9,167,800 B2 | 10/2015 | Spicola, Jr. |
| 9,179,844 B2 | 11/2015 | Fright et al. |
| 9,186,053 B2 | 11/2015 | Viola |
| 9,196,067 B1 * | 11/2015 | Freed ................ G01S 17/66 |
| 9,224,205 B2 | 12/2015 | Tsin et al. |
| 9,235,600 B2 | 1/2016 | Boncyk et al. |
| 9,244,943 B2 | 1/2016 | Boncyk et al. |
| 9,262,440 B2 | 2/2016 | Boncyk et al. |
| 9,268,197 B1 | 2/2016 | Digregorio et al. |
| 9,285,323 B2 | 3/2016 | Burg et al. |
| 9,288,271 B2 | 3/2016 | Boncyk et al. |
| 9,311,520 B2 | 4/2016 | Burg et al. |
| 9,311,540 B2 | 4/2016 | Ecker et al. |
| 9,311,552 B2 | 4/2016 | Boncyk et al. |
| 9,311,553 B2 | 4/2016 | Boncyk et al. |
| 9,311,554 B2 | 4/2016 | Boncyk et al. |
| 9,317,769 B2 | 4/2016 | Boncyk et al. |
| 9,324,004 B2 | 4/2016 | Boncyk et al. |
| 9,330,326 B2 | 5/2016 | Boncyk et al. |
| 9,330,327 B2 | 5/2016 | Boncyk et al. |
| 9,330,328 B2 | 5/2016 | Boncyk et al. |
| 9,330,453 B2 | 5/2016 | Soldatitsch et al. |
| 9,342,748 B2 | 5/2016 | Boncyk et al. |
| D758,608 S | 6/2016 | Behar et al. |
| 9,377,295 B2 | 6/2016 | Fright et al. |
| 9,395,234 B2 | 7/2016 | Cosentino et al. |
| 9,399,676 B2 | 7/2016 | Schurpf et al. |
| 9,438,775 B2 * | 9/2016 | Powers ................ H04N 5/2253 |
| 9,451,928 B2 | 9/2016 | Falco et al. |
| 9,525,867 B2 | 12/2016 | Thomas et al. |
| 9,528,941 B2 | 12/2016 | Burg et al. |
| 9,607,380 B2 | 3/2017 | Burg et al. |
| D783,838 S | 4/2017 | Zhao et al. |
| 9,690,904 B1 | 6/2017 | Zizi |
| 9,808,206 B1 | 11/2017 | Zhao et al. |
| 9,818,193 B2 | 11/2017 | Smart |
| 9,861,285 B2 | 1/2018 | Fright et al. |
| 9,863,811 B2 | 1/2018 | Burg |
| 9,958,383 B2 * | 5/2018 | Hall ................ G01N 21/4738 |
| 9,972,077 B2 | 5/2018 | Adiri et al. |
| 9,996,923 B2 | 6/2018 | Thomas |
| 10,013,527 B2 | 7/2018 | Fairbairn et al. |
| D827,827 S | 9/2018 | Canfield et al. |
| 10,068,329 B2 | 9/2018 | Adiri et al. |
| D831,197 S | 10/2018 | Scruggs et al. |
| 10,130,260 B2 | 11/2018 | Patwardhan |
| 10,143,425 B1 | 12/2018 | Zhao et al. |
| D837,388 S | 1/2019 | Dacosta et al. |
| 10,267,743 B2 | 4/2019 | Burg et al. |
| 10,307,382 B2 | 6/2019 | Jung et al. |
| 10,362,984 B2 | 7/2019 | Adiri et al. |
| 10,368,795 B2 | 8/2019 | Patwardhan |
| 10,559,081 B2 | 2/2020 | Omer et al. |
| RE47,921 E | 3/2020 | Patwardhan |
| D877,931 S | 3/2020 | Dacosta et al. |
| 10,614,623 B2 | 4/2020 | D'Alessandro |
| 10,617,305 B2 | 4/2020 | Patwardhan et al. |
| 10,652,520 B2 | 5/2020 | Otto et al. |
| 10,692,214 B2 | 6/2020 | Bisker |
| 10,702,160 B2 | 7/2020 | Patwardhan |
| 10,775,647 B2 | 9/2020 | Joy et al. |
| 10,777,317 B2 | 9/2020 | Fairbairn et al. |
| D898,921 S | 10/2020 | Dacosta et al. |
| D899,604 S | 10/2020 | Dacosta et al. |
| D903,863 S | 12/2020 | Dacosta et al. |
| 10,874,302 B2 | 12/2020 | Fright et al. |
| 2002/0054297 A1 | 5/2002 | Lee et al. |
| 2002/0149585 A1 | 10/2002 | Kacyra et al. |
| 2002/0197600 A1 | 12/2002 | Maione et al. |
| 2003/0004405 A1 | 1/2003 | Townsend et al. |
| 2003/0006770 A1 | 1/2003 | Smith |
| 2003/0031383 A1 | 2/2003 | Gooch |
| 2003/0036751 A1 | 2/2003 | Anderson et al. |
| 2003/0085908 A1 | 5/2003 | Luby |
| 2003/0164841 A1 | 9/2003 | Myers |
| 2003/0164875 A1 | 9/2003 | Myers |
| 2003/0229514 A2 | 12/2003 | Brown |
| 2003/0231793 A1 | 12/2003 | Crampton |
| 2004/0014165 A1 | 1/2004 | Keidar et al. |
| 2004/0059199 A1 | 3/2004 | Thomas et al. |
| 2004/0080497 A1 | 4/2004 | Enmei |
| 2004/0117343 A1 | 6/2004 | Johnson |
| 2004/0136579 A1 | 7/2004 | Gutenev |
| 2004/0146290 A1 | 7/2004 | Kollias et al. |
| 2004/0201694 A1 | 10/2004 | Gartstein et al. |
| 2004/0225222 A1 | 11/2004 | Zeng et al. |
| 2004/0264749 A1 | 12/2004 | Skladnev et al. |
| 2005/0012817 A1 | 1/2005 | Hampapur et al. |
| 2005/0027567 A1 | 2/2005 | Taha |
| 2005/0033142 A1 | 2/2005 | Madden et al. |
| 2005/0084176 A1 | 4/2005 | Talapov et al. |
| 2005/0094262 A1 | 5/2005 | Spediacci et al. |
| 2005/0111757 A1 | 5/2005 | Brackett et al. |
| 2005/0154276 A1 | 7/2005 | Barducci et al. |
| 2005/0190988 A1 | 9/2005 | Feron |
| 2005/0237384 A1 | 10/2005 | Jess et al. |
| 2005/0259281 A1 | 11/2005 | Boust |
| 2005/0273011 A1 | 12/2005 | Hattery et al. |
| 2005/0273267 A1 | 12/2005 | Maione |
| 2006/0008178 A1 | 1/2006 | Seeger et al. |
| 2006/0012802 A1 | 1/2006 | Shirley |
| 2006/0036135 A1 | 2/2006 | Kern |
| 2006/0036156 A1 | 2/2006 | Lachaine et al. |
| 2006/0044546 A1 | 3/2006 | Lewin et al. |
| 2006/0055943 A1 | 3/2006 | Kawasaki et al. |
| 2006/0058665 A1 | 3/2006 | Chapman |
| 2006/0072122 A1 | 4/2006 | Hu et al. |
| 2006/0073132 A1 | 4/2006 | Congote |
| 2006/0089553 A1 | 4/2006 | Cotton |
| 2006/0098876 A1 | 5/2006 | Buscema |
| 2006/0135953 A1 | 6/2006 | Kania et al. |
| 2006/0151601 A1 | 7/2006 | Rosenfeld |
| 2006/0204072 A1 | 9/2006 | Wetzel et al. |
| 2006/0210132 A1 | 9/2006 | Christiansen et al. |
| 2006/0222263 A1 | 10/2006 | Carlson |
| 2006/0268148 A1 | 11/2006 | Kollias et al. |
| 2006/0269125 A1 | 11/2006 | Kalevo et al. |
| 2006/0293613 A1 | 12/2006 | Fatehi et al. |
| 2007/0065009 A1 | 3/2007 | Ni et al. |
| 2007/0097381 A1 | 5/2007 | Tobiason et al. |
| 2007/0125390 A1 | 6/2007 | Afriat et al. |
| 2007/0129602 A1 | 6/2007 | Bettesh et al. |
| 2007/0229850 A1 | 10/2007 | Herber |
| 2007/0273894 A1 | 11/2007 | Johnson |
| 2007/0276195 A1 | 11/2007 | Xu et al. |
| 2007/0276309 A1 | 11/2007 | Xu et al. |

(56) References Cited

U.S. PATENT DOCUMENTS

| | | |
|---|---|---|
| 2008/0006282 A1 | 1/2008 | Sukovic |
| 2008/0021329 A1 | 1/2008 | Wood et al. |
| 2008/0045807 A1 | 2/2008 | Psota et al. |
| 2008/0088704 A1 | 4/2008 | Wendelken et al. |
| 2008/0098322 A1 | 4/2008 | Champion et al. |
| 2008/0126478 A1 | 5/2008 | Ferguson et al. |
| 2008/0165357 A1 | 7/2008 | Stem |
| 2008/0232679 A1 | 9/2008 | Hahn |
| 2008/0246759 A1 | 10/2008 | Summers |
| 2008/0275315 A1 | 11/2008 | Oka et al. |
| 2008/0285056 A1 | 11/2008 | Blayvas |
| 2008/0312642 A1 | 12/2008 | Kania et al. |
| 2008/0312643 A1 | 12/2008 | Kania et al. |
| 2009/0116712 A1 | 5/2009 | Al-Moosawi et al. |
| 2009/0118720 A1 | 5/2009 | Black et al. |
| 2009/0213213 A1* | 8/2009 | Fright .................. A61B 5/1077 348/77 |
| 2009/0221874 A1 | 9/2009 | Vinther |
| 2009/0225333 A1 | 9/2009 | Bendall |
| 2009/0234313 A1 | 9/2009 | Mullejeans et al. |
| 2010/0004564 A1 | 1/2010 | Jendle |
| 2010/0020164 A1 | 1/2010 | Perrault |
| 2010/0091104 A1 | 4/2010 | Sprigle et al. |
| 2010/0111387 A1 | 5/2010 | Christiansen, II et al. |
| 2010/0121201 A1 | 5/2010 | Papaionnou |
| 2010/0149551 A1 | 6/2010 | Malinkevich |
| 2010/0156921 A1 | 6/2010 | McLennan et al. |
| 2010/0191126 A1 | 7/2010 | Al-Moosawi et al. |
| 2010/0278312 A1 | 11/2010 | Ortiz |
| 2011/0102550 A1 | 5/2011 | Daniel et al. |
| 2011/0125028 A1 | 5/2011 | Wood et al. |
| 2011/0190637 A1 | 8/2011 | Knobel et al. |
| 2012/0035469 A1 | 2/2012 | Whelan et al. |
| 2012/0059266 A1 | 3/2012 | Davis et al. |
| 2012/0078088 A1 | 3/2012 | Whitestone et al. |
| 2012/0078113 A1 | 3/2012 | Whitestone et al. |
| 2012/0253200 A1 | 10/2012 | Stolka et al. |
| 2012/0265236 A1 | 10/2012 | Wesselmann |
| 2012/0275668 A1 | 11/2012 | Chou et al. |
| 2013/0051651 A1 | 2/2013 | Leary et al. |
| 2013/0137991 A1 | 5/2013 | Fright et al. |
| 2013/0335545 A1 | 12/2013 | Darling |
| 2014/0048687 A1 | 2/2014 | Drzymala et al. |
| 2014/0088402 A1 | 3/2014 | Xu |
| 2014/0354830 A1* | 12/2014 | Schafer .............. H04N 1/32144 348/207.1 |
| 2015/0077517 A1* | 3/2015 | Powers ................ H04N 5/2253 348/46 |
| 2015/0089994 A1 | 4/2015 | Richards |
| 2015/0142462 A1 | 5/2015 | Vaidya et al. |
| 2015/0150457 A1* | 6/2015 | Wu ...................... A61B 5/0073 600/425 |
| 2015/0214993 A1 | 7/2015 | Huang |
| 2015/0250416 A1 | 9/2015 | LaPlante et al. |
| 2015/0265236 A1 | 9/2015 | Garner et al. |
| 2015/0270734 A1 | 9/2015 | Davison et al. |
| 2016/0157725 A1* | 6/2016 | Munoz ................ A61B 5/0077 600/430 |
| 2016/0178512 A1* | 6/2016 | Hall .................. G01N 21/4738 348/135 |
| 2016/0206205 A1 | 7/2016 | Wu et al. |
| 2016/0259992 A1* | 9/2016 | Knodt .................. G06K 9/6201 |
| 2016/0261133 A1 | 9/2016 | Wang |
| 2016/0262659 A1 | 9/2016 | Fright et al. |
| 2016/0275681 A1 | 9/2016 | D'Alessandro |
| 2016/0284084 A1 | 9/2016 | Gurcan et al. |
| 2016/0338594 A1 | 11/2016 | Spahn et al. |
| 2017/0079577 A1 | 3/2017 | Fright et al. |
| 2017/0084024 A1 | 3/2017 | Gurevich |
| 2017/0086940 A1* | 3/2017 | Nakamura ............ A61B 10/00 |
| 2017/0127196 A1 | 5/2017 | Blum et al. |
| 2017/0258340 A1 | 9/2017 | Przybyszewski et al. |
| 2017/0262985 A1* | 9/2017 | Finn .................... G06T 5/30 |
| 2018/0214071 A1 | 8/2018 | Fright et al. |
| 2018/0252585 A1 | 9/2018 | Burg |
| 2018/0254100 A1 | 9/2018 | Fairbairn et al. |
| 2018/0271378 A1 | 9/2018 | Fright et al. |
| 2018/0279943 A1 | 10/2018 | Budman et al. |
| 2018/0296092 A1 | 10/2018 | Hassan et al. |
| 2018/0303413 A1 | 10/2018 | Hassan et al. |
| 2018/0322647 A1 | 11/2018 | Harrington et al. |
| 2018/0336720 A1 | 11/2018 | Larkins et al. |
| 2019/0133513 A1 | 5/2019 | Patwardhan |
| 2019/0240166 A1 | 8/2019 | Jung et al. |
| 2019/0273890 A1 | 9/2019 | Christiansen, II et al. |
| 2019/0290187 A1 | 9/2019 | Ariri et al. |
| 2019/0298183 A1 | 10/2019 | Burg et al. |
| 2019/0298252 A1 | 10/2019 | Patwardhan |
| 2019/0307337 A1 | 10/2019 | Little et al. |
| 2019/0307400 A1 | 10/2019 | Zhao et al. |
| 2019/0310203 A1 | 10/2019 | Burg et al. |
| 2019/0336003 A1 | 11/2019 | Patwardhan |
| 2019/0350535 A1 | 11/2019 | Zhao et al. |
| 2019/0369418 A1 | 12/2019 | Joy et al. |
| 2020/0014910 A1 | 1/2020 | Larkins |
| 2020/0126226 A1 | 4/2020 | Adiri et al. |
| 2020/0126227 A1 | 4/2020 | Adiri et al. |
| 2020/0196962 A1 | 6/2020 | Zhao et al. |
| 2020/0209214 A1 | 7/2020 | Zohar et al. |
| 2020/0211193 A1 | 7/2020 | Adiri et al. |
| 2020/0211228 A1 | 7/2020 | Adiri et al. |
| 2020/0211682 A1 | 7/2020 | Zohar et al. |
| 2020/0211693 A1 | 7/2020 | Adiri et al. |
| 2020/0211697 A1 | 7/2020 | Adiri et al. |
| 2020/0225166 A1 | 7/2020 | Burg et al. |
| 2020/0234444 A1 | 7/2020 | Budman et al. |
| 2020/0286600 A1 | 9/2020 | Brouwer et al. |
| 2020/0297213 A1 | 9/2020 | Patwardhan |
| 2020/0359971 A1 | 11/2020 | Zhao et al. |
| 2020/0364862 A1 | 11/2020 | Dacosta et al. |
| 2020/0383631 A1 | 12/2020 | Canfield et al. |
| 2021/0000387 A1 | 1/2021 | Zizi |
| 2021/0004995 A1 | 1/2021 | Burg et al. |

FOREIGN PATENT DOCUMENTS

| | | |
|---|---|---|
| DE | 2642841 | 3/1978 |
| DE | 3420588 | 12/1984 |
| DE | 4120074 | 1/1992 |
| EP | 119660 | 9/1984 |
| EP | 355221 | 2/1990 |
| EP | 552526 | 7/1993 |
| EP | 650694 | 5/1995 |
| EP | 1210906 | 6/2002 |
| EP | 1248237 A2 | 10/2002 |
| EP | 1351036 | 10/2003 |
| EP | 1303267 | 4/2004 |
| EP | 1584405 | 10/2005 |
| EP | 1611543 | 1/2006 |
| EP | 1467706 | 3/2007 |
| EP | 1946567 | 7/2008 |
| EP | 2272047 | 3/2012 |
| EP | 2883037 | 6/2015 |
| EP | 3114462 | 1/2017 |
| EP | 3143378 | 3/2017 |
| EP | 3160327 | 5/2017 |
| EP | 2750673 | 8/2017 |
| EP | 3251332 | 12/2017 |
| EP | 3270770 | 1/2018 |
| EP | 3286695 | 2/2018 |
| EP | 3364859 | 8/2018 |
| EP | 3365057 | 8/2018 |
| EP | 3371779 | 9/2018 |
| EP | 3371780 | 9/2018 |
| EP | 3381015 | 11/2019 |
| EP | 3586195 | 1/2020 |
| EP | 3589187 | 1/2020 |
| EP | 3602501 | 2/2020 |
| EP | 3555856 | 4/2020 |
| EP | 3655924 | 5/2020 |
| EP | 3371781 | 9/2020 |
| EP | 3707670 | 9/2020 |
| ES | 2384086 | 6/2012 |

(56) References Cited

FOREIGN PATENT DOCUMENTS

| | | |
|---|---|---|
| FR | 2570206 | 3/1986 |
| GB | 2458927 | 11/2012 |
| GB | 2544263 | 5/2017 |
| GB | 2544460 | 5/2017 |
| GB | 2544725 | 5/2017 |
| GB | 2545394 | 6/2017 |
| GB | 2557633 | 6/2018 |
| GB | 2557928 | 7/2018 |
| GB | 2559977 | 8/2018 |
| GB | 2559978 | 8/2018 |
| JP | 2011516849 | 5/2011 |
| JP | 5467404 | 4/2014 |
| NZ | 293713 | 9/1997 |
| NZ | 588740 | 7/2012 |
| WO | 2000003210 | 1/2000 |
| WO | 2000030337 | 5/2000 |
| WO | 2008057056 A1 | 5/2000 |
| WO | 2002065069 | 6/2002 |
| WO | 2002001143 | 7/2002 |
| WO | 2002093450 | 11/2002 |
| WO | 2004092874 | 10/2004 |
| WO | 2004095372 | 11/2004 |
| WO | 2005033620 | 4/2005 |
| WO | 2006078902 A2 | 7/2006 |
| WO | 2007029038 A1 | 3/2007 |
| WO | 2007043899 A1 | 4/2007 |
| WO | 2007059780 A1 | 5/2007 |
| WO | 2008033010 A1 | 3/2008 |
| WO | 2008039539 A2 | 4/2008 |
| WO | 2008048424 A2 | 4/2008 |
| WO | 2008071414 A1 | 6/2008 |
| WO | 2008080385 A1 | 7/2008 |
| WO | 2009046218 A2 | 4/2009 |
| WO | 2009122200 | 10/2009 |
| WO | 2010048960 A1 | 5/2010 |
| WO | 2012146720 | 11/2012 |
| WO | 2016069463 | 5/2016 |
| WO | 2016199134 A1 | 12/2016 |
| WO | 2017077276 | 5/2017 |
| WO | 2017077277 | 5/2017 |
| WO | 2017077279 | 5/2017 |
| WO | 2017089826 | 6/2017 |
| WO | 2018109453 | 6/2018 |
| WO | 2018109479 | 6/2018 |
| WO | 2018154271 | 8/2018 |
| WO | 2018154272 | 8/2018 |
| WO | 2018185560 A2 | 10/2018 |
| WO | 2019239106 | 12/2019 |
| WO | 2019239147 | 12/2019 |
| WO | 2020014779 | 1/2020 |
| WO | 2020141346 | 7/2020 |
| WO | 2020251938 | 12/2020 |

OTHER PUBLICATIONS

Ahroni, JH et al "Reliability of computerized wound surface area determinations" Wounds: A Compendium of Clinical Research and Practice, No. 4, (1992) 133-137.

Anderson, R., et al. "The Optics of Human Skin", The Journal of Investigative Dermatology, vol. 77, No. 1, pp. 13-19; Jul. 1981.

Armstrong, DG et al "Diabetic foot ulcers: prevention, diagnosis and classification" Am Fam Physician Mar. 15, 1998; 57 (6) :1325-32, 1337-8.

Bale, S, Harding K, Leaper D. An Introduction to Wounds. Emap Healthcare Ltd 2000.

Beaumont, E et al "RN Technology Scorecard: Wound Care Science at the Crossroads" American Journal of Nursing Dec. 1998 98(12):16-18, 20-21.

Bergstrom, N, Bennett MA, Carlson CE. Treatment of Pressure Ulcers: Clinical Practice Guideline No. 15. Rockville, MD: U.S. Department of Health and Human Services. Public Health Service, Agency for Health Care Policy and Research 1994: 95-0652: [O].

Berriss 1997: Automatic Quantitative Analysis of Healing Skin Wounds using Colour Digital Image Processing: William Paul Berriss, Stephen John Sangwine [E].

Binder, et al., "Application of an artificial neural network in epiluminescence microscopy pattern analysis of pigmented skin lesions: a pilot study", British Journal of Dermatology 130; pp. 460-465; 1994.

Bland, JM et al "Measurement error and correlation coefficients" BMJ Jul. 6, 1996; 313 (7048) :41-2.

Bland, JM et al "Measurement error" BMJ Jun. 29, 1996; 312 (7047) :1654.

Bohannon Richard; Barbara A Pfaller Documentation of Wound Surface Area from Tracings of Wound Perimeters [E].

Bostock, et al, Toward a neural network based system for skin cancer diagnosis; IEEE Conference on Artificial neural Networks, ISBN: 0-85296-573-7, pp. 215-219, May 1993.

BPG2005: Assessment and Management of Foot Ulcers for People with Diabetes:Nursing Best Practice Guidelines, Toronto, Ontario [E], Mar. 2013.

Briggs Corporation: Managed care making photo documentation a wound care standard. Wound care solutions product catalog 1997.

Brown, G "Reporting outcomes for Stage IV pressure ulcer healing: a proposal" Adv Skin Wound Care (2000)13:277-83.

Callieri 2003: Callieri M, Cignoni P, Pingi P, Scopigno R. Derma: Monitoring the evolution of skin lesions with a 3D system, VMV 2003. 8th International Fall Workshop, Vision, Modeling, and Visualization 2003, Nov. 19-21, 2003, Munich, Germany [E].

Campana: XML-based synchronization of mobile medical devices [E], 2002, 2 Pages.

Cascinelli, N., et al. "Results obtained by using a computerized image analysis system designed as an aid to diagnosis of cutaneous melanoma", Melanoma Research, vol. 2, pp. 163-170, 1992.

Collins, C et al "The Role of Ultrasound in Lower Extremity Wound Management" International Journal of Lower Extremity Wounds (2002) 1: 229-235.

Daubechies, I., "The Wavelet Transform, Time-Frequency Localization and Signal Analysis", IEEE Trans Inform Theory, vol. 36, No. 5, pp. 961-1005; Sep. 1990.

De Vet, HC et al "Current challenges in clinimetrics" J Clin Epidemiol Dec. 2003; 56 (12) :1137-41.

Debray, M., Couturier P, Greuillet F, Hohn C, Banerjee S, Gavazzi G, Franco A. "A preliminary study of the feasibility of wound telecare for the elderly." Journal of Telemedicine & Telecare 2001: 7(6): 353-8. [A].

Duff, et al. (2003), Loftus Hills A, Morrell C 2000 Clinical. Guidelines for the management of venous leg ulcers: Implementation Guide. Royal College of Nursing; 2000: 001 (213): 1-48. [E].

Ercal, F., "Detection of Skin Tumor Boundaries in Color Images", IEEE Transactions of Medical Imaging, vol. 12, No. 3, pp. 624-627, Sep. 1993.

Ercal, F., et al. "Neural Network Diagnosis of Malignant Melanoma From Color Images", IEEE Transactions of Biomedical Engineering, vol. 41, No. 9, pp. 837-845, Sep. 1994.

Ferrell, B "Pressure ulcers. Assessment of healing" Clin Geriatr Med (1997)13:575-87.

Fitzpatrick, R et al "Evaluating patient-based outcome measures for use in clinical trials" Health Technol Assess (1998); 2 (14) :i-iv, 1-74.

Flahr, et al. 2005: Clinimetrics and Wound Science [E].

Flanagan, M. "Improving accuracy of wound measurement in clinical practice" Ostomy Wound Manage Oct. 2003, 49(10):28-40.

Flanagan, M., "Wound measurement: can it help us to monitor progression to healing?" JWound Care May 2003, 12(5):189-94.

Gilman, T "Wound outcomes: the utility of surface measures" Int J Low Extern Wounds Sep. 2004; 3 (3) :125-32.

Goldman, RJ "The patientcom, 1 year later" Adv Skin Wound Care Nov.-Dec. 2002; 15 (6) :254, 256.

Goldman, RJ et al "More than one way to measure a wound: An overview of tools and techniques" Adv Skin Wound Care (2002) 15:236-45.

Golston, et al. "Automatic Detection of Irregular Borders in Malanoma and Other Skin Tumors", Computerized Medical Imaging and Graphics, vol. 16, No. 3, pp. 199-203, 1992.

(56) References Cited

OTHER PUBLICATIONS

Graaf, R., et al. "Optical properties of human dermis in vitro and in vivo", Applied Optics, vol. 32, No. 4, pp. 435-447, Feb. 1, 1993.
Greene, A., "Computer image analysis in the diagnosis of melanoma", Journal of the American Academy of Dermatology; vol. 31, No. 6, pp. 958-964, 1994.
Griffin, JW et al "A comparison of photographic and transparency-based methods for measuring wound surface area" Phys Ther Feb. 1993; 73 (2) :117-22.
Hansen 1997: Wound Status Evaluation Using Color Image Processing Gary: L. Hansen, Ephraim M. Sparrow, Jaydeep Y. Kokate, Keith J. Leland, and Paul A. Iaizzo [E].
Hayes 2003:Hayes S, Dodds, S. Digital photography in wound care. Nursing Times 2003:9(42):48-9. [A].
Herbin, et al, Color Quantitation Through Image Processing in Dermatology; IEEE Transaction on Medical Imaging, vol. 9, Issue 3, pp. 262-269, Sep. 1990.
Hibbs, P "The economics of pressure ulcer prevention" Decubitus Aug. 1988; 1 (3) :32-8.
Houghton 2000: Houghton PE, Kincaid CB, Campbell KE, Woodbury MG, Keast DH. Photographic assessment of the appearance of chronic pressure and leg ulcers. Ostomy Wound management 2000: 46(4): 20-6, 28-30. [A].
Huang, C., et al."Border irregularity: atypical moles versus melanoma", Eur J Dermatol, vol. 6, pp. 270-273, Jun. 1996.
Iakovou, D. et al., "Integrated sensors for robotic laser welding," Proceedings of the Third International WLT-Conference on Lasers in Manufacturing, Jun. 2005, pp. 1-6.
International Search Report and Written Opinion for International Application No. PCT/US2004/028445 filed Sep. 1, 2004.
Johnson, JD (1995) Using ulcer surface area and vol. To document wound size.
Jones, et al, An Instrument to Measure the Dimension of Skin Wounds; IEEE Transaction on Biomedical Engineering, ISSN: 0018-9294; vol. 42, Issue 5, pp. 464-470, May 1995.
Jones, TD "Improving the Precision of Leg Ulcer Area Measurement with Active Contour Models", PhD Thesis (1999) http://www.comp.glam.ac.uklpages/staff/tjones/ThesisOL/Title. Htm.
Jones, TD et al "An active contour model for measuring the area of leg ulcers" IEEE Trans Med Imaging Dec. 2000, 19(12):1202-10.
Kenet, R., et al. "Clinical Diagnosis of Pigmented Lesions Using Digital Epiluminescence Microscopy", Arch Dermatol, vol. 129, pp. 157-174; Feb. 1993.
Kloth, LC et al "A Randomized Controlled Clinical Trial to Evaluate the Effects of Noncontact Normothermic Wound Therapy on Chronic Full-thickness Pressure Ulcers" Advances in Skin & Wound Care Nov./Dec. 2002, 15(6):270-276.
Koren, et al, Interactive Wavelet Processing and Techniques Applied to Digital Mammography; IEEE Conference Proceedings, ISBN: 0-7803-3192-3; vol. 3, pp. 1415-1418, May 1996.
Kovesi, P., "Image Features From Phase Congruency", University of Western Australia, pp. 1-30; Technical Report 9/4, Revised Jun. 1995.
Krouskop, TA et al "A noncontact wound measurement system" J Rehabil Res Dev May-Jun. 2002, 39(3):337-45.
Kundin 1989: Kudin JI. A new way to size up a wound. American Journal of Nursing 1989: (2):206-7.
Langemo, DK et al "Comparison of 2 Wound Volume Measurement Methods" Advances in Skin & Wound Care Jul./Aug. 2001, vol. 14(4), 190-196.
Langemo, DK et al "Two-dimensional wound measurement: comparison of 4 techniques" Advances in Wound Care Nov.-Dec. 1998, 11(7):337-43.
Laughton, C et al "A comparison of four methods of obtaining a negative impression of the foot" J Am Podiatr Med Assoc May 2002; 92 (5) :261-8.
Lee, et al, A Multi-stage Segmentation Method for Images of Skin Lesions; IEEE Conference Proceedings on Communication, Computers, and Signal Processing, ISBN 0-7803-2553-2, pp. 602-605, May 1995.
Levoy, et al. "The Digital Michelangelo Project: 3D Scanning of Large Statues," ACM, 2000.
Lewis 1997: Lewis P, McCann R, Hidalgo P, Gorman M. Use of store and forward technology for vascular nursing teleconsultation service. Journal of Vascular Nursing 1997. 15(4): 116-23. [A].
Lewis, JS, Achilefu S, Garbow JR, Laforest R, Welch MJ., Small animal imaging. current technology and perspectives for oncological imaging, Radiation Sciences, Washington University School of Medicine, Saint Louis, MO, USA, Eur J Cancer. Nov. 2002;38(16):2173-88.
Li, D. 2004, Database design and implementation for wound measurement system. Biophotonics, 2004: 42-43. [E].
Lorimer, K "Continuity through best practice: design and implementation of a nurse-led community leg-ulcer service" Can J Nurs Res Jun. 2004, 36(2):105-12.
Lowery et al., "Technical Overview of a Web-based Telemedicine System for Wound Assessment," Advances in Skin & Wound Care, Jul./Aug. 2002, pp. 165-169, vol. 15, No. 4.
Lowson, S., "The safe practitioner: Getting the record straight: the need for accurate documentation," J Wound Care, Dec. 2004, vol. 13, No. 10, [retrieved on Dec. 17, 2004). Retrieved from the Internet: <URL: http://www.journalofwoundcare.com/nav?page= jowc.article&resource=I455125>, 2 pages.
Lucas, C., "Pressure ulcer surface area measurement using instant full-scale photography and transparency tracings," Advances in Skin & Wound Care, Jan/Feb 2002, [retrieved on Jul. 28, 2006]. Retrieved from the Internet: <URL: http://www.findarticles.com/p/articles/mi _qa3977/is_200201 /ai_n904 . . . >, 7 pages.
Lunt, M.J., "Review of duplex and colour Doppler imaging of lower-limb arteries and veins," World Wide Wounds, 2000, [retrieved on Apr. 17, 2005). Retrieved from the Internet: <URL: http://www.worldwidewounds.com/2000/sept/Michael-Lunt/Dopple . . . >, 6 pages.
Maglogiannis et al., "A system for the acquisition of reproducible digital skin lesions images," Technol and Health Care, 2003, pp. 425-441, vol. 11.
Malian et al., "Medphos: A New Photogrammetric System for Medical Measurement," 2004, Commission V, WG V/3, 6 pages.
Mallat, S., et al. "Characterization of signals from multiscale edges", IEEE Trans Patt and Mech Int'l; 14:710-732; 1992.
Marchesini, R., et al. "In vivo Spectrophotometric Evaluation of Neoplastic and Non-Neoplastic Skin Pigmented Lesions. III. CCD Camera-Based Reflectance Imaging", Photochemistry and Photobiology, vol. 62, No. 1, pp. 151-154; 1995.
Marjanovic et al., "Measurement of the volume of a leg ulcer using a laser scanner," Physiol. Meas., 1998, pp. 535-543, vol. 19.
Mastronjcola et al., "Burn Depth Assessment Using a Tri-stimulus Colorimeter," Wounds—ISSN: 1044-7946, Sep. 2005, pp. 255-258, vol. 17, No. 9.
McCardle, J., "Visitrak: wound measurement as an aid to making treatment decisions," The Diabetic Foot, Winter 2005, [retrieved onMar. 30, 2008). Retrieved from the Internet: <URL: http://findarticles.com/p/articles/mi_ mOMDQ/is_ 4_8/ai_n16043804/print>, 4 pages.
Menzies, S., "The Morphologic Criteria of the Pseudopod in Surface Microscopy", Arch Dermatol, vol. 131, pp. 436-440, Apr. 1995.
Nachbar, et al., "The ABCD rule of dermatology", Journal of the American Academy of Dermatology, vol. 3, No. 4, pp. 551-559, Apr. 1994.
National Pressure Ulcer Advisory Panel, "FAQ: Photography for pressure ulcer documentation," 1 1P56, 4 pages.
National Pressure Ulcer Advisory Panel, Position Statement, 1998, [retrieved on Jan. 6, 2005]. Retrieved from the Internet: <URL: http://www.npuap.org/>, 2 pages (Pressure Ulcer Healing Chart attached, 2 pages).
Oduncu et al., "Analysis of Skin Wound Images Using Digital Color Image Processing: A Preliminary Communication," Lower Extremity Wounds, 2004, pp. 151-156, vol. 3, No. 3.
Pages, Jordi, et al., "Plane-to-plane positioning from image-based visual serving and structured light," Proceedings of 2004 IEEE/RSJ International Conference on Intelligent Robots and Systems, Sep. 28-Oct. 2, 2004, pp. 1004-1009.

(56) References Cited

OTHER PUBLICATIONS

Patete et al., "A non-invasive, three-dimensional, diagnostic laser imaging system for accurate wound analysis," Physiol. Meas., 1996, pp. 71-79, vol. 17.
Pehamberger, H., et al. "In vivo epiluminescence microscopy of pigmented skin lesions. I. Pattern analysis of pigmented skin lesions", Journal of American Academy of Dermatology, vol. 17, No. 4, pp. 571-583, Oct. 1987.
Plassman, et al. "Problems of Assessing Wound Size," Would healing Research Unit, University of Wales College of Medicine, Cardiff CF4 4XN, Wales, UK (1993) (Unpublished).
Plassmann et al., "MAVIS: a non-invasive instrument to measure area and volume of wounds," Medical Engineering & Physics, 1998, pp. 332-338, vol. 20.
Plassmann, P., "Recording Wounds—Documenting Woundcare," Medical Computing Group, 1998, pp. 1-31.
Romanelli et al., "Technological Advances in Wound Bed Measurements," Wounds, 2002, pp. 58-66, vol. 14, No. 2, [retrieved on Apr. 8, 2005]. Retrieved from the Internet: <URL: http:/lwww.medscape.com/viewarticle/430900_print>, 8 pages.
Russell, L., "The importance of wound documentation & classification," British J Nursing, 1999, pp. 1342-1354, vol. 8, No. 20.
Salcido, R., "The Future of Wound Measurement," Advances in Skin & Wound Care, Mar./Apr. 2003, pp. 54, 56, vol. 13, No. 2.
Salmhofer, et al., "Wound teleconsultation in patients with chronic leg ulcers," 2005.
Sani-Kick et al., "Recording and Transmission of Digital Wound Images with the Help of a Mobile Device," 2002, 2 pages.
Santamaria et al., "The effectiveness of digital imaging and remote expert wound consultation on healing rates in chronic lower leg ulcers in the Kimberley region of Western Australia," Primary Intention, May 2004, pp. 62-70, vol. 12, No. 2.
Schindewolf, et al. "Comparison of classification rates for conventional and dermatoscopic images of malignant and benign melanocytic lesions using computerized colour image analysis", Eur J Dermatol, vol. 3, No. 4, pp. 299-303, May 1993.
Schindewolf, T., et al. "Classification of Melanocytic Lesions with Color and Texture Analysis Using Digital Image Processing", the International Academy of Cytology, Analytical and Quantitative Cytology and Histology, vol. 15, No. 1, pp. 1-11, Feb. 1993.
Schindewolf, T., et al. "Evaluation of different image acquisition techniques for a computer vision system in the diagnosis of malignant melanoma", Journal of the American Academy of Dermatology, vol. 31, No. 1, pp. 33-41, Jul. 1994.
Schultz et al., "Wound bed preparation: a systematic approach to wound management," Wound Repair and Regeneration, Mar./Apr. 2003, p. SI-S28, vol. 1 1, No. 2, Supplement.
Sheehan et al., "Percent Change in Wound Area of Diabetic Foot Ulcers Over a 4-Week Period Is a Robust Predictor of Complete Healing in a 12-Week Prospective Trial," Diabetes Care, Jun. 2003, pp. 1879-1882, vol. 26, No. 6.
Sheng, Chao, Brian W. Pogue, Hamid Dehghani, Julia A. O'Hara, P. J. Hoopes, Numerical light dosimetry in murine tissue: analysis of tumor curvature and angle of incidence effects upon fluence in the tissue, Proc. SPIE, vol. 4952, 39 (2003), DOI:10.1117/12.474081, Online Publication Date: Jul. 28, 2003.
Smith & Nephew, "Leg ulcer guidelines: a pocket guide for practice," National Guideline Clearinghouse, U.S. Dept of Health & Human Services, 2002, [retrieved on Jan. 10, 2012]. Retrieved from the Internet: <URL: http://guidelines.gov/content.aspx?id=9830&search=Pressure+Ulcer>, 17 pages.
Smith & Nephew, "Visitrak Wound Measurement Device," Wound Management, [retrieved on Apr. 7, 2005]. Retrieved from the Internet: <URL: http://wound.smith-nephew.com/us/node.asp?NodeId=3 I20>, 7 pages.
Smith & Nephew, "Guidelines for the Management of Leg Ulcers in Ireland" www.smith-nephew.com.
Smith et al., "Three-Dimensional Laser Imaging System for Measuring Wound Geometry," Lasers in Surgery and Medicine, 1998, pp. 87-93, vol. 23.
Sober, et al., "Computerized Digital Image Analysis: An Aid for Melanoma Diagnosis", The Journal of Dermatology, vol. 21, pp. 885-890, 1994.
Solomon et al., "The use of video image analysis for the measurement of venous ulcers," British J Dermatology, 1995, pp. 565-570, vol. 133.
Steiner, a., "In vivo epiluminescence microscopy of pigmented skin lesions. II. Diagnosis of small pigmented skin lesions and early detection of malignant melanoma", Journal of the American Academy of Dermatology, vol. 17, No. 4, pp. 584-591; Oct. 1987.
Stoecker, et al. "Automatic Detection of Asymmetry in Skin Tumors", Computerized Medical Imaging and Graphics, vol. 16, No. 3, pp. 191-197, 1992.
Takiwaki, et al., "A rudimentary system for automatic discrimination among basic skin lesions on the basis of color analysis of video images", Journal of the American Academy of Dermatology, vol. 32, No. 4, pp. 600-604, Apr. 1995.
Tellez, R., "Managed Care Making Photo Documentation a Wound Care Standard," Wound Care, 1997, [retrieved on Aug. 29, 2005]. Retrieved from the Internet: <URL: http://woundcare.org/newsvol2n4/arl.htm>, 2 pages.
Thawer et al., "A Comparison of Computer-Assisted and Manual Wound Size Measurement," Ostomy Wound Management, Oct. 2002, pp. 46-53, vol. 48, No. IO.
Umbaugh et al., "Automatic Color Segmentation Algorithms with Application to Skin Tumor Feature Identification", IEEE Engineering in Medicine and Biology, pp. 75-82, Sep. 1993.
Umbaugh, et al., "An Automatic Color Segmentation Algorithm with Application to Identification of Skin Tumor Borders", Computerized Medical Imaging and Graphics, vol. 16, No. 3, pp. 227-235, May-Jun. 1992.
Umbaugh, et al., "Automatic Color Segmentation of Images with Application to Detection of Variegated Coloring in Skin Tumors", IEEE Engineering in Medicine and Biology Magazine, Dec. 1989, pp. 43-52.
Vermolen et al., "A simplified model for growth factor induced healing of circular wounds," 2005, pp. 1-15.
Voigt, H., et al. "Topodermatographic Image Analysis for Melanoma Screening and the Quantitative Assessment of Tumor Dimension Parameters of the Skin", Cancer, vol. 75, No. 4, Feb. 15, 1995.
Walker, N, Rogers A, Birchall N, Norton R, MacMahon S. Leg ulcers in New Zealand: age at onset, recurrence and provision of care in an urban population. NZ Med J; 2002; 115(1156):286-9.
Walker, N, Vandal A, Holden K, Rogers A, Birchall N, Norton R, Triggs C, MacMahon S. Does capture-recapture analysis provide more reliable estimates of the incidence and prevalence of leg ulcers in the community? Aust NZJ Public Health 2002; 26(5):451-5.
Walker, N., Rodgers A, Birchall N, Norton R, MacMahon S. The occurrence of leg ulcers in Auckland: results of a population-based study. NZ Med J; 2002: 115 (1151): 159-162.
Wallenstein et al., "Statistical analysis of wound-healing rates for pressure ulcers," Amer J Surgery, Jul. 2004 (Supplement), pp. 73S-78S, vol. 188.
Wilbright, W.A., The Use of Telemedicine in the Management of Diabetes-Related Foot Ulceration: A Pilot Study, Advances in Skin & Wound Care, Jun. 2004, [retrieved on Jul. 28, 2006]. Retrieved from the Internet: <URL: http://www.findarticles.com/p/articles/mi_qa3977/is_200406/ai_n942 . . . >, 6 pages.
Wild et al., "Wound healing analysis and measurement by means of colour segmentation," ETRS Poster Presentation V28, Sep. 15, 2005, V28-I 7, 1 page.
Williams, C., "The Verge Videometer wound measurement package," British J Nursing, Feb./Mar. 2000, pp. 237-239, vol. 9, No. 4.
Woodbury et al., 37 Pressure ulcer assessment instruments: a critical appraisal, Ostomy Wound Management, May 1999, pp. 48-50, 53-55, vol. 45, No. 5, [retrieved on Dec. 8, 2005]. Retrieved from the Internet: <URL: http://gateway.ut.ovid.com.ezproxy.otago.ac.nzigw2/ovidweb.cgi>, 2 pages.
Zhao, et al, The Classification of the Depth of Burn Injury Using Hybrid Neural Network; IEEE Conference on Engineering in Medicine and Biology Society, ISBN 0-7803-2475-7; vol. 1, pp. 815-816, Sep. 1995.

(56) References Cited

OTHER PUBLICATIONS

Zimmet, "Venous Leg Ulcers: Evaluation and Management," American College of Phlebology. 1998.
Zuijlen, PPM., Angeles AP, Suijker MH, Kreis RW, Middelkoop E. Reliability and Accuracy of Techniques for Surface Area Measurements of Wounds and Scars. The International Journal of Lower Extremity Wounds 2004: 3(1) 7-11.
Thali, M.J., et al. "Optical 3D surface digitizing in forensic medicine: 3D documentation of skin and bone injuries." Forensic Science International. 2003.
Ahn et al., "Advances in Wound Photography and Assessment Methods," Advances in Skin & Wound Care, Feb. 2008, pp. 85-93.
Bolton, L., "Re Measuring Wound Length, Width, and Area: Which Technique?" Letters, Advances in Skin & Wound Care, pp. 450-452, vol. 21, No. 10.
Briers, J.D., "Laser speckle contrast imaging for measuring blood flow," Optica Applicata, 2007, pp. 139-152, vol. XXXVII, No. 1-2.
Cardinal et al., "Early healing rates and wound area measurements are reliable predictors of later complete wound closure," Wound Rep. Reg., 2008, pp. 19-22, vol. 16.
Cardinal et al., "Wound shape geometry measurements correlate to eventual wound healing," Wound Rep. Reg., 2009, pp. 173-178, vol. 17.
Cleator et al., "Mobile wound care: Transforming care through technology," Rehab & Community Care Medicine, Winter 2008, pp. 14-15.
De Vet, H C., et al., "When to use agreement versus reliability measures", J Clin Eoidemiol 59 (10), (Oct. 2006), 1033-9.
Duckworth et al., "A Clinically Affordable Non-Contact Wound Measurement Device," 2007, pp. 1-3.
Fette, A.M., "A clinimetric analysis of wound measurement tools," World Wide Wounds, 2006, [retrieved on Jul. 26, 2006]. Retrieved from the Internet: <URL: http://www.worldwidewounds.com/2006/January/Fette/Clinimetric-Ana . . . >, 6 pages.
Gethin et al., "Wound Measurement: the contribution to practice," EWMA Journal, 2007, pp. 26-28, vol. 7, No. 1.
Haghpanah et al., "Reliability of Electronic Versus Manual Wound Measurement Techniques," Arch Phys Med Rehabil, Oct. 2006, pp. 1396-1402, vol. 87.
HSA Global, "Mobile Wound Care", Marketing material (2009).
International Search Report and Written Opinion dated Jan. 23, 2019, International Application No. PCT/IB2018/000447, 20 pages.
International Search Report and Written Opinion dated Jul. 2, 2019, International Application No. PCT/IB2018/001572, 17 pages.
International Search Report and Written Opinion dated Mar. 1, 2007, International Application No. PCT/NZ2006/000262, 12 pages.
Kecelj-Leskovec et al., "Measurement of venous leg ulcers with a laser-based three-dimensional method: Comparison to computer planimetry with photography," Wound Rep Reg, 2007, pp. 767-771, vol. 15.
Khashram et al., "Effect of TNP on the microbiology of venous leg ulcers: a pilot study," J Wound Care, Apr. 2009, pp. 164-167, vol. 18, No. 4.
Korber et al., "Three-dimensional documentation of wound healing: First results of a new objective method for measurement," JDDG, Oct. 2006, (Band 4), pp. 848-854.
Lakovou, D. et al., "Integrated sensors for robotic laser welding," Proceedings of the Third International WLT-Conference on Lasres in Manufacturing, Jun. 2005, pp. 1-6.
Langemo et al., "Measuring Wound Length, Width, and Area: Which Technique?", Advances in Skin & Wound Care, Jan. 2008, pp. 42-45, vol. 21, No. I.
Liu et al., "Wound measurement by curvature maps: a feasibility study," Physiol. Meas., 2006, pp. I 107-1123, vol. 27.
Molnar et al., "Use of Standardized, Quantitative Digital Photography in a Multicenter Web-based Study," 2009, ePlasty, pp. 19-26, vol. 9.
Payne, C., "Cost benefit comparison of plaster casts and optical scans of the foot for the manufacture of foot orthoses," AJPM, 2007, pp. 29-31, vol. 41, No. 2.
Rogers et al., "Measuring Wounds: Which Stick to Use?", Podiatry Management, Aug. 2008, pp. 85-90.
Salcido, R., "Pressure Ulcers and Wound Care," Physical Medicine and Rehabilitation, eMedicine, 2006, [retrieved on]. Retrieved from the Internet: <URL: http://www.emedicine.com/pmr/topic 179.htrn>, 25 pages.
Shaw et al., "An Evaluation of Three Wound Measurement Techniques in Diabetic Foot Wounds," Diabetes Care, 2007, [retrieved on Mar. 30, 2008]. Retrieved from the Internet: <URL: http://care.diabetesjournals.org/cgi/content/full/30/ I 0/2641 ?ck=nck>, 5 pages.
Treuillet et al., "Three-Dimensional Assessment of Skin Wounds Using a Standard Digital Camera," IEEE Transactions on Medical Imaging, May 2009, pp. 752-762, vol. 28, No. 5.
Wang et al., "A comparison of digital planimetry and transparency tracing based methods for measuring diabetic cutaneous ulcer surface area," Zhongguo Xiu Fu Chong Jian Wai Ke Za Zhi, May 2008, pp. 563-566, vol. 22, No. 5, [retrieved on Sep. 15, 2009]. Retrieved from the Internet: <URL: http://www.ncbi.nlm.nih.gov/pu bmed/ I 8630436?ordinalpos= I &itool=E . . . >, I page.
Wendelken et al., "Key Insights on Mapping Wounds With Ultrasound," Podiatry Today, Jul. 2008, [retrieved on Jul. 14, 2008]. Retrieved from the Internet: <URL: http://www.podiatrytoday.com/article/5831>, 5 pages.

\* cited by examiner

ANATOMICAL SURFACE ASSESSMENT METHODS, DEVICES AND SYSTEMS

CROSS-REFERENCE TO RELATED APPLICATION

The present application claims the benefit of and priority to U.S. Provisional Patent Application No. 62/423,709, filed Nov. 17, 2016, and entitled "ANATOMICAL SURFACE ASSESSMENT METHODS, DEVICES AND SYSTEMS", the disclosure of which is incorporated herein by reference in its entirety.

TECHNICAL FIELD

The present technology is generally related to devices, systems and methods for assessing anatomical surface features.

BACKGROUND

Various techniques have been used to monitor wounds, ulcers, sores, lesions, tumours etc. (herein referred to collectively as "wounds") both within hospitals and for outpatients. Typically these wounds are flat or concave and up to 150 millimetres (around 6 inches) across, though larger wounds are also possible. Manual techniques are typically labour-intensive and require examination and contact by skilled personnel. Such measurements may be inaccurate and there may be significant variation between measurements made by different personnel. Further, these approaches may not preserve any visual record for review by an expert or for subsequent comparison.

A number of techniques for the automated monitoring of wounds have been proposed. A common approach is to place a reference object next to the wound, capture an image, and determine the size of the wound utilising the scale of the reference object. It is often undesirable to place a reference object near to a wound and this requires an additional cumbersome step for a user and risks contamination of the wound. Further, when the target is not in the plane of the wound, or if it is oblique, or if the wound is not planar, there will be errors in any area calculation. Further, a reference object may be misplaced.

It is an object of the present technology to provide improved devices, systems, and methods for assessing and/or treating wounds and/or other anatomical features.

SUMMARY

According to a particular embodiment there is provided a method of assessing a feature on a patient's skin surface including: receiving a first image of the patient's skin surface captured at a first time; and determining one or more dimensions of the feature at the first time, from the first image, in arbitrary units. A second image of the patient's skin surface may be received, having been captured at a second time; the method including identifying one or more anatomical features of the patient that are present in both the first and second images; determining a relative scale factor between the first and second images based on the identified anatomical features; and determining one or more dimensions of the feature at the second time, from the second image and the relative scale factor, in the arbitrary units.

The first time may precede the second time, or the second time may precede the first time.

A registration may be performed between the first and second images and the relative scale factor derived from that registration.

The method may include determining a trend of the one or more dimensions over time and displaying said trend to a user. The trend may be compared to a predicted trend and a notification may be issued to a user if the trend departs from the predicted trend.

The method may include, subsequently, obtaining calibration data and determining the one or more dimensions at at least one of the first time and the second time, in absolute units.

The determined dimensions may be displayed to a user and/or stored in memory.

The first image may be captured using a first capture device. A first processor may perform the determining of the one or more dimensions of the feature at the first time. The first processor may be in one of: the first capture device; a personal computing device; and a server computer.

The second image may be captured using the first capture device or a second capture device. The first processor or a second processor may perform the determining of one or more dimensions of the feature at the second time. Where used, the second processor may be in one of: the second capture device; a personal computing device; and a server computer.

According to another embodiment there is provided a method of assessing a feature on a patient's skin surface including: receiving a first image of the patient's skin surface captured at a first time and calibration data associated with the first image; receiving a second image of the patient's skin surface captured at a second time; identifying one or more anatomical features of the patient that are present in both the first and second images; determining a relative scale factor between the first and second images based on the identified anatomical features; and determining one or more dimensions of the feature at the second time, from the second image and the relative scale factor.

The first time may precede the second time, or the second time may precede the first time.

The calibration data may include one or more of: data including an image, captured by a device capable of determining a scale associated with the image; manually obtained measurement data; data including an image, the image including a known-size fiducial.

A trend of the one or more dimensions over time may be determined and displayed to a user. The trend may be compared to a predicted trend and a notification may be issued to a user if said trend departs from the predicted trend.

The determined dimensions may be displayed to a user and/or stored in memory.

The first image may be captured using a first capture device. A first processor may perform the determining of the one or more dimensions of the feature at the first time. The first processor may be in one of: the first capture device; a personal computing device; and a server computer.

The second image may be captured using the first capture device or a second capture device. The first processor or a second processor may perform the determining of one or more dimensions of the feature at the second time. Where used, the second processor may be in one of: the second capture device; a personal computing device; and a server computer.

In a further embodiment there is provided a method of assessing a feature on a patient's skin surface including: displaying a guide image overlaid on a real-time camera view on a display of a capture device, the capture device including a camera, whereby a user may align the camera relative to the feature by moving the capture device to align the real-time camera view with the overlaid guide image; and capturing an image of the patient's skin surface using the camera.

The guide image may include one or more of: a previously captured image of the patient's skin surface; one or more portions of a previously captured image of the patient's skin surface; one or more guide masks or markings based on a previously captured image of the patient's skin surface; one or more guide masks or markings selected from a library of available guide masks or markings; and one or more guide patterns that vary with range.

In another embodiment there is provided a method of assessing a feature on a patient's skin surface including: at a first time, capturing a first image of the patient's skin surface; at a second time, projecting a guide image onto the patient's skin surface using a projector, the projector being coupled to or incorporated in a capture device including a camera, the guide image including one or more of: all of the first image, or one or more portions of the first image; and one or more markings based on the first image; whereby a user may align the camera to a position and field of view corresponding to the first image by moving the capture device to align the projected guide with the anatomy of the patient; and capturing an image of the patient's skin surface using the camera.

In another embodiment there is provided a method of assessing a feature on a patient's skin surface including: using a capture device including an autofocus camera, capturing an image of the patient's skin surface; retrieving focal data from the camera; determining a scale associated with the captured image based on the retrieved focal data; determining one or more dimensions of the feature based on the image and the determined scale.

In some embodiments, retrieving focal data from the camera may include: driving the camera through a range of focal distances; capturing a plurality of calibration images at different focal distances within the range; determining a focal metric for each calibration image; fitting a curve through the focal metrics; and determining a focal distance value for a point of peak focal quality.

The method may include determining a temperature and applying a correction based on the determined temperature to the focal data.

At a different time, using the same or a different capture device including an autofocus camera, a further image may be captured of the patient's skin surface. Further focal data may be retrieved from the camera and a further scale associated with the captured further image may be determined based on the retrieved further focal data. One or more dimensions of the feature may be determined at the different time, based on the further image and the determined further scale; and a trend of the one or more dimensions over time may be determined and displayed to a user.

A trend of the one or more dimensions over time may be determined and displayed to a user. The trend may be comparted to a predicted trend and a notification may be issued to a user if said trend departs from the predicted trend.

The determined dimensions may be displayed to a user and/or stored in memory.

A first processor may perform the determining of the one or more dimensions of the feature. The first processor may be in one of: the capture device; a personal computing device; and a server computer.

In a further embodiment there is provided a method of assessing a feature on a patient's skin surface including: capturing an image of the patient's skin surface using a capture device including a first camera and an auxiliary camera; based on a common image region covered by both the first camera and the auxiliary camera and a known baseline between an optical axis of the first camera optical axis and an optical axis of the second camera, determining a range to the patient's skin surface; and from the range determining a scale associated with the image.

The auxiliary camera may have a different focal length to the first camera.

The auxiliary camera may have a different spectral response than the first camera.

In another embodiment there is provided a method of assessing a feature on a patient's skin surface including: using a capture device including a camera, capturing at least a first image of the patient's skin surface from a first position of the capture device and a second image of the patient's skin surface from a second position of the capture device; determining at least a distance between the first position and the second position; based on a common image region present in the first and second images and the determined distance, determining a range to the patient's skin surface; and from the range determining a scale associated with the image.

Determining at least the distance may be performed by an inertial measurement unit.

It is acknowledged that the terms "comprise", "comprises" and "comprising" may, under varying jurisdictions, be attributed with either an exclusive or an inclusive meaning. For the purpose of this specification, and unless otherwise noted, these terms are intended to have an inclusive meaning—i.e., they will be taken to mean an inclusion of the listed components which the use directly references, and possibly also of other non-specified components or elements.

BRIEF DESCRIPTION OF THE DRAWINGS

The accompanying drawings which are incorporated in and constitute part of the specification, illustrate embodiments of the present technology and, together with the general description of the present technology given above, and the detailed description of embodiments given below, serve to explain the principles of the present technology, in which.

DETAILED DESCRIPTION

Overview

Described herein is a software facility for automatically assessing an anatomical surface feature ("the facility"), such as a wound, and for managing information related to assessed anatomical surface features across a range of patients and institutions. While the following discussion liberally employs the term "wound" to refer to the anatomical surface feature(s) being assessed, the present devices, systems, and methods may be straightforwardly applied to anatomical surface features of other types, such as ulcers, sores, lesions, tumors, bruises, burns, moles, psoriasis, keloids, skin cancers, erythema, cellulitis, and the like. Similarly, a wide variety of users may use the facility, including doctors, nurses, technologists, or any other caregiver of the patient, or the patient.

As discussed in greater detail below, the facility may be implemented using readily available portable computing devices, thereby taking advantage of existing device capabilities without the need for separate hardware attachments (although in some embodiments auxiliary hardware devices may be used). As used herein, the terms "computer" and "computing device" generally refer to devices that have a processor and non-transitory memory, as well as any data processor or any device capable of communicating with a network. Data processors include programmable general-purpose or special-purpose microprocessors, programmable controllers, application-specific integrated circuits (ASICs), programming logic devices (PLDs), system on chip (SOC) or system on module (SOM) ("SOC/SOM"), an ARM class CPU with embedded Linux or Android operating system or the like, or a combination of such devices. Computer-executable instructions may be stored in memory, such as random access memory (RAM), read-only memory (ROM), flash memory, or the like, or a combination of such components. Computer-executable instructions may also be stored in one or more storage devices, such as magnetic or optical-based disks, flash memory devices, or any other type of non-volatile storage medium or non-transitory medium for data. Computer-executable instructions may include one or more program modules, which include routines, programs, objects, components, data structures, and so on that perform particular tasks or implement particular abstract data types.

Anatomical Surface Feature Assessment

Figure 1:
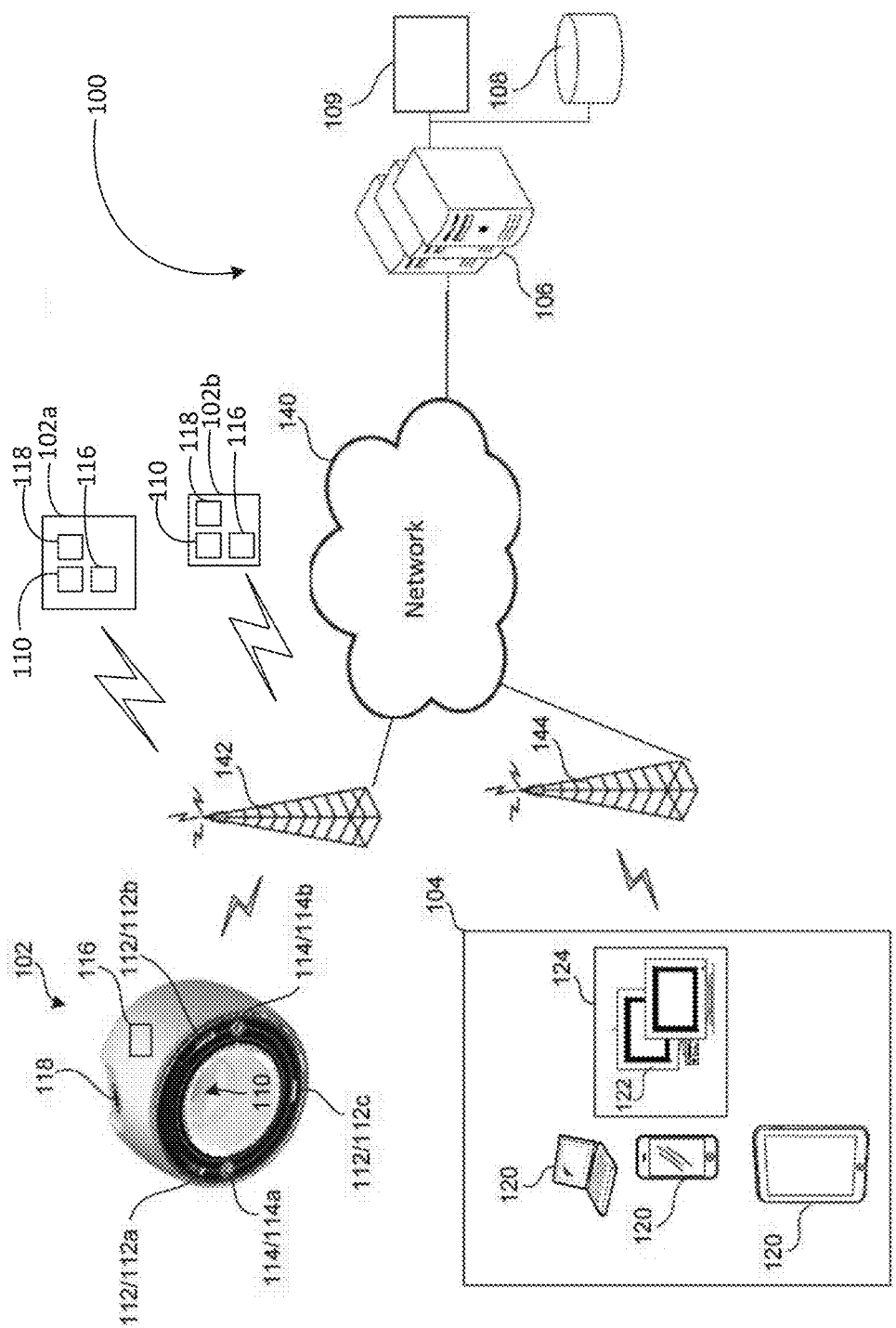
FIG. 1 is a diagram showing some of the components typically incorporated in at least some of the computer systems and other devices on which the facility executes.

FIG. 1 is a block diagram showing a sample environment having multiple components in which the facility executes. The environment 100 may include one or more capture devices 102, 102a, 102b, one or more personal computing devices 104, one or more server computers 106, and one or more persistent storage devices 108. The capture device 102, 102a, 102b and the personal computing device 104 communicate (wirelessly or through a wired connection) with the server computer 106 through a network 140 such as, for example, a Local Area Network (LAN), a Wide Area Network (WAN), and/or the Internet. In the embodiment shown in FIG. 1, the capture device 102, 102a, 102b may or may not communicate directly with the personal computing device 104. For example, the capture device 102, 102a, 102b may communicate wirelessly with a first base station or access point 142 using a wireless mobile telephone standard, such as the Global System for Mobile Communication (GSM), or another wireless standard, such as IEEE 802.11, and the first base station or access point 142 communicates with the server computer 106 via the network 140. Likewise, the computing device 104 may communicate wirelessly with a second base station or access point 144 using a wireless mobile telephone standard, such as the Global System for Mobile Communication (GSM), or another wireless standard, such as IEEE 802.11, and the second base station or access point 144 communicates with the server computer 106 via the network 140. As such, confidential patient data generated by the capture device 102, 102a, 102b is only temporarily stored locally, or not at all, and instead is permanently stored at the storage device 108 associated with the server computer 106. The facility can be practiced on any of the computing devices disclosed herein (e.g., one or more personal computing devices 104, one or more server computers 106, etc.), and may include an interface module that generates graphical user interfaces (GUIs) to allow users to access the facility (as described in greater detail below with reference to FIGS. 2-16.

The personal computing device 104 can include one or more portable computing devices 120 (e.g., a smart phone, a laptop, a tablet, etc.) and/or one or more desktop computing devices 122. During data capture with the capture device 102, 102a, 102b at the point-of-care, the personal computing device 104 may also be present (i.e., in the same treatment room), or the personal computing device 104 may be remote (i.e., outside of the treatment room but in the same treatment facility, outside of the treatment room and remote from the treatment facility, etc.). The desktop computing devices 122, if utilized, are typically associated with a particular property, e.g., a medical treatment center 124 (e.g., a hospital, a doctor's office, a clinic, etc.). The portable computing devices 120 and desktop computing devices 124 communicate with each other and the server computer 106 through networks including, for example, the Internet. In some instances the portable computing devices 120 and desktop computing devices 122 may communicate with each other through other wireless protocols, such as near field or Bluetooth.

The capture device 102, 102a, 102b is a handheld, portable imaging device that includes one or more sensing devices for generating data characterizing the wound ("wound data") at the point-of-care. In the embodiment shown in FIG. 1, the capture device 102 may include an image sensor 110 (e.g., a digital camera), a depth sensor 112 (also known as a "range imager"), and a computing device 116 (shown schematically) in communication with the image sensor 110 and the depth sensor 112.

Alternatively, in some embodiments the capture device may be a smartphone 102a, tablet 102b or other capture device including an image sensor 110 and a computing device 116. The capture device may for example be an iPhone, iPad, Android phone, other Smartphone, tablet etc). The capture device may include one, two or some other number of cameras, and/or structured light arrangements, 3D cameras etc. In such embodiments a separate personal computing device 104 may not be required. As discussed below, an auxiliary device may be mounted to or connected to a capture device 102, 102a, 102b.

Further a variety of different capture devices 102, 102a, 102b may be used in the environment 100. Different types of capture device 102, 102a, 102b may be used to capture data in relation to the same wound, at the same or different times, by the same or different users. The data from a variety of different capture devices 102, 102a, 102b may be processed in the facility.

The capture device 102, 102a, 102b is also in wireless communication with the server computer 106 (e.g., via the network 140). The image sensor 110 is configured to generate image data of the wound (e.g., pixels containing RGB color data). Where provided, the depth sensor 112 is configured to generate depth data characterizing the depth or topography of the wound. For example, in some embodiments the depth sensor 112 is a structured light device configured to emit structured light (e.g., one or more lasers, DLP projectors, film projectors, etc. where the emitted light may be infra-red, visible, ultraviolet, etc.) in a predetermined arrangement toward the wound. In such embodiments, for example, the depth sensor 112 may comprise three laser elements (labeled 112a-112c) spaced apart around a circumference of the capture device 102. The laser elements 112a-112c have a fixed positional relationship with respect to one another, and also with respect to the image sensor 110. Together the laser elements 112a-112c can be configured to create a structured light pattern (e.g., a laser point(s), a laser fan(s), etc.) In some embodiments the laser elements do not need to be symmetrically arranged. In other embodiments, the depth sensor 112 can include other suitable devices for range imaging, such as an ultrasonic sensor, a stereo camera, a plenoptic camera, a time-of-flight camera, an ISM band miniature radar, etc.

The capture device 102, 102a, 102b also includes a rechargeable power source and an actuator 118 (e.g., a button, a switch, touch screen etc.) for initiating data capture. When a user presses the actuator 118, the computing device 116 activates the image sensor 110 (and the depth sensor 112 if included) to generate data. The computing device 116 then communicates the captured data to the remote server computer 106 for further processing by the facility. In some embodiments, the computing device 116 may partially or completely process the captured data before communicating the captured data to the remote server computer 106. In some embodiments, the computing device 116 wirelessly communicates with the server computer 106 (e.g., over a network). Such a cordless arrangement can be advantageous as it allows the user greater freedom of movement with the capture device 102, 102a, 102b, which can be especially beneficial when trying to access certain anatomical locations. Also, the absence of a cord reduces the surface area available at the point-of-care on which bacteria and/or other unwanted microorganisms may bind and travel. In some embodiments, the capture device 102, 102a, 102b may be permanently cordless (i.e., no input port), and in other embodiments, the capture device 102, 102a, 102b may be configured to detachably receive an electronic connector, such as a power cord or a USB cord, or a permanently attached retracting cord may be provided. The computing device 116 may automatically transfer the captured data to the remote server computer 106 (e.g., over the network 140) at the moment the data is captured. In certain embodiments, however, the computing device 116 may not be in communication with the network 140; in such scenarios, the captured data may be temporarily stored in the volatile and/or non-volatile memory of the capture device 102, 102a, 102b for later transfer to the server computer 106.

The capture device 102, 102a, 102b may include additional features for enhancing data collection of the wound, such as one or more light sources 114 (e.g., a light emitting diode (LED), an incandescent light source, an ultraviolet light source, a flash etc.) for illuminating the wound before or during data capture, an indicator (not shown) configured to provide a visual and/or audio signal (e.g., images, text, lights, etc.) to the user, a thermal camera, a video camera, and/or one or more input/output devices (e.g., a microphone, a speaker, a port for communicating electrically with external components, such as a power source, the personal computing device 104, etc.). In some embodiments, the capture device 102 is configured for wireless charging, e.g., via a dock or cradle (not shown). In such embodiments, the charging cradle may also serve as an access point for the network 140. As discussed in greater detail below with reference to FIGS. 6A-6B, the capture device 102, 102a, 102b and/or image sensor 110 may also be configured to capture images of barcodes and/or QR codes displayed on the computing device 104, such as a barcode and/or a QR code that enable the capture device 102, 102a, 102b to connect to the network 140.

In some embodiments, the capture device 102, 102a, 102b may have other configurations than that shown in FIG. 1. For example, although the image sensor 110, depth sensor 112, and computing device 116 are shown as part of a single component and/or within the same housing, in other embodiments, any or all of the of the image sensor 110, the depth sensor 112, and the computing device 116 can be separate components. Likewise, in some embodiments, the capture device 102 does not include separate image and depth sensors, and instead includes a stereo camera that is configured to generate both image data and depth data. In other embodiments the capture device may include a displayless imaging device connected (by wired or wireless link) to a display device. Additional details regarding suitable capture devices 102 and methods of use can be found in U.S. Pat. No. 8,755,053, filed May 11, 2009 and U.S. Pat. No. 9,179,844, filed Nov. 27, 2012, both of which are incorporated herein by reference in their entireties.

As discussed above, the facility may include an interface module that generates graphical user interfaces (GUIs) to allow users to access the facility. The interface module also provides application programming interfaces (APIs) to enable communication and interfacing with the facility. APIs may be used by other applications, web portals, or distributed system components to use the system. For example, an application operating on a personal computing device may use an API to interface with system servers and receive capture data from the system. The API may utilize, for example, Representational State Transfer (REST) architecture and Simple Object Access Protocol (SOAP) protocols.

In some embodiments the capture device 102, 102a, 102b may include one or more further data gathering components, such as a positioning module (e.g. GPS), Inertial Measurement Unit, temperature sensor etc. Alternatively, such functions may in some embodiments be provided by a separate auxiliary module configured for attachment to the capture device 102, 102a, 102b.

Any of the capture devices 102, 102a, 102b and/or the personal computing devices 104 may provide access to video and/or audio communications, including video conferencing. Any of the capture devices 102, 102a, 102b and/or the personal computing devices 104 may provide access to remote medical expert systems. A remote medical expert may review or assess data captured by the capture device 102, 102a, 102b in real time, or at a later time.

The facility may provide for automated billing based on usage and/or data gathered by the capture devices 102, 102a, 102b. The facility may also maintain inventory information for capture devices 102, 102a, 102b.

The following methods may be implemented using appropriate facility software running on the capture device 102, 102a, 102b, personal computing device 104, and/or server computer 106 and/or further computing devices within the environment. In some embodiments, methods may be implemented through an application running on a capture device 102, 102a, 102b. Methods may be implemented across two or more devices and/or computers. For example, a method may include data capture steps implemented on a capture device 102, 102a, 102b, data analysis steps implemented on the capture device 102, 102a, 102b and/or personal computing device 104 and/or server computer 106, and data storage steps implemented on server computer 106 and persistent storage devices 108. In some embodiments, the personal computing device 104 may be omitted.

FIGS. 2 to 5B illustrate embodiments, which may be implemented by the facility executing within the environment. In these embodiments absolute scale data is not required to be captured. In these embodiments, no calibration of the device with respect to image scale is necessary.

Dimensions may be measured and/or compared in arbitrary units. "Arbitrary units" refers to units that do not necessarily reflect a true measurement of the surface or surface feature. Dimensions in arbitrary units may be normalized such that they can be compared to each other. "Absolute units" or "absolute dimensions" are used in this specification to refer to true units or dimensions, for example a wound length in millimeters or inches.

The data received by the facility is sufficient to monitor trends in wound healing; wound development; or wound composition (e.g. changes in tissue type, areas of particular tissue types etc). In further embodiments, described below, data captured without absolute scale data may be retrospectively calibrated. That is, calibration data may be captured at a later time and used to obtain scale data for the previously captured images.

Figure 2:
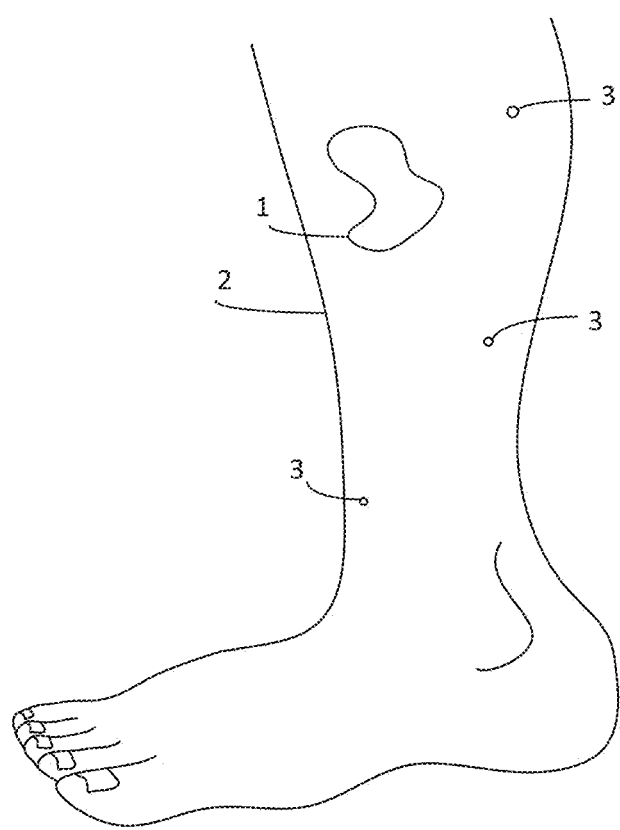
FIG. 2 shows a patient's leg, with a wound, ulcer, lesion or other surface feature of interest.

FIG. 2 shows an anatomical surface feature 1, such as a wound or ulcer, on the leg 2 of a patient. A user (e.g. a healthcare professional or caregiver) may capture an image of the patient's leg 2, including the wound 1, using the capture device 102, 102a, 102b (FIG. 1).

Dimensional information for the wound 1 may be obtained by analysis of the captured image. In the absence of any calibration or scale information the dimensional information obtained will be in arbitrary units, i.e. the dimensional information will not necessarily represent a true measurement of the ulcer. For example, analysis of the image may provide an ulcer length of 5 units, an ulcer width of 3 units and an ulcer area of 11.8 units squared (with the area being calculated by the well known Kundin method, i.e. length times width times Pi/4). Alternatively, area may be calculated by counting the number of pixels in the captured image that fall within the outline of the wound; or by any other suitable method.

The image data obtained may be stored in any suitable database and/or as part of any suitable electronic health record, together with the dimensional information, date information, patient identification information, wound or ulcer identification information (for patients with several wounds or ulcers), address details, billing information etc. Any of these data may be input by the user and/or retrieved from the database or other data store. The retention of this data allows comparison with data captured at a later time, and for trends in development or healing of the wound to be monitored over time.

Figure 3:
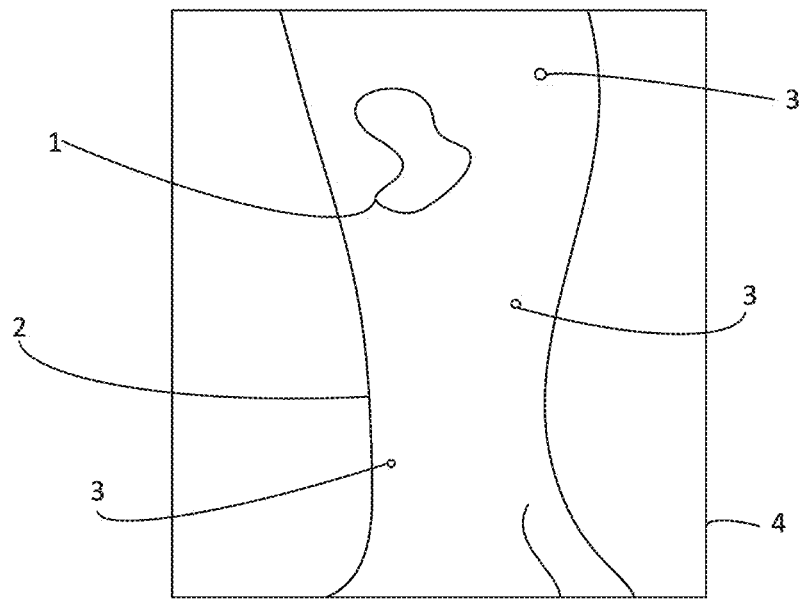
FIG. 3 shows a first image of the patient's leg of FIG. 2.

FIG. 3 shows a first image 4 of the patient's leg 2, including the wound 1. As shown in FIG. 3, the patient's leg may include a number of markings or other permanent or semi-permanent skin features 3, such as moles, freckles, birthmarks, skin wrinkles, creases, lines, tattoos (permanent or temporary tattoos), scars or the like. Such permanent or long-term, fixed points or markings on the patient's body may be termed "anatomical fiducials". In some embodiments, a permanent or semi-permanent marking may be added (using e.g. a pen, tattoo etc) in order to provide an anatomical fiducial. This may be done in addition to existing anatomical fiducials, or in a surface region where no or insufficient suitable anatomical fiducials are found.

Figure 3A:
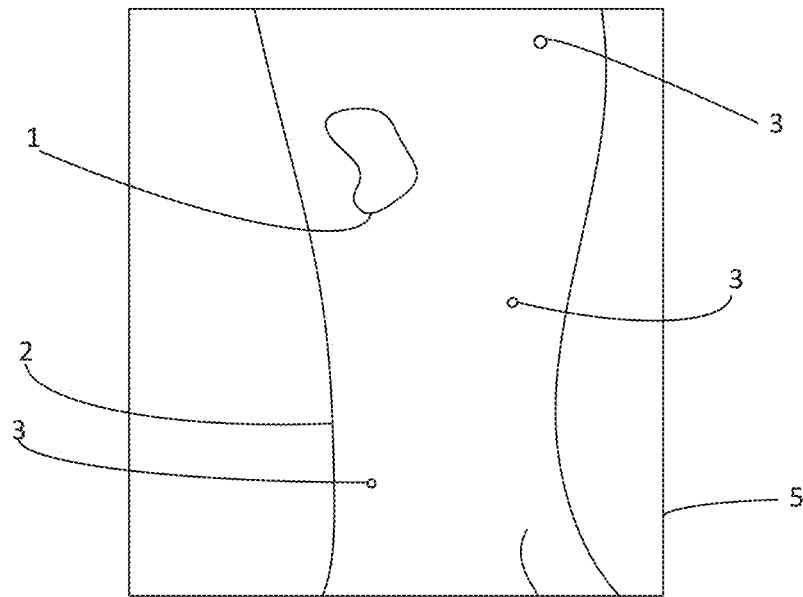
FIG. 3A shows a second image of the patient's leg of FIG. 2.

At a later time a user may capture a further image 5 of the patient's leg 2 including the wound 1 as shown in FIG. 3A, using the same or a different capture device 102, 102a, 102b. The second image 5 may have a different scale to the first image 4.

In order to compare the dimensions of the ulcer in the two images, a registration or scaling may be effected between the two images. That is, the second image, or dimensions measured in the second image, may be either be registered with or may be scaled into the units of the first image.

Scaling can be achieved by identifying points in the common image region of the first and second images, such as the outline of the patient's leg, bone structures and any anatomical fiducials 3, such as moles, freckles, birthmarks, skin wrinkles, creases, lines, tattoos, scars or the like. Once two or more such anatomical fiducials have been identified, a distance or distances between the anatomical fiducials can be measured in both images and a relative scale factor determined. In some embodiments, it may be advantageous to utilize three or more anatomical fiducials. This allows correction for variance in the angle of the captured device relative to the skin surface.

In another embodiment, a known registration process may be used to register one image to the other, such that each image has the same scale. However, in some embodiments the wound itself is not used as part of this registration, since it may have changed in size and shape between capture of the first image and the second image. However, in some cases certain features within an ulcer or other anatomical feature being monitored may be relatively constant in size or location and could be included in the registration process.

In some embodiments image transformations may be used to cater for different perspectives between images, different camera focal lengths or fields of view, different ranges between camera and skin surface etc.

Figure 3B:
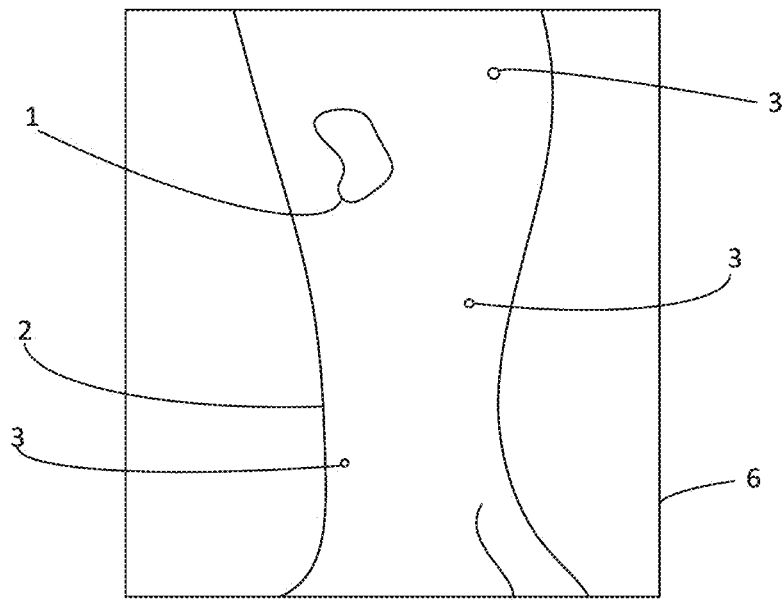
FIG. 3B shows a scaled version of the image of FIG. 3A.

FIG. 3B shows the image of FIG. 3A, scaled or registered to the scale of FIG. 3. Scaling of image data facilitates visual comparison between the images. However, in some embodiments dimensions may be determined directly from each image and subsequently scaled, i.e. the dimensional data may be scaled rather than the image data.

Figure 3C:
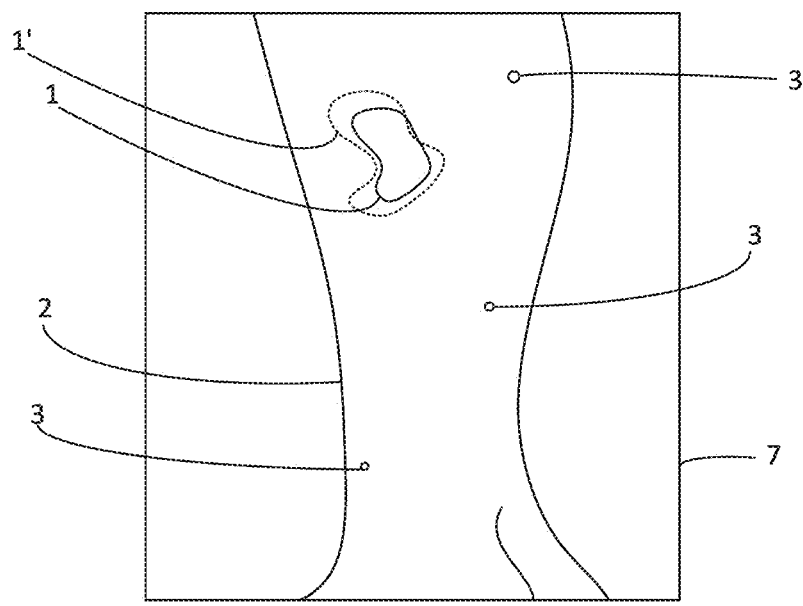
FIG. 3C shows a display with overlaid images.

FIG. 3C shows a display 7 with the images 3 and 3B overlaid. The size and shape of the wound 1, 1' at two different times can be seen. Again, this may facilitate visual comparison between images captured at different times, allowing a medical professional or other user to monitor changes in the shape or size of the skin feature 1.

Figure 3D:
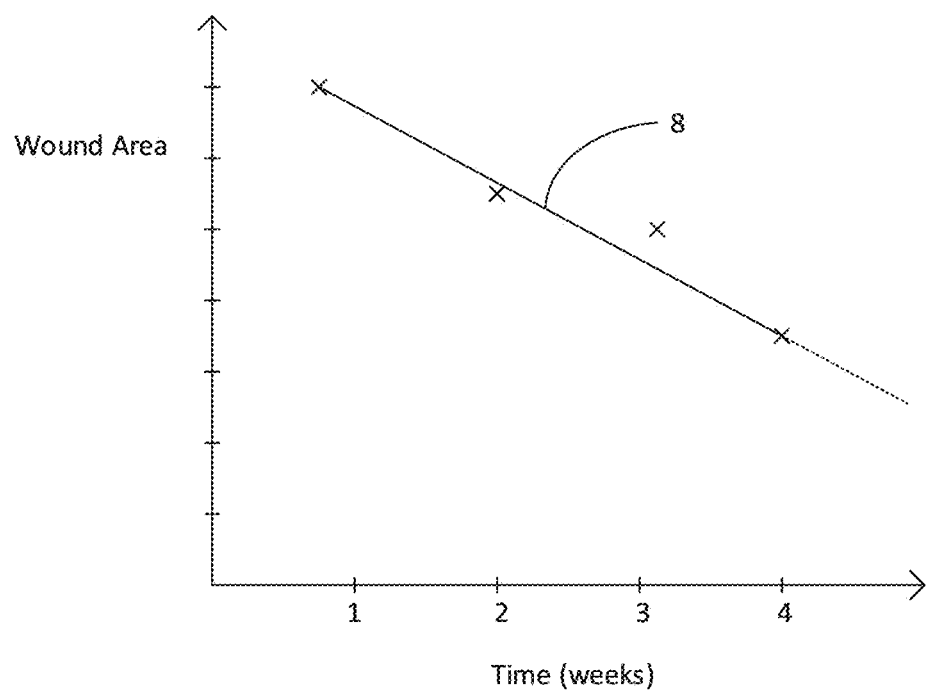
FIG. 3D shows a graph of the trend in ulcer area over time.

FIG. 3D shows a displayed graph of wound dimension (in this case area, measured in arbitrary or normalized units) against time. A curve or line 8 may be fitted to the gathered data points. The curve or line 8 may be extrapolated (as indicated by the dashed line) beyond the last data point to give an expected healing profile. If measured ulcer dimensions depart from the expected healing profile, an alert may be issued.

In another embodiment, the user may be guided to position the device at approximately the same range from the user's skin, and/or with a similar perspective to that of the first image. This will result in the scale of the second image being approximately the same as the scale of the first image. The images may be directly compared and dimensions may be read directly from the second image. This may be done by counting pixels where both images are captured by the same camera or by two cameras with the same or a similar millimeter per pixel scale factor. Alternatively, dimensions may be normalized or calculated as a fraction of total image height, width or other suitable dimension. Scaling or registration, as described above, may be performed if greater accuracy is desired. This method may be applied in the case of a second capture made using a camera that has the same or a different field of view than that of the camera that captured the first image.

Figure 4:
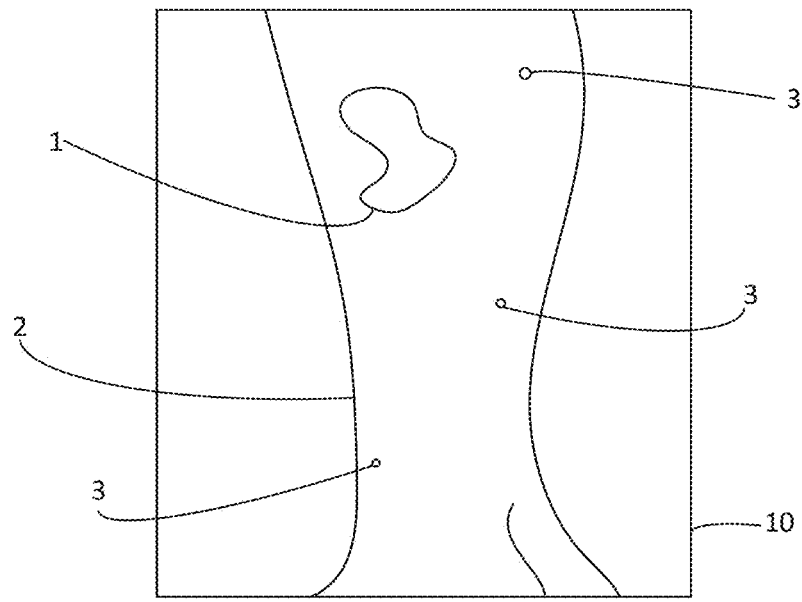
FIG. 4 shows a further image of the patient's leg of FIG. 2.

FIG. 4 shows an image 10 of a patient's leg 2 captured at a first time and including a skin feature 1. The image 10 may show anatomical fiducials 3, as discussed above.

Figure 4A:
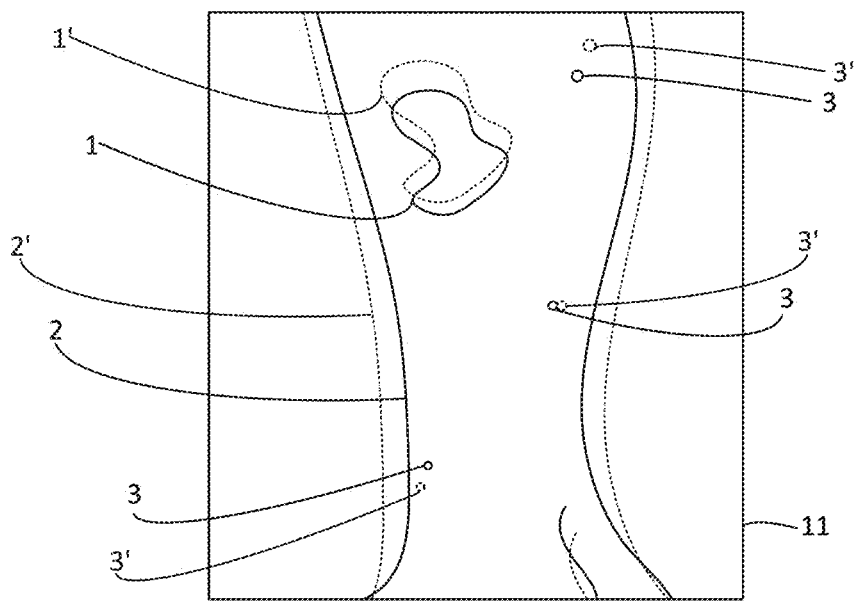
FIG. 4A shows a device display with a real-time camera feed and overlaid guide.
Figure 4B:
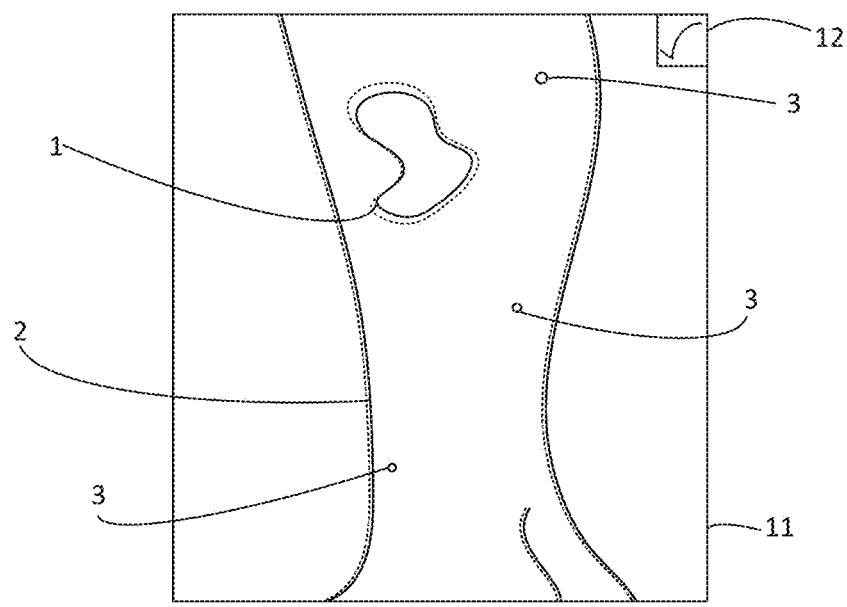
FIG. 4B is a further view of the display of FIG. 4A.

FIG. 4A shows a device display 11 at a later time. The display shows a real-time camera view (shown in solid line) and an overlaid guide (shown in dashed line). The overlaid guide may simply be an overlaid image of the skin surface captured previously (such as the image 10 of FIG. 4). FIG. 4A shows that the device is not properly positioned. The camera view is misaligned with the guide, having a different perspective and scale. A user may align the device with the desired position by moving it to bring the camera view into alignment with the guide, as shown in FIG. 4B. Correct alignment of the device may be determined by the user, by observing the alignment of camera view and overlaid guide. Alternatively, the device may detect the alignment of camera view and guide and when an acceptable level of alignment is reached provide feedback in the form of an audio, visual or audiovisual notification. For example, when acceptable alignment is achieved the device may beep. Or the quality of the alignment may be indicated, for example by the pitch, volume or other characteristic of the audio signal, to inform the user if he/she is moving the device in the right direction or otherwise. In the embodiment shown in FIG. 4B, a visual indicator 12 may be displayed when acceptable alignment is achieved.

In some embodiments the device may automatically capture data when an acceptable alignment is detected. In other embodiments the user may issue a data capture instruction (for example by pressing a button, touch screen etc., or by any other suitable user input).

In other embodiments, the guide may be one or more portions of a previously captured image of the patient's skin surface. For example, it may be desirable to remove the wound 1 from the guide image, since the shape of the wound 1 may change over time, so that using the wound 1 in the guide image may confuse the user. Similarly, the background (e.g. tables/beds/equipment etc visible in the image) may be eliminated from the guide image. Alternatively, the guide may comprise one or more guide masks or markings based on a previously captured image of the patient's skin surface. For example, guide markings may be generated based on the position of anatomical fiducials 3, or the outline of a user's limb, or positions of bone features etc. In still further embodiments, one or more guide masks or markings may be selected from a library of available guide masks or markings (e.g. a lower leg mask may be used, having a shape corresponding to the average lower leg).

Figure 5:
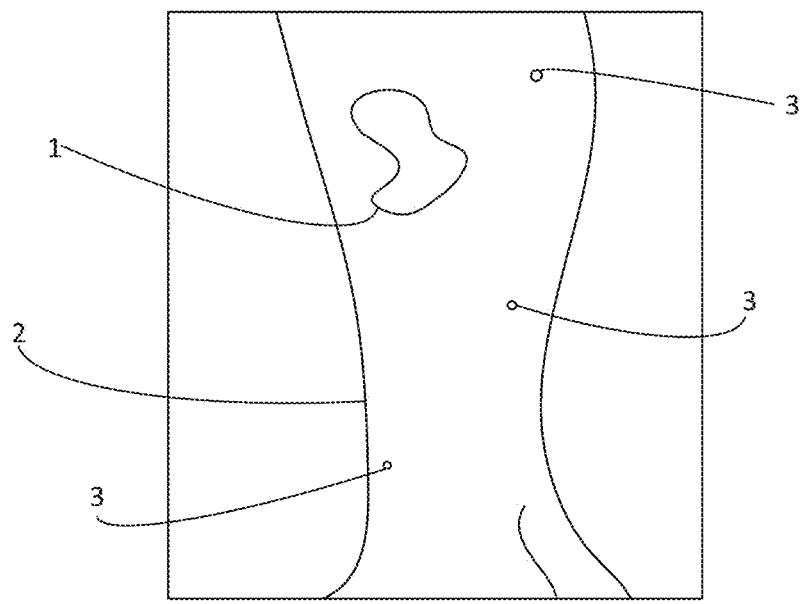
FIG. 5 shows a further image of the patient's leg of FIG. 2.
Figure 5A:
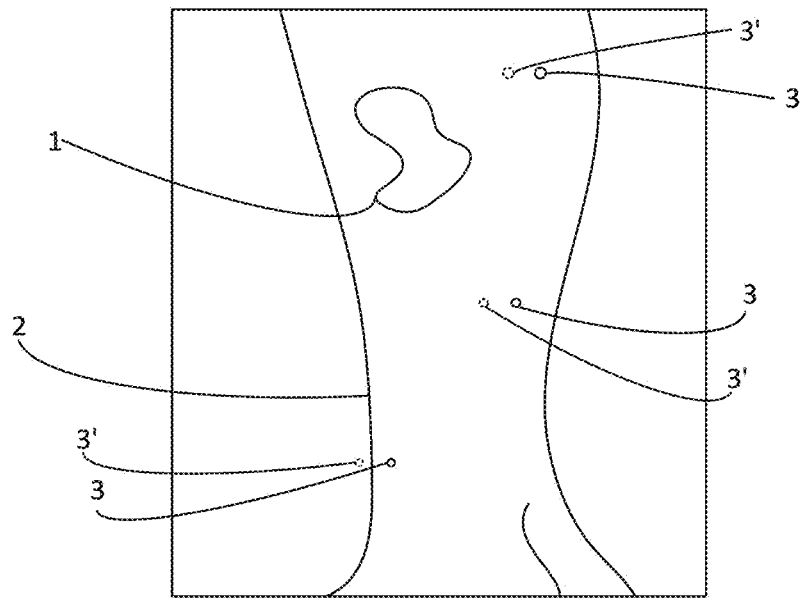
FIG. 5A shows a device display with a real-time camera feed and overlaid guide.
Figure 5B:
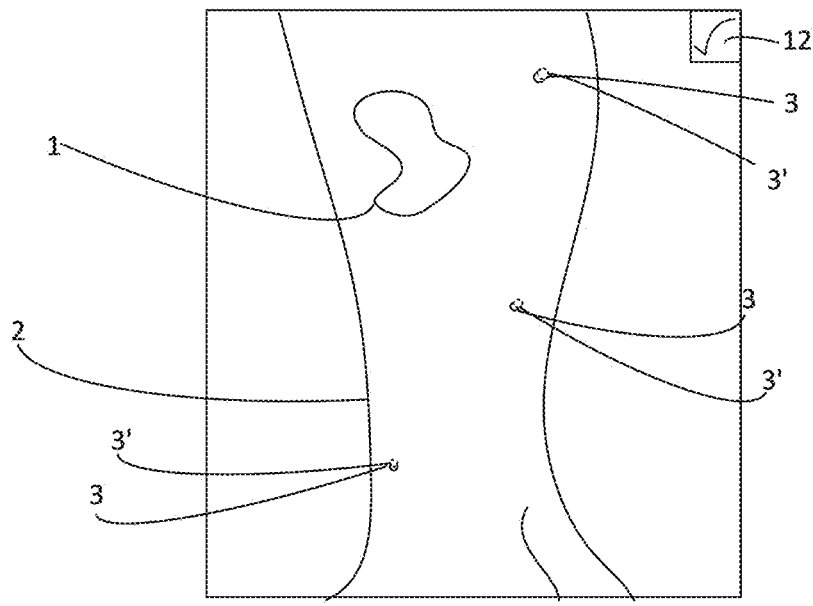
FIG. 5B is a further view of the display of FIG. 5A.

FIGS. 5A to 5B show an embodiment in which the guide has been generated from a previous image. However, in this embodiment the guide includes only three image portions or markings 3' corresponding to the anatomical fiducials 3. Anatomical fiducials may be selected by a user (or may be automatically identified) in the previous image for subsequent use in the guide image. In FIG. 5A the camera view and guide image portions or markings 3' are shown misaligned. The user may align the camera with a desired position by aligning the anatomical fiducials 3 in the real-time camera view with the guide image portions or markings 3', as shown in FIG. 5B.

In the methods of FIGS. 4 to 5B, the absolute scale is again not necessarily known. The image data is obtained at approximately the same scale in each case because the user is guided to position the device to deliver images with approximately the same scale. If further accuracy is required, scaling or registration can be performed as discussed above.

Further, at any time data obtained by any of the methods of FIGS. 3 to 5B can be processed to provide absolute dimensional information. This can be achieved by obtaining or inputting calibration data, and processing image or dimensional data already obtained and/or processing image or dimensional data for future measurements to provide absolute dimensional information or real scale information. This may be done, for example, in response to a health expert's determination that the surface feature requires further analysis.

Various forms of calibration information may be used. The calibration information can be obtained at any stage, at the beginning of treatment or a wound study, in the middle of treatment or wound study, or even after the wound is completely healed.

Estimated calibration data may include an expected dimension (such as an expected limb width, length or circumference etc). Estimated calibration data may be in the form of a manually entered user estimate of a dimension. The device may allow a user to select points on an image and enter an estimate of a distance between them. Alternatively, estimated calibration data may be automatically generated. The estimated calibration data may be a function of any suitable data in the patient's health record. For example, an estimated limb width, length or circumference may be generated based on the patient's gender, weight, height or any other suitable information.

Manually obtained calibration information may include measurements between anatomical fiducials made by a healthcare provider or other user. For example, the distances between anatomical fiducials may be measured using a ruler or tape measure, and manually input into the device or otherwise into the patient's electronic record. A dimension of a limb, e.g. a circumference, width or length of a limb, may be measured in a similar manner.

Figure 6:
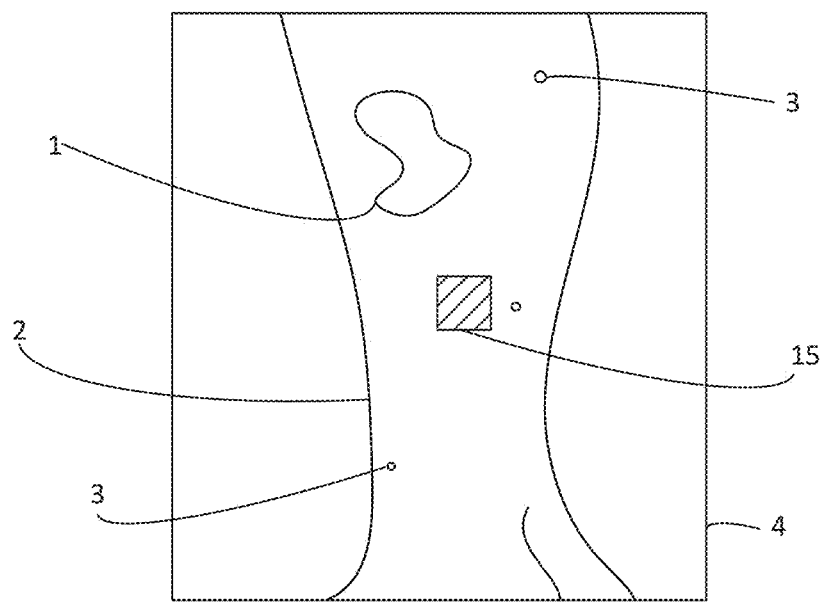
FIG. 6 shows an image of the patient's leg of FIG. 2, including a known-size fiducial.

However, some embodiments may rely on automated acquisition of calibration data. This may be obtained by any suitable method. For example, a calibration image may be taken of the patient's skin surface including a known user-supplied fiducial 15, as shown in FIG. 6. As the size of the fiducial 15 is known, the scale of the calibration image can be determined and absolute dimensions of the wound 1, or dimensions associated with anatomical fiducials, can be determined as required.

Alternatively, calibration data may be captured using a device capable of capturing absolute dimensional data, such as a 3D camera (e.g. stereoscopic camera, depth camera, a camera capable of measuring range such as a time-of-flight based device), or a structured light device. Suitable devices for gathering calibration data may be simple devices or may be auxiliary modules for attachment to a Smartphone, tablet or the like. For example, calibration data may be obtained using the Applicant's Silhouette device, or any of the suitable devices described in U.S. Pat. Nos. 8,755,053 and 9,179,844, the entire contents of which are incorporated by reference herein.

This has the advantage that calibration data can be gathered using a more complex device once, or for only a subset of data captures, with a simpler more ubiquitous device being used for other data captures. In some applications it may be desirable to gather calibration data at a medical facility, or for calibration data to be gathered by more skilled users such as medical professionals, using more capable devices. Other data can be gathered by less skilled users, possibly at remote locations, such as patient's homes, using more ubiquitous devices such as Smartphones, digital cameras, tablets etc. As noted above, the calibration data need not be the first data gathered as calibration can be performed retrospectively.

In further embodiments fully scaled or calibrated data may be gathered at each data capture. That is, each data set contains sufficient information for absolute dimensions of the surface feature to be determined without reference to additional calibration data. This may be achieved by manually entering user measurements with every data capture, using user-supplied known fiducials with every data capture, or by use of a device capable of capturing absolute dimensional data at every data capture, such as a 3D camera (e.g. stereoscopic camera, depth camera, a camera capable of measuring range such as a time-of-flight based device), or a structured light device. Suitable devices for gathering calibration data may be self-contained devices or may be auxiliary modules for attachment to a Smartphone, tablet or other capture device. For example, calibration data may be obtained using the Applicant's Silhouette device, or any of the suitable devices described in U.S. Pat. Nos. 8,755,053 and 9,179,844, the entire contents of which are incorporated by reference herein.

Where user supplied, known size fiducials are used, these may define not only a known size but also known optical properties. This not only provides a scale but also a means to match image properties (e.g. exposure and/or white balance) between different images (possibly captured by different devices) allowing those images to be consistently displayed and compared. In other embodiments image properties (e.g. exposure and/or white balance) may be corrected (or at least made consistent between different image captures) by analysis of skin tones etc. Further, the device may be arranged to issue alerts to the user if lighting is outside a desired range, such that captured images have unacceptable exposure or white balance.

User-supplied fiducials may also contain machine readable indicia, such as bar codes, QR codes, RFID elements or any other suitable indicia. Such machine readable indicia may encode any desired data, including patient identification information, date information, wound information, and/or user information (e.g. healthcare provider identification). Machine readable indicia may be read from image data captured by the capture device, for example by identifying and reading a QR code in the image. The image data may be the image data captured for analysis of the anatomical surface feature. Alternatively, further image data may be captured. Alternatively, the machine readable indicia may be read over any suitable wired or wireless link (e.g. Bluetooth or reading by an RFID reader). Machine readable indicia may allow other captured data or medical samples to be correctly associated with the patient or anatomical surface feature data. Machine readable indicia may also be used to ensure that supplies (e.g. the fiducials) are not being reused for different patients.

Consistent scale across displayed images is also desirable, since it allows meaningful comparisons to be made. Images may either be captured at a consistent scale, or may be scaled for consistent display, assessment and/or measurements.

In still further embodiments, scale or calibration information may be generated by one of the following methods, with every data capture or as a calibration to be applied to other data captures.

Selected Embodiments of Capture Devices for Use with the Facility

Figure 7:
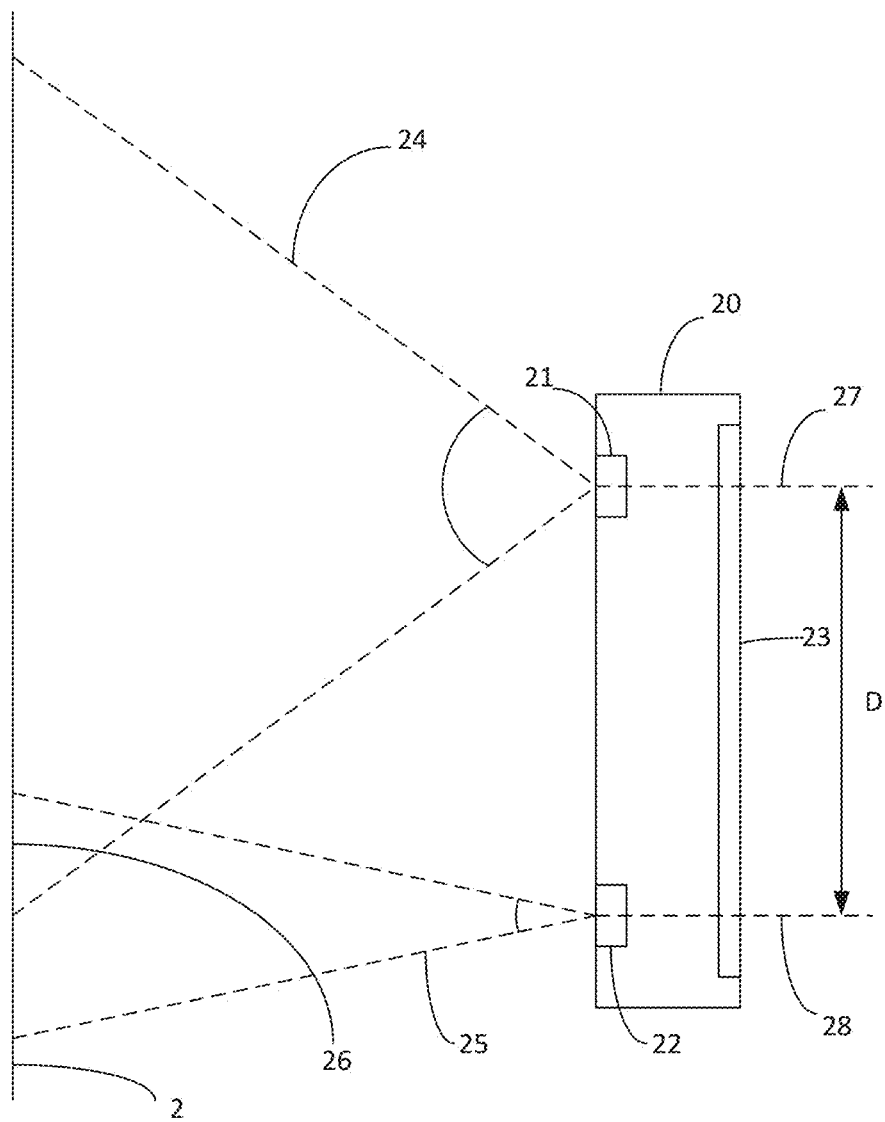
FIG. 7 shows a device including a main camera and an auxiliary camera.

FIGS. 7-14 show different embodiments of capture devices for use with the facility disclosed herein. In one embodiment a device with an inbuilt first camera having a first focal length, with a first field of view, and an inbuilt second camera having a second focal length, with a second field of view, may be used. For example, FIG. 7 shows a capture device 20 including a first camera 21 and a second camera 22. The device may also include a display 23, such as a touchscreen. The first camera 21 may be a wide angle or standard lens camera, while the second camera 22 may be a standard or telephoto lens camera. Image data may be captured of the skin surface, including the surface feature of interest, using the two cameras 21, 22. In particular, the capture device 20 may be arranged to capture data from both cameras simultaneously, or substantially simultaneously, in response to a single instruction from the user to capture data or in response to an automatic capture decision.

The field of view of the first camera 21 is indicated by dashed lines 24, while the field of view of the second camera 22 is indicated by dashed lines 25. As shown in FIG. 7, the two fields of view 24, 25 define a common image region 26 on the skin surface. As the distance D between the optical axes 27, 28 of the two cameras 21, 22 is known, the range or scale associated with the image can be determined by analysing points present in both images captured by the cameras 21, 22, within the common image region 26. This may be done using a triangulation process between a common object point and the corresponding image points from each camera, with knowledge of the lens focal lengths and image sensor characteristics such as pixel pitch or spacing etc. For autofocus cameras, the triangulation may also take into account the focal distance (to allow for lens movement). Once the range or scale is known, measurements may be made in relation to any point within either field of view 24, 25, including points outside the common image region 26.

Figure 8:
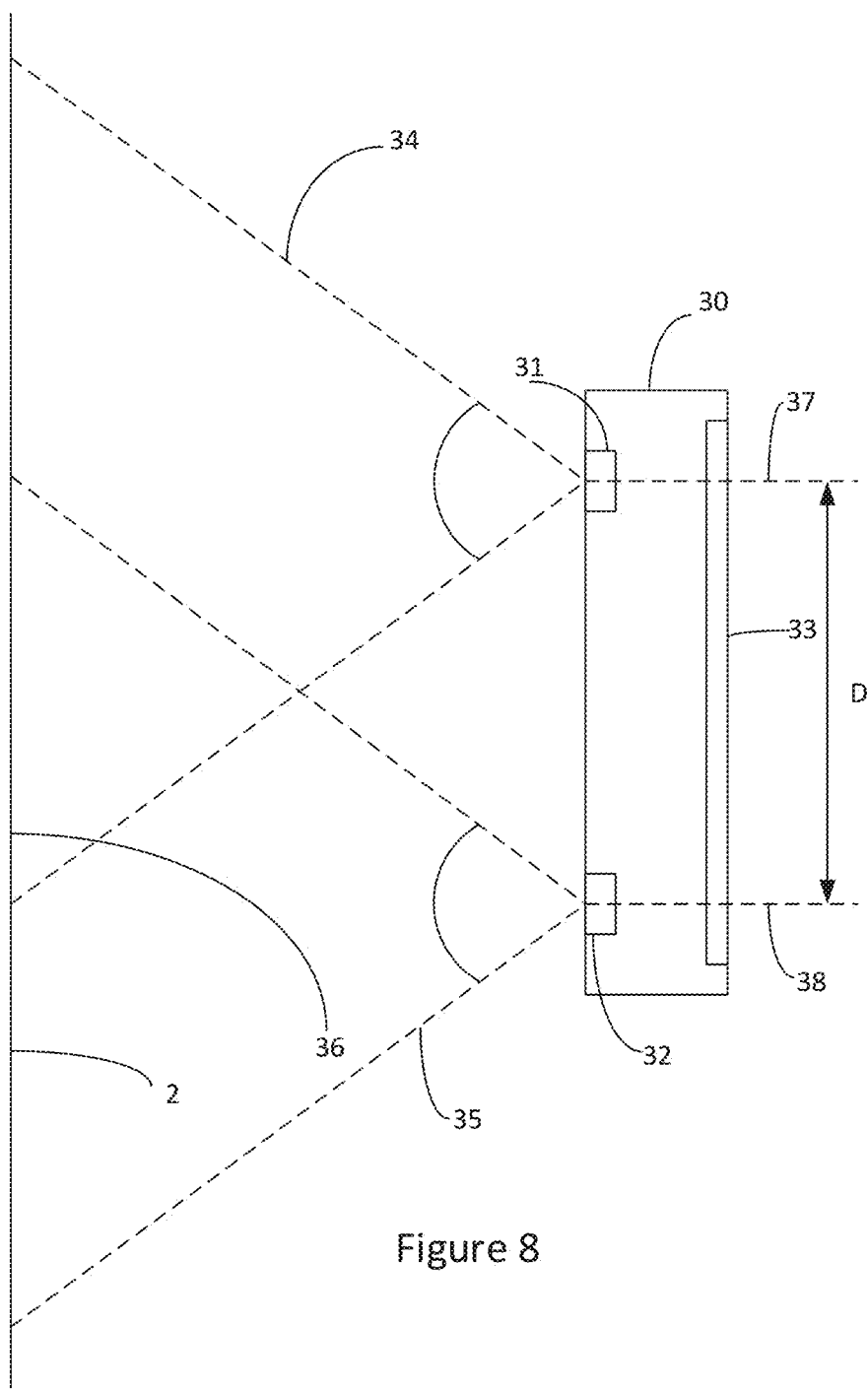
FIG. 8 shows a further device including a main camera and an auxiliary camera.

FIG. 8 shows another embodiment of a capture device 30. The capture device 30 includes a first camera 31 and a second camera 32. The capture device 30 may also include a display 33, such as a touchscreen. The first camera 31 may be a color (RGB) camera, while the second camera 22 may be a monochrome camera. In the embodiment shown the two cameras are of the same focal length and field of view 34, 35. However, that is not necessarily the case. Image data may be captured of the skin surface, including the surface feature of interest, using the two cameras 31, 32. In particular, the device 30 may be arranged to capture data from both cameras simultaneously, or substantially simultaneously, in response to a single instruction from the user to capture data.

The two fields of view 34, 35 define a common image region 36 on the skin surface. As the distance D between the optical axes 37, 38 of the two cameras 31, 32 is known, the range or scale associated with the image can be determined by analysing points present in both images captured by the cameras 31, 32, within the common image region 36. This may be done using a triangulation process between a common object point and the corresponding image points on the two camera sensors, with knowledge of the lens focal lengths and image sensor characteristics such as pixel pitch or spacing etc. For autofocus cameras, the triangulation may also take into account the focal distance (to allow for lens movement).

In general, any combination of cameras may be used, provided that they share a common image region. The common image region may not extend over the full field of view and the two cameras may not be identical. Cameras sensitive to different wavelengths may be employed. For example, one camera may be an RGB camera most sensitive in the visible spectral region while the second camera may be an infrared sensitive camera. In other embodiments two visible-sensitive cameras may be used. In some embodiments a separate camera module may be attached (e.g. clipped) to a device with one camera. The separate camera module may be a visible-sensitive or infrared sensitive camera.

Various devices are currently available including two cameras with a shared common image region, and more such devices are expected to become available. Suitable devices may include but are not limited to the following. The Huawei P9, which contains dual cameras, one monochrome and one color. In normal use the images are combined to form a single image. However, the cameras may be repurposed to perform the Applicant's methods. The LG G5 includes a 16 Mpix primary camera and an 8 Mpix wide angle camera. The Apple iPhone 7 plus includes two 12 Mpixel cameras, one with a 28 mm focal length lens and the other with a 56 mm focal length lens.

Figure 9:
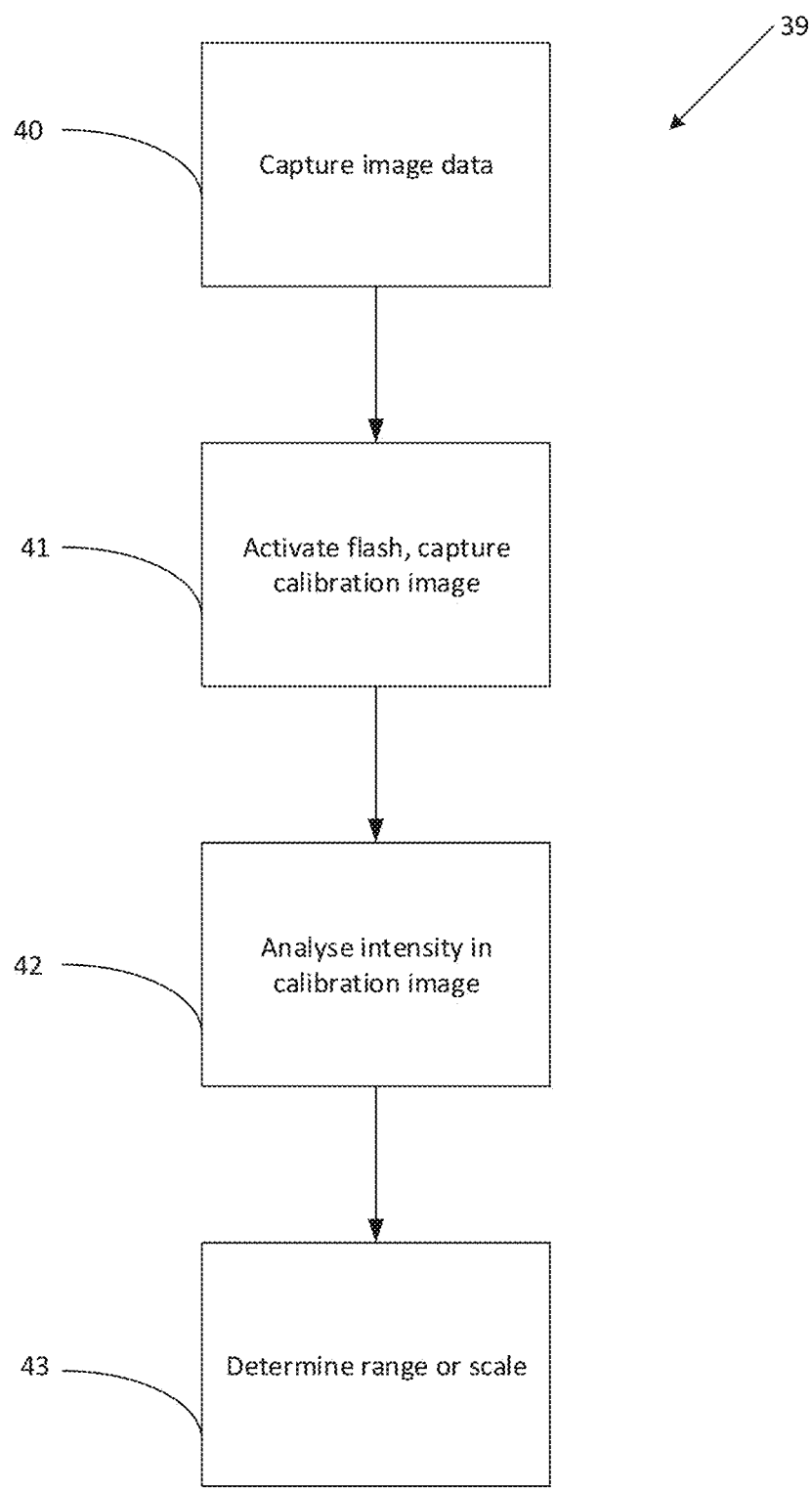
FIG. 9 is a flowchart depicting one measurement method.

Any of the capture device embodiments disclosed herein may include an inbuilt camera flash. FIG. 9 is a flow chart illustrating a method 39 (e.g., processed by the facility) in which range information is obtained using the capture device's inbuilt camera flash, flashlight, or other light source. The method 39 relies on detecting an intensity of light reflected from the skin surface and determining a range to the skin surface based on that intensity. In some embodiments known camera parameters (e.g. sensitivity, gain, aperture, exposure time etc) may be used as inputs to the range determination. At blocks 40 and 41 two related images are captured, in any order. One image captured in block 40 is a simple color (or monochrome) image of the skin surface including the surface feature of interest. Another image captured at block 41 is a calibration image. In some embodiments only the calibration image need be captured. In further embodiments two or more such calibration images may be captured in each data capture.

The calibration image is captured with the camera flash activated. In some devices the flash may be controlled to deliver a known power. In other devices the flash may have a fixed, known power output. The intensity of reflected light in the calibration image may be analysed at blocks 42, 43 to provide range information. For example, if the reflectance of the skin surface is known the image brightness will fall off with increasing range between camera and skin surface. By analysis of the image brightness, the range can be determined, if the skin surface reflectance is known. In some embodiments the wound area may be excluded from this range calculation, since its reflectance may vary depending on wound condition/healing etc.

The reflectance of the surface will depend on skin tone, color etc. However, the expected reflectance may be determined by reference to a lookup table or similar data store, optionally in combination with information on the patient's skin tone (which may be retrieved from memory) and/or color obtained from the image data itself. Further, the device itself may be calibrated by measuring flash reflectance from a standard surface, such as a photographer's standard gray card or the like. The patient's skin tone or skin reflectance may be calibrated, for example by capturing a calibration image including the skin surface and a standard calibration surface (such as a photographer's standard gray card or the like). Once calibrated the calibration surface may not be needed in later images.

A further image may be captured without the flash. This image may be used to compensate for illumination by ambient light. This allows the image brightness due to the flash to be isolated, giving greater accuracy in the range calculation.

In further embodiments an auxiliary device may be added over the capture device's flash, flashlight or other light source. For example, a lens, mask, grating etc may be attached over the flash, flashlight or other light source in order to project a desired pattern onto the surface. The pattern formed on the surface may vary with range. A user may be guided by the pattern to position the capture device at a desired range and/or position and/or orientation from the surface. Alternatively, the pattern may be included in one or more captured images and the range determined from the captured images.

Figure 10:
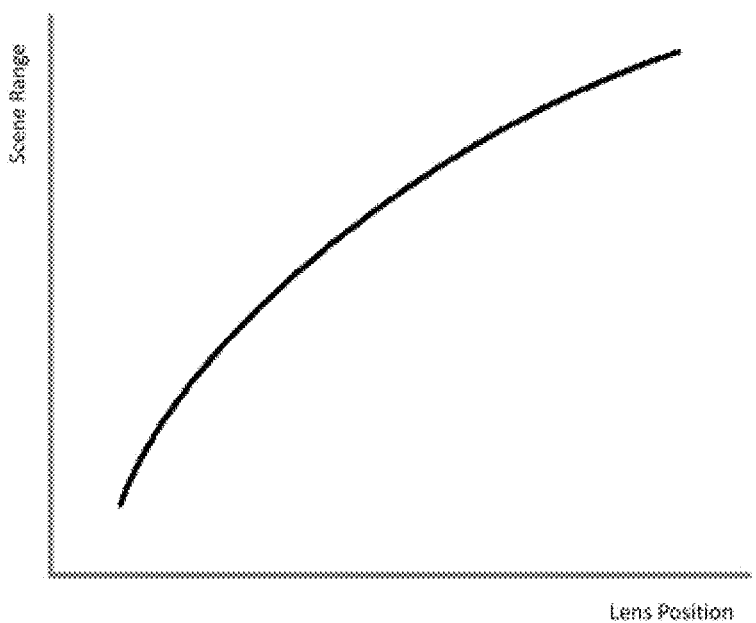
FIG. 10 is a graph showing the relationship between focal distance and lens position for one device.
Figure 11A:
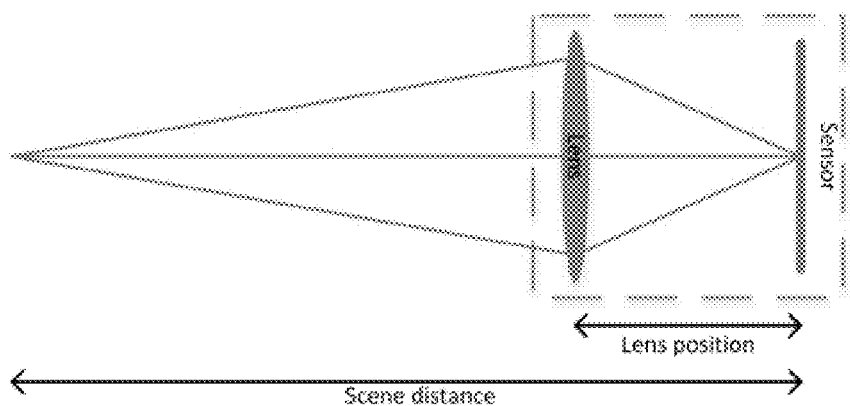
FIGS. 11A and 11B depict lens movement with focal distance.
Figure 11B:
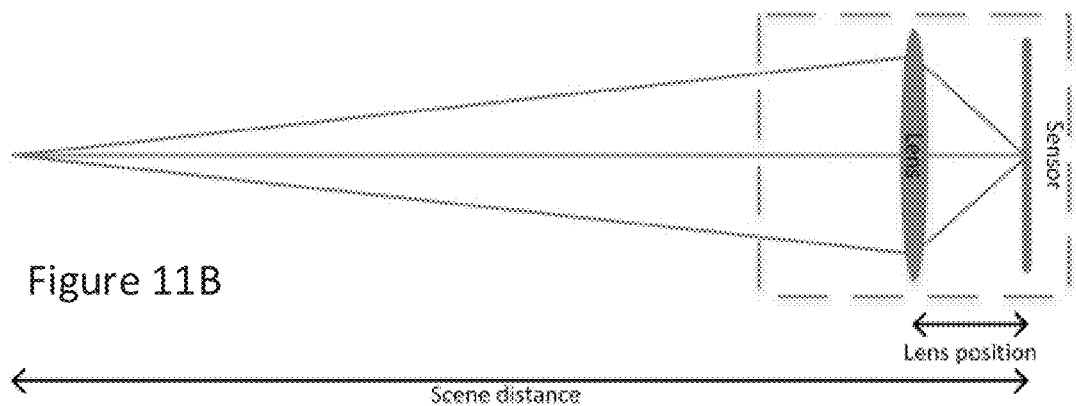
Figure 12:
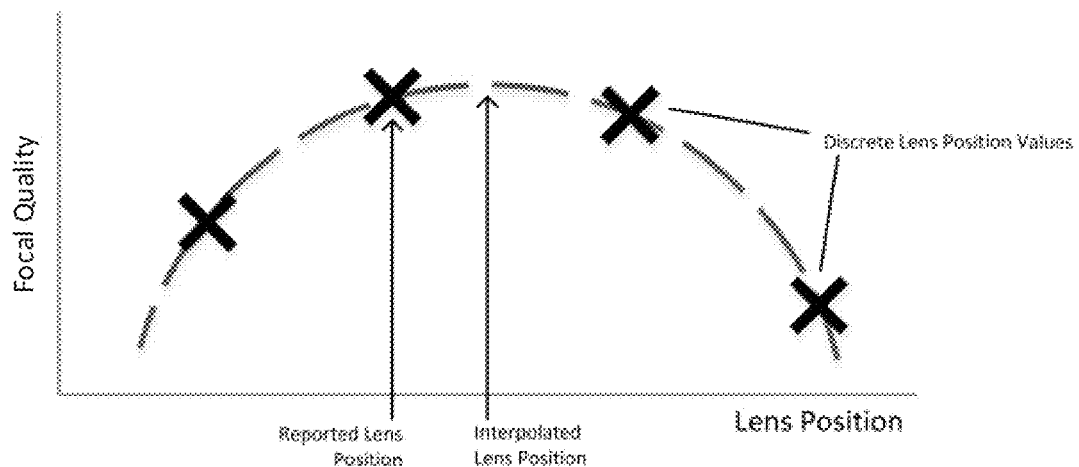
FIG. 12 illustrates an improved method of determining focal distance.

A further embodiment of a capture device is illustrated in FIGS. 10 to 12. Traditional camera imaging geometry does not allow the distance between scene points to be measured. However, if the distance from the camera to the scene (i.e. range) is also known, the distance between the two scene points can be calculated via triangle formulae, with knowledge of the lens focal length and image sensor characteristics such as pixel pitch or spacing etc (which may be obtained from the camera design specifications, or from a separate calibration procedure).

In the embodiment of FIGS. 10 to 12, the camera-scene distance (or range) is determined from focal information obtained from the camera lens. This embodiment relies on the use of a camera with an autofocus lens for which focal distance or lens position information is accessible. The lens focal distance or lens position is an output of the camera hardware/software, typically accessible via the device vendor's API. Some cameras output focal distance directly. Others output a lens position.

The scaling and range of the value retrieved is determined by the device vendor, for example the current Apple iOS API provides the lens position as a normalised value between 0 and 1, with 0 representing 'very close' and 1 representing 'very far', perhaps infinity. In any case, for many devices it is possible to perform a calibration of the camera to produce a lens position to distance map (parametric model or look up table) such as that shown in FIG. 10. Alternatively, such a map may be available from device vendors.

FIGS. 11A and 11B illustrate the adjustment of the lens position based on focal distance.

In this embodiment, the camera auto-focus is enabled. Image data may then be captured together with a lens position. The lens position may be converted to a distance measurement in absolute units (e.g. mm) using the aforementioned calibration data.

If the camera lens also provides an optical zoom function, the position of the optical zoom may also form part of the calibration process. Similarly, measurement processes may record the position of the optical zoom at time of capture to form part of the lookup into the calibration information.

In some capture devices the relationship between the lens position and scene range may be temperature dependent. This may be corrected by a suitable calibration process and gathering temperature correction data at the time of data capture. Similarly, calibration and/or correction may be performed to cater for any other factors influencing the relationship between lens position and scene range. In some embodiments a smartphone or tablet device or other capture device is utilized which contains a temperature sensor. In other embodiments, a temperature sensor attachment to the smartphone or tablet or other capture device may be used.

The estimation of scene range from lens position only gives a single distance from the camera to the plane of best focus; this plane is parallel to the camera sensor. Therefore, any measurements made from the resulting scaled image are most accurate if the points of interest are on this plane of best focus. If they are not, an error will be introduced. However, for typical imaging distances in measurement of a patient's skin surface, this error may be acceptably small.

In another embodiment the accuracy of the focal distance information obtained from the lens may be improved as follows.

In some capture devices the physical lens position may be restricted to a series of pre-defined (quantized) values, typical of a digital-to-analog converter or step actuator used to position the lens. By extension this also implies the focal distance or range (and therefore the final measurement) will also be quantized. By capturing a series of images at lens positions neighbouring the point of best focus, interpolation may be used to produce a non-quantized (and more accurate) result.

This approach requires the lens position to be 'driven' to a range of set values and a frame captured for each. From each of these frames a 'focal quality metric' is calculated. The focal quality metric may, for example, be the image contrast (variance) or some other sharpness parameter that may be determined from the image data.

Once a focal quality metric has been determined for each of a number of lens positions, a curve can be fitted to those points. This could be performed with as few as three frames by, for example, fitting a quadratic that would allow the point of peak focal quality to be determined, as illustrated in FIG. 12. Here the peak focal quality is higher than any of the data points and lies between two of the possible quantised lens positions.

In this embodiment the lens position determined by the camera's auto focus may be used as the starting point. The lens and camera may then be controlled to capture a number, N, of frames at different lens positions around that initial auto focus lens position. For example, the camera may be driven to move the lens −N steps, where N is a 'sensible amount' of motion determined for each model of smart device. The camera may then be driven through (2N+1) lens positions, with a frame captured at each lens position. This provides N lens positions below the auto focus lens position, the auto focus lens position itself and N lens positions above the auto focus lens position.

A curve, such as a quadratic or any other suitable curve, can then be fitted to the data points to determine the lens position or focal distance associated with the point of peak focal quality, which will correspond to the range from camera to object surface (i.e. patient's skin surface).

This process can be expanded to any suitable number of frames being captured. The number of steps or frames is chosen so that the data obtained lies on steep parts of the focal quality curve, close to the point of peak focal quality. Points further away may tend to reduce the accuracy of the fit. Using only a small number of points too close to the point of peak focal quality may also reduce accuracy of the fit. Further, by analysing a number of lens positions, this method is less susceptible to errors caused by improper camera autofocus, e.g. if the camera is not focused on the wound or skin surface.

The camera's auto-exposure algorithm may be controlled (bypassed) to use the smallest f/number (largest aperture) available. This gives the smallest depth of focus and greatest sensitivity of the focal quality metric to changes in lens position.

Further, the field of view (FOV) as well as the focal quality metric may change with lens position. Measurement of the FOV (whether it is fixed or changes with lens position) may provide information that complements the focal quality data. The field of view may be determined by analysis of the image data, for example by identifying the change in separation of image features in the multiple frames. Alternatively, a known size fiducial may be used.

Further, if this process is performed individually for points or sub-regions of the image it may be possible to determine a distance for a plurality of sub-regions. Together these would form a partial 3D scene mapping, i.e. image data plus distance data for each sub-region within the image. While not fully sampled 3D (i.e. depth information is not obtained for every pixel), this provides a choice as to which sub-region may be used for determination of range. For example, a sub-region corresponding to the healthy skin surface may be selected for determination of range. A sub-region corresponding to the wound may be excluded.

Further, obtaining distance data for a plurality of sub-regions may allow correction for the angle of the device relative to the surface. It may also allow a simply anatomical model to be fitted to the surface. For example, where distance data for several sub-regions are obtained, this may allow a plane or a cylindrical model approximating a leg surface to be fitted.

The range information obtained from the camera focal system, or by any of the other range-determination methods described herein, can be used to scale images. The range information may be used to determine relative scale factors between images. It may also be used simply to provide absolute dimensions from each image. Further, the range information may be used as an input to any suitable registration process, for registering images to each other.

The range information obtained from the camera focal system, or by any of the other range-determination methods described herein, may also be used to provide real-time feedback to the user to guide the user to a preset range. That is, the device may issue a visual or audio feedback to the user to guide the user to position the device closer or further from the surface until the distance between device and surface is within an acceptable or optimum range, or at a desired distance. The visual feedback may be in the form of any suitable guide, including a graphic, or a guide pattern generated on the display so as to overlay the image from the camera. In one embodiment the guide may include a number of lines that cross at a single crossing point when the distance is optimised.

Figure 13:
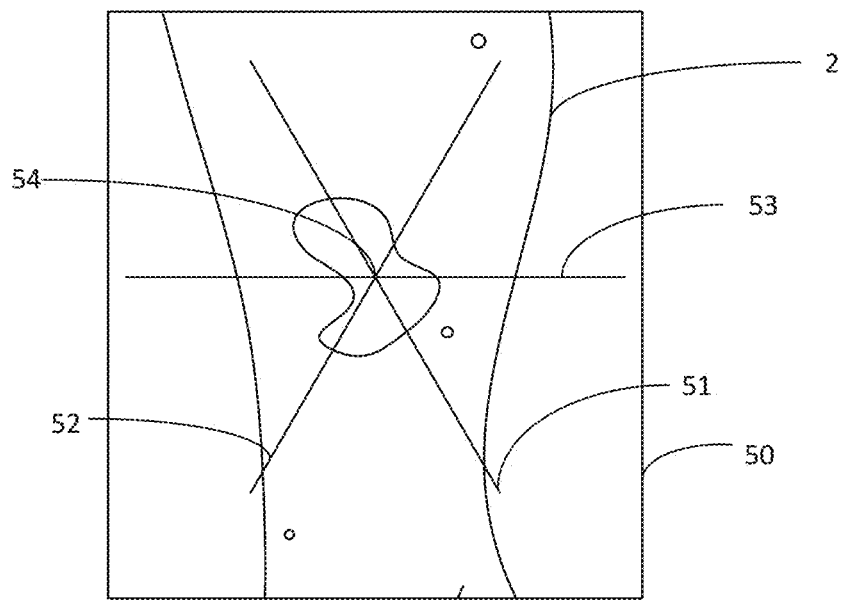
FIG. 13 shows a device display with real-time camera feed and overlaid guide, at a desired range.

FIG. 13 shows a device display 50 showing a real-time camera view of a patient's limb 2. Three guide lines 51, 52, 53 form a star pattern, with the three lines crossing at a single crossing point 54. This indicates that the range is correct and the user may capture data at that optimum range by pressing button, touching a touch screen or issuing some other suitable user capture instruction.

Figure 13A:
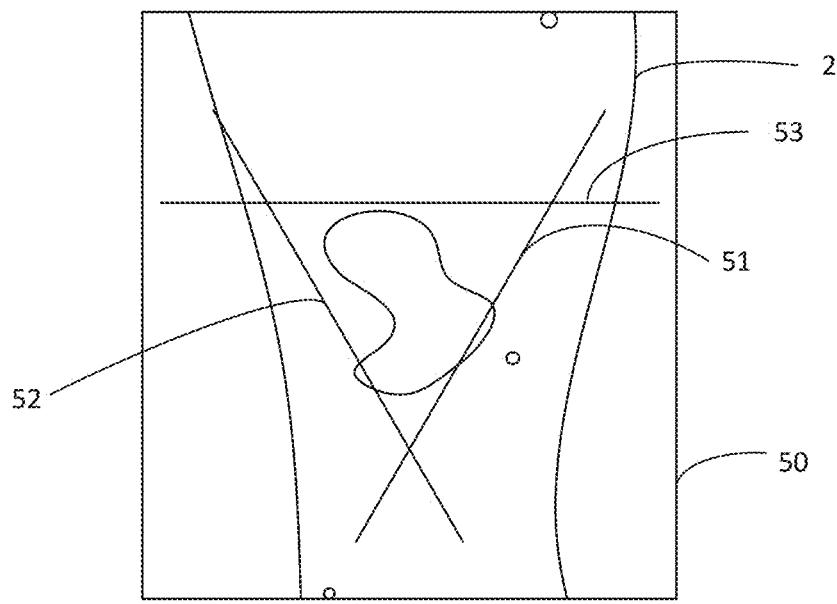
FIG. 13A shows the display of FIG. 13, at a closer range.

FIG. 13A shows the same device display 50 where the device is further away from the patient's skin than the optimum distance. Here the three guide lines 51, 52, 53 form a triangle, i.e. they do not meet at a single point. As the user moves the device towards the skin the triangle will reduce in size, with the guide lines 51, 52, 53 moving closer until they meet as in FIG. 13, when the distance is optimised.

Figure 13B:
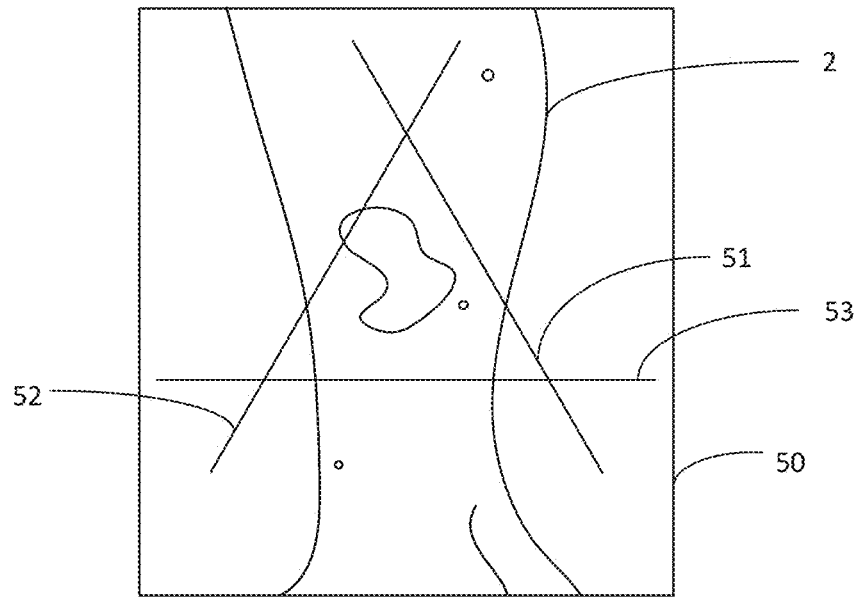
FIG. 13B shows the display of FIG. 13, at a farther range.

FIG. 13B shows the same device display 50 where the device is closer to the patient's skin than the optimum distance. Here the three guide lines 51, 52, 53 form a triangle, i.e. they do not meet at a single point. The triangle in this figure is inverted when compared to the triangle of FIG. 13A. As the user moves the device away from the skin the triangle will reduce in size, with the guide lines 51, 52, 53 moving closer until they meet as in FIG. 13, when the distance is optimised.

In other embodiments a different number of guide lines may be used. For example, four lines could be used, forming a square or rectangle, or five lines could be used forming a pentagon. However, in some embodiments the polygon will diminish in size as the optimum range is approached, with all lines crossing at a single point at the optimum range.

In still further embodiments different kinds of visual indicator, such as red and green lights or symbols, may be displayed to indicate to the user how to move the device towards an optimum range. A sliding indicator on a scale could be used to show the current range and the desired or optimum range. A circular indicator or gauge could be used, showing the current range and the desired or optimum range. An audio indicator could be used. For example, the device may beep when within some tolerance of the desired or optimum range. Alternatively, a variable tone or volume sound could be emitted to guide the user to move the camera closer to, or away from, the patient, with the sound, tone or volume determined by the range.

Further, the device may be configured to automatically capture data when the user has positioned the device at the optimum range. This may allow data to be captured without requiring a button or touchscreen to be pushed or touched, reducing camera shake.

In further embodiments the device may capture video data over a time period while the user moves the device through a range of positions and/or orientations and/or ranges. The user may be guided in the required movement of the device. The capture device may automatically select and/or retain video frames when an acceptable alignment and/or range is detected.

Many portable devices, including Smartphones and tablets, include a number of accelerometers and/or magnetometers and/or gyroscopes and/or other sensors, which together can be considered an "Inertial Measurement Unit" or IMU (also known as an Attitude and Heading Reference System (AHRS)). In some fields an AHRS may be considered to include an IMU and a processor. In some fields an IMU may be considered not to include a magnetometer. However, for the purposes of this specification the term IMU is to include all such IMUs (with or without magnetometers, and with or without processors) and AHRSs.

The IMU is capable of tracking movement of the device. In another embodiment the Applicant uses the device's IMU to track device movements while capturing two or more images of the skin surface from different positions. As the position of the device for each image is known from the IMU, or at least the relative changes in position between data captures, a baseline between capture positions is known. The IMU also allows changes in orientation to be determined and an appropriate correction applied. This allows depth, distance or scale information to be determined based on the images from the two positions, in a similar manner to that in which such information can be determined from images from two fixed cameras (as described above in relation to FIGS. 6 and 7). Here the two images are captured sequentially by the same camera in different positions, rather than by two separate cameras. However, once the relative positions are known, the analysis is similar.

In some embodiments the two or more images may be captured by capturing a video stream as the device is moved. Alternatively, a number of fixed image frame may be captured over a period of time. In some embodiments the required images may be captured all in response to a single user data capture instruction.

In some embodiments a small movement of the device may be sufficient to provide acceptable accuracy. Movement of the handheld device as the user attempts to hold it still will naturally occur. In some embodiments this movement alone may be sufficient to provide acceptable accuracy. In that case the user may simply be instructed to hold the device still. If greater accuracy is required, the user may be instructed to move the device.

In further embodiments the user may move the device back and forth. This back and forth, or oscillating, motion ensures that at some point the velocity of the device is zero. Further, movement of the device back to the starting point (as determined e.g. by image analysis) provides knowledge that the total accumulated translation of the device is zero. One or more of these factors can be used to correct for IMU drift.

Registration between the image data captured from the two positions may be performed based on skin features (as discussed above). In addition, since these images are captured sequentially over a very short time period, the skin feature of interest (ulcer, wound etc, especially the boundary of the skin feature) will not change over the data capture period and may be used as an input to the registration process.

In other embodiments, a sequence of frames may be captured, together defining a panoramic data capture. For example, such a method may be used for measurement of long or large surface features, or for features that extend around the circumference of the patient's limb. Guide information may be overlaid on the display to assist the user to move the device in the correct manner during capture of such a sequence of frames, maintaining an acceptable device orientation and/or range. The images may be registered or "stitched" based on the image data itself. In some embodiments, data from the IMU may assist in this registration or stitching.

In further embodiments, simultaneous localization and mapping (SLAM) methods may be used to map the skin surface based on several images captured by the capture device from different positions. This may be done based on the image data alone, or in some embodiments the image data may be combined with the tracking of the device position by the IMU.

In some embodiments auxiliary modules or devices may be used. These may attach physically to any of the capture devices described above, including to suitable Smartphones, tablets, computers etc. The attachment may be formed in any suitable manner, including for example a partial sleeve that allows the auxiliary device to mount to different capture devices. Alternatively, auxiliary devices may be integrated into Smartphone cases.

Suitable auxiliary devices include structured light devices (projecting one or more spots, stripes, fan beams etc produced by appropriate laser devices or a pattern generator), guide devices (e.g. projecting a laser or other light pattern to guide the user to position the device at a desired range and/or position and/or orientation with respect to the skin surface) cameras, stereoscopic cameras, and image splitters (described further below). Further auxiliary devices include sonar, ultrasound, infrared, ISM band miniature radar, or time-of-flight range finder modules (described in further detail below with reference to FIGS. 15A and 15B). An auxiliary device may include one or more further sensors (e.g. light sensors, reflectance sensors, temperature sensors), light sources, distance sensors, further cameras, or code readers (e.g. RFID readers, barcode scanners etc) etc.

An auxiliary device may be battery powered, or may be powered from an external power source. Where the auxiliary device requires power from an external source, this may be provided by a wired connection to the device's headphone jack. Further, control signals can be sent over a wired connection between the device's headphone jack and the auxiliary device, using the device's standard interface for transmitting audio signals through that jack. In other embodiments a wired connection may be made to any other suitable jack or connector on the capture device (e.g. Lightning connector).

Alternatively, control signals may be sent over any other suitable wired or wireless connection, including e.g. Bluetooth.

Where a structured light auxiliary device is used, this may be a very simple device providing range or scale information. That is, the structured light information may be used merely to determine a scale. A full model of the surface, as provided by more complex structured light devices may not be required in some applications.

In still further embodiments, a known size user-supplied fiducial may be used. By placing this fiducial in any image, the scale can be determined. This fiducial may be any small known object. As noted above, user-supplied fiducials may include encoded information, which may be read by the capture device or any other suitable reader.

Figure 14:
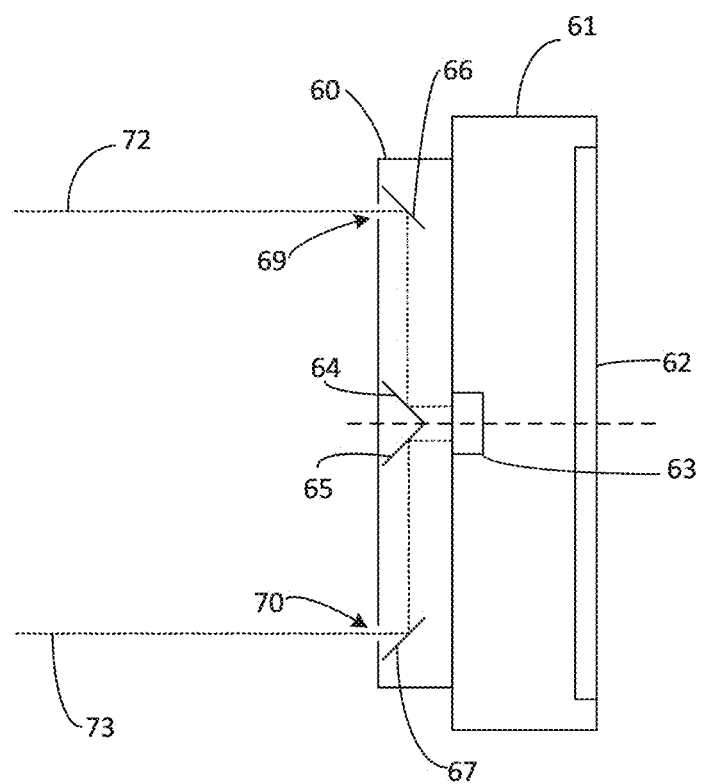
FIG. 14 shows an image splitter mounted on a portable device.

FIG. 14 shows, in schematic form, an image splitter 60 attached to a device 61. The device may have a display 62 and a camera 63. The image splitter 60 may have a pair of reflectors 64, 65 (e.g. mirrors or prisms) and a second pair of reflectors 66, 67 mounted in a housing 68, which is arranged for attachment to the device 61. A pair of windows 69, 70 are formed in the housing 68. The reflectors act to form two separated light paths 72, 73. One light path 72 extends through one window 69 and is redirected by reflectors 66, 64 before entering camera 63. The other light path 73 is an opposite path, extending through the second window 70 and being redirected by reflectors 67, 65 before entering the camera 63. This allows a baseline to be established between two optical paths. Each optical path will have its own field of view, and as the two fields of view overlap, the image data captured through this splitter allows a range to an object surface to be determined.

Such devices are available for SLR cameras (for example the Loreo Stereo Lens available from 3Dstereo.com, Inc). Similar devices may be made for fitting to any suitable capture device.

Further embodiments, operating within the facility, in which a user is guided to position the device at a desired range or position (including lateral position) for data capture will now be described. In these embodiments a guide is projected onto the surface, and the user moves the device to achieve a desired alignment of the guide with the surface or with the patient's anatomy. The Applicant's U.S. Pat. No. 9,179,844, the entire contents of which are incorporated by reference herein, discloses a projected guide consisting of a number of laser lines, and such an arrangement may be used in devices disclosed herein. For example, an auxiliary unit including laser fan beam generators may be attached to a Smartphone or other device.

However, in some embodiments of the current application, the projected guide is used solely as a positioning aid which assists the user to position the device at a desired range, thereby setting a scale associated with the resulting image. In these embodiments the structured light is either not present in captured data (e.g. it may be switched off for data capture) or is not analysed to provide scale information.

In other embodiments a guide based on an earlier captured image may be projected onto the surface. In a similar manner to other embodiments in which a guide is overlaid on a device display, the projected guide may guide the user to position the device at a desired range and/or perspective. The projected guide may guide the user to position the device at the same range from the user's skin, and/or with a similar perspective to that of a previously captured image. This will result in the scale of the second image being approximately the same as the scale of the previous image. The images may be directly compared and dimensions may be read directly from the second image, provided the cameras used for each data capture are the same or have similar characteristics. Alternatively, captured data may include camera parameters, which can subsequently be used in scaling to a common or normalized scale. Scaling or registration, as described above, may be performed if greater accuracy is desired.

The projected guide may simply be an image of the skin surface captured previously. A user may align the device with the desired position and/or range by moving it to bring the projected guide into alignment with the patient's anatomy. Correct alignment of the device may be determined by the user, simply by observing the alignment of the guide and the patient's anatomy. Alternatively, the device may detect the alignment of anatomy (as viewed through the camera) and guide and when an acceptable level of alignment is reached provide feedback in the form of an audio, visual or audiovisual notification. For example, when acceptable alignment is achieved the device may beep. Alternatively, a visual indicator may be displayed when acceptable alignment is achieved. In some embodiments the device may automatically capture data when an acceptable alignment is detected. In other embodiments the user may issue a data capture instruction (for example by pressing a button, touch screen etc, or by any other suitable user input).

In other embodiments, the projected guide may be one or more portions of a previously captured image of the patient's skin surface. For example, it may be desirable to remove the wound 1 from the projected guide image, since the shape of the wound 1 may change over time, so that using the wound 1 in the guide image may confuse the user. Alternatively, the guide may comprise one or more guide masks or markings based on a previously captured image of the patient's skin surface. For example, guide markings may be generated based on the position of skin features 3, or the outline of a user's limb, or positions of bone features etc. In still further embodiments, one or more guide masks or markings may be selected from a library of available guide masks or markings (e.g. a lower leg mask may be used, having a shape corresponding to the average lower leg).

The projected guide may include image portions or markings corresponding to the anatomical fiducials 3. Anatomical fiducials may be selected by a user in the previous image for subsequent use in the guide image. In methods using projected guides, the absolute scale is again not necessarily known. The image data is obtained at approximately the same scale in each case because the user is guided to position the device to deliver images with approximately the same scale. If further accuracy is required, scaling or registration can be performed as discussed above.

The projected guide may be projected using any suitable auxiliary projector. Portable devices incorporating picoprojectors or any other suitable type of projector may also be used. In other embodiments the guide may be projected using the devices inbuilt flashlight. A suitable pattern mask may be added to the window of the flashlight in order to project a guide pattern.

Graphical overlays, conveying additional information such as the patient ID, wound type and location, and so on, may be added to any kind of projected guide pattern. Further guide markings may indicate the extent of the image frame or camera field of view.

In still further embodiments the device may be positioned at a desired range from the surface using a physical guide or frame that sets a distance between the surface and device. Such a physical guide may include a device support, and a spacing arrangement with one or more distal elements configured to contact the skin. In many embodiments skin contact is undesirable. However, in some settings the use of such a physical guide may be acceptable.

Where the device is capable of determining a range to the skin surface, by any of the methods disclosed herein or any other suitable method, this range information may be used in at least the following ways.

First, the range information allows data to be captured at an arbitrary range and the appropriate scale factor to be determined and applied to the measurements. Additionally, the range information may be used to crop and/or rescale photos captured at arbitrary ranges (on the same model smart device) or with different model smart devices to a standard field of view. This should lead to greater consistency in the display of images captured as part of a serial study.

Second, the range information may be used to guide the user to capture at a predetermined, 'standard', range. Again this leads to improved consistency (provided all captures are made using the same model smart device). A variation would be to guide the user to capture at the range which results in a standard field of view regardless of the camera model in the smart device, again for improved consistency.

In any embodiment described herein, the user device may be connected over any suitable wired or wireless connection to another local device and/or over a network to a server. The server may be a facility server (e.g. a hospital server) or may be a remote server used by a number of different facilities.

In some embodiments the capture and storage of data is controlled such that data is not stored, or is stored only transiently, on the device itself. Data is immediately communicated to secure storage over the wired/wireless link and/or over the network. A user may view data retrieved from that secure storage on the device display. The Applicant's methods at the device level may be implemented using a web application. The device may operate as a thin client.

In general, any of the data storage, communication and management methods and systems disclosed in the Applicant's co-pending U.S. patent application Ser. No. 15/144, 722 (the entire contents of which are hereby incorporated by reference) may be employed.

Further, any desired associated data may be captured, such as e.g. an audio/video recording of caregiver's observations, images of the patient, the wound outline(s), patient ID, condition, location data (e.g. GPS data) etc. Such data, and any data from auxiliary sensors, may be tagged to or associated with captured image data.

While automated methods of wound measurement may be provided, in some embodiments the user may be enabled to enter manually obtained measurements of wound dimensions (e.g. length, width).

Any of the assessment techniques described herein allow surface feature dimensions to be tracked over time, whether in arbitrary units or in absolute dimensions. These trends allow medical professionals to monitor surface feature development or healing. Where a measurement departs from the predicted trend (e.g. an average trend for similar wounds, or some other defined trend based on one or more of: wound size and/or other characteristics, tissue type, patient characteristics etc), an alert may be issued to a user, either through the device itself or by any suitable messaging system to a healthcare provider.

Statistical trends of conditions, treatments and outcomes can be monitored. This data can be used to suggest a particular treatment, based on a set of symptoms exhibited by a particular patient. Data can provide predictions for wound healing. Where actual healing differs from the prediction by more than a threshold, the system may issue an alert. Similarly, where the actual healing is in accordance with the predicted trend, a positive notification (e.g. "Wound healing well", or a green light or another positive indicator) may be issued or displayed.

In some embodiments it may be desirable to have substantially consistent scene field-of-view between image captures, despite the images being captured at different times and/or using different devices. This allows a series of images to have consistent apparent scale, allowing consistent visual scale appearance. To achieve this consistent scene size the image may be captured at a defined range (and/or zoom factor for devices incorporating a zoom lens), determined via the camera angular field-of-view. This can be achieved by several of the methods disclosed herein, including guiding the user with an image or guide overlay, guiding the user with a projected guide, and/or guiding the user to move the device closer or further to the surface until a desired range is achieved.

In any of the embodiments described herein it may be assumed that the surface feature and surrounding skin all lie in a plane. For many applications, this is expected to be sufficiently accurate. It may also be assumed that the device's optical axis or optical axes is/are perpendicular to that plane. Alternatively, in some embodiments no such assumption is made, and appropriate corrections may or may not be made.

The Applicant's methods and devices allow for assessment of skin features, especially skin features of human patients. The methods may rely on ubiquitous consumer electronics devices, such as smartphones or tablets, allowing assessment data to be obtained conveniently using relatively cheap and readily available devices. Data can be captured in an intuitive manner.

In some embodiments, executed within the facility, an auxiliary device or module (or "widget") including additional hardware may be used. In the case of auxiliary devices containing optical elements the alignment of the widget to the onboard camera within the capture device may be important. If the exact alignment of the auxiliary device to the host optical system cannot be guaranteed by design, it may be estimated or calibrated. The auxiliary device may communicate with the capture device using any appropriate wired, physical or wireless link.

The physical attachment of an auxiliary device to the capture device may be difficult due to the lack of mounting points available. However, an auxiliary device may be 'clipped on' to the capture device or built into a replacement case, or cover. The alignment of the auxiliary device to the capture device's optical system may be difficult to reproduce exactly between installations (especially where the auxiliary device is used with, or designed for use with, a multitude of device types). In such cases automatic alignment detection may be advantageous.

In one embodiment an auxiliary device may include a camera. In another embodiment an auxiliary device may include a camera and a range-finding device. This range finding device may be a direct range finder (ultrasonic, optical time-of-flight, microwave radar, etc), or a structured light or triangulation based device using one or more laser points or lines etc.

An auxiliary device including a camera may have a field-of-view overlapping that of the camera in the capture device. By imaging a scene with both the camera in the capture device and the auxiliary device simultaneously or in quick succession, the relative geometry of the cameras can be determined by comparing the two frames in conjunction with the intrinsic parameters of each camera and the position of common points in the scene. This provides improved accuracy over an auxiliary device including no camera, since it allows the geometry between the auxiliary device and the capture device to be determined.

The position of the points in common is given by the auxiliary range-finder subsystem and the cameras' intrinsic parameters. The extrinsic parameters of the two cameras can be determined by determining the alignment of the two camera frames.

Here, 'intrinsic' parameters refer to the known internal geometry of the camera, eg: lens focal length, lens focal distance, sensor pitch, geometric distortion, etc. In general the degrees per pixel (or the solid angle subtended by a pixel) will be known. However, because the range is unknown, the size of an area on an image object corresponding to a pixel on the sensor is not known.

'Extrinsic' parameters refer to the geometrical relationship between two components, for example the angle and offset of the laser plane relative to the camera's optical axis. The extrinsic parameters of the components within the auxiliary device can be determined to the required degree of accuracy either by design or by a calibration step in the factory prior to being supplied to the user of the smart device.

The camera within the auxiliary device may not be high resolution assuming there is sufficient scene overlap with the capture device camera. This allows on-the-fly calibration of the geometry between the auxiliary device and the capture device (ie: extrinsic parameters) by using an inexpensive low-res camera in the auxiliary device. The capture device's high resolution camera may be used for determining the 3D model and/or measurements as well as for producing the texture image.

In one embodiment an auxiliary device may include three line generating lasers surrounding a low-resolution camera connected to a low-power processor and battery subsystem. The auxiliary device may project a light pattern similar to that disclosed in the Applicant's U.S. Pat. No. 9,179,844.

Communications with the capture device may be provided by Bluetooth, or other wireless, or wired communication link.

Figure 15A:
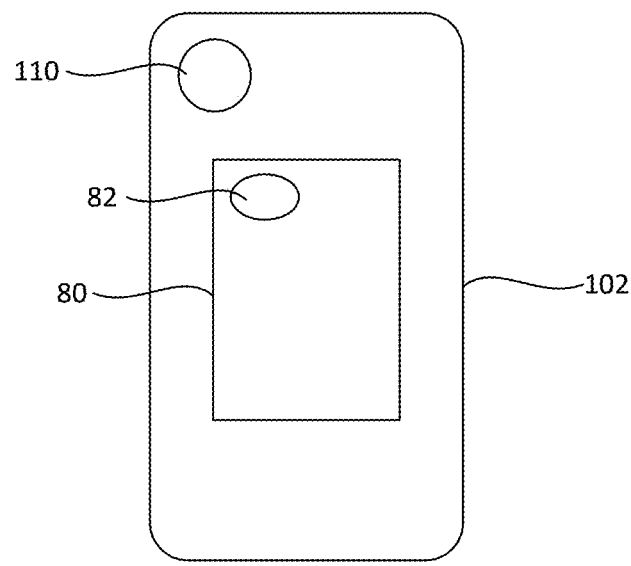
FIG. 15A shows an auxiliary range finding device mounted on a portable device.
Figure 15B:
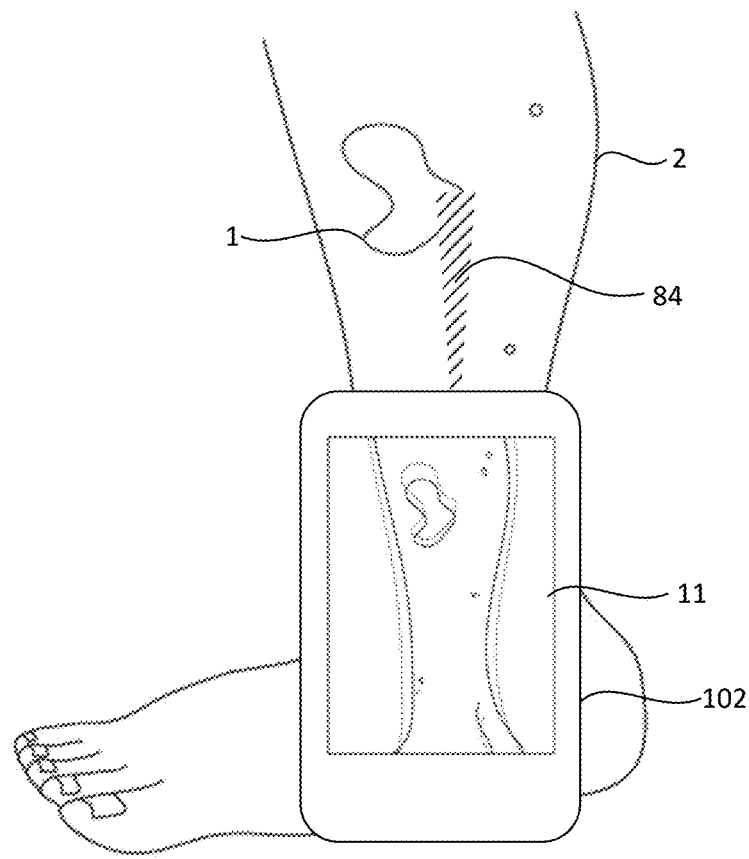
FIG. 15B shows the portable device and auxiliary range finding device of FIG. 15A relative to the leg of a patient.

As disclosed above, in some embodiments, an auxiliary device or widget can include a range finding device configured for attachment to a Smartphone, tablet, or other portable device that includes a camera. For example, FIGS. 15A and 15B illustrate an embodiment of such an auxiliary range finding device configured in accordance with embodiments of the present technology. In particular, FIG. 15A shows an auxiliary range finding device 80 ("auxiliary device 80") physically attached to a capture device 102 (e.g., a Smartphone or tablet) having an image sensor 110 (e.g., a camera). FIG. 15B shows the capture device 102 and auxiliary device 80 positioned relative to a leg 2 of a patient including a wound 1. The auxiliary device 80 can be attached to the capture device 102 using any suitable manner, including for example a partial sleeve that allows the auxiliary device 80 to mount to the capture device 102. Alternatively, the auxiliary device 80 may be integrated into a case of the capture device 102.

In some embodiments, as shown in FIG. 15A, the auxiliary device 80 can be attached to a "back side" of the capture device 102 that includes the image sensor 110. As shown in FIG. 15B, the capture device 102 can have a "front side" opposite the back side that includes a display 11 for viewing, e.g., images captured by the image sensor 110 of the capture device 102.

Referring to FIGS. 15A and 15B together, as described above, the auxiliary device 80 can be a time-of-flight-based device including range-finding components 82 for emitting and receiving optical, acoustic, radio, or other signals 84 (e.g., ultrasound, infrared light, visible light, microwave radar, etc.) to determine a time-of-flight measurement of the signals 84 between the auxiliary device 80 and the patient. The time-of-flight measurement can be processed to determine a range between the auxiliary device 80 (and the capture device 102) and the patient. In a particular embodiment, the signals 84 comprise infrared light. The auxiliary device 80 may be battery powered, or may be powered from an external power source. The auxiliary device 80 is further configured for communication with the capture device 102 using any suitable wired or wireless connection, including, e.g., Bluetooth.

In general, the auxiliary device 80 may be a very simple device for providing range information. The range information obtained by the auxiliary device 80 can be used to scale images. For example, the range information may be used to determine relative scale factors between images which can be useful to normalize images to a consistent scale. It may also be used simply to provide absolute dimensions from each image. Further, the range information may be used as a seed or an input to any suitable registration process, for registering images to each other. Thus, the range information may be used merely to determine scale, and a full model of a skin surface as provided by more complex range-finding cameras and devices may not be required.

In some embodiments, the auxiliary device 80 is used to determine a discrete or single range value as opposed to mapping a set of range values of the topography of the wound. For example, the auxiliary device 80 can determine a single measurement (e.g., a numerical value) for the range between the patient and device 102. For example, in certain embodiments, the range can be determined from a "first time-of-flight" measurement such that, e.g., the range corresponds to the closest patch of skin to the capture device 102. In other embodiments, the range can be a composite or average measurement over a region of the healthy skin and/or the wound. Moreover, as shown in FIG. 15B, the signals 84 emitted by the auxiliary device 80 may be incident upon only a portion of the skin surface of the leg 2 and/or the wound 1 of the patient, and may be incident upon more or less of the skin surface and the wound 1 depending on the distance between the auxiliary device 102 and the patient. Thus, depending on the method used to determine range, the range measurement may vary. For example, in the illustrated embodiment of FIG. 15B, a first time-of-flight measurement could correspond to the nearest patch of skin outside the wound 1 (for a concave wound), while an averaged value could produce a slightly greater range as the signals 84 are incident upon a portion of the wound 1 and a portion of the skin surface outside the wound 1.

Parameters of clinical significance in wound monitoring include the length, width, perimeter, and area of the boundary. In some embodiments, an auxiliary range finding device can project a tightly confined beam of visible light. In certain embodiments, the user is instructed to manipulate the resultant spot so that it lies just outside the boundary of the wound. The subsequently derived scale factor is optimal for making accurate and consistent boundary measurements. In some embodiments, the spot can be turned off during image capture using the capture device 102. In other embodiments, the spot can be turned on during at least one image capture and used for retrospective quality assurance of consistency of image captures made at different times and by different operators.

Moreover, as previously described, various embodiments of the technology disclosed herein may be combined with an auxiliary range finding device, such as the auxiliary device 80 illustrated in the embodiments of FIGS. 15A and 15B. For example, as described above with reference to FIGS. 4-4B, the display 11 of the capture device 102 can be configured to display a real-time camera view (shown in solid line) and an overlaid guide (shown in dashed line). The overlaid guide may simply be an overlaid image of the skin surface captured previously. The overlaid guide might include a reference to the previous position of the range finder spot (if a visible spot style range finder has been used). FIG. 15B shows that the camera view is misaligned with the guide, having a different perspective and scale, and therefore that the capture device 102 is not properly positioned. A user may align the capture device 102 with the desired position by moving it to bring the camera view into alignment with the guide. Thus, the image data from the image sensor 110 can be obtained at approximately the same scale in each image because the user is guided to position the capture device 102 to deliver images with approximately the same scale. If further accuracy is required, the auxiliary device 80 can be used to provide scaling or registration of the images so that, for example, the images can be processed to provide absolute dimensional information. That is, the auxiliary device 80 can provide calibration data in the form of range information so that images captured by the capture device 102 can be processed to provide absolute dimensional information or real scale information. This may be done, for example, in response to a health expert's determination that the surface feature requires further analysis.

Figure 16:
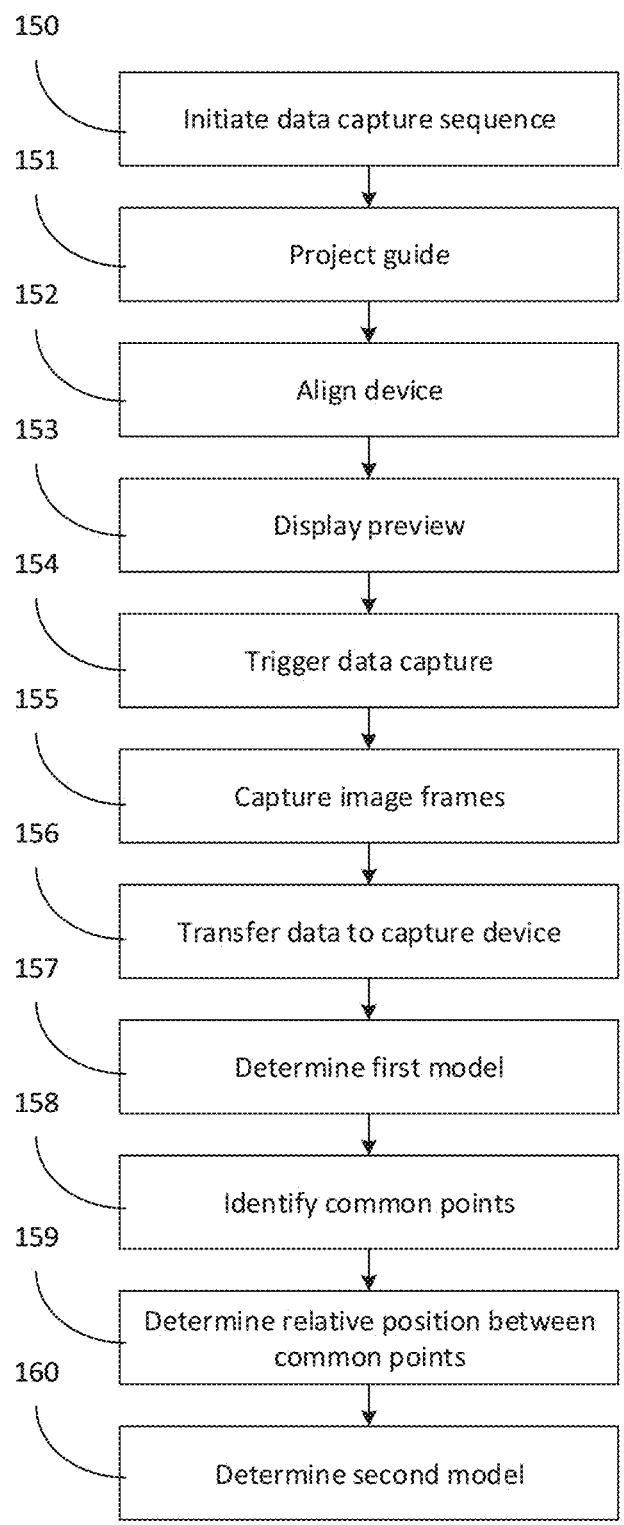
FIG. 16 is a flow chart showing one data capture sequence.

In one embodiment, executing within the facility, data may be captured in the following sequence, described with reference to FIG. 16. In other embodiments other capture sequences may be used, and the capture sequence may be adapted to the type of capture device and/or auxiliary device used.

At block 150 a user initiates the data capture sequence. At block 151 the guide may be projected. At block 152 the user aligns the capture device with the scene using the projected guide (e.g. bringing the capture device to a desired range and/or position and/or orientation). At block 153 a preview may be shown on the capture device's display, using image data from the capture device's camera. At block 154 a user may trigger capture, for example by pressing a button or touch screen on the capture device, or by any other suitable mechanism for issuing a capture instruction.

At block 155 one or more image frames may be captured. For example, using the capture device camera a high resolution image may be captured with the guide switched off. Using the auxiliary device camera a low resolution image may be captured with lasers on (possibly multiple frames to allow the laser beams to be uniquely identified in the captured images).

All data may be transferred from the auxiliary device to the capture device at block 156, for example via Bluetooth or some other wireless or wired communications link.

At block 157, a first model may be determined, based on the image data from the auxiliary device camera and the structured light information in those images.

At block 158, common points that are present in the images captured by both capture device camera and auxiliary camera may be identified.

At block 159 the relative position between common points may be determined using the first model.

At block 160 a second model may be determined based on the relative positions of common points and the host camera intrinsic parameters.

In another embodiment the auxiliary device camera may not be a visible light camera. For example, the auxiliary device camera may be a thermal camera. Such a device would require the scene to contain an object with common features apparent in both the thermal camera and optical camera images. Such a scene could be something like a user's hand with outstretched fingers placed on a desk. The outline of the warm hand on the desk could be detected by the thermal camera, and also in the capture device visible light camera.

Once the extrinsic parameters are known, the relative positions and orientations of the capture device camera and the auxiliary device camera can be determined and used in future data captures.

Figure 17:
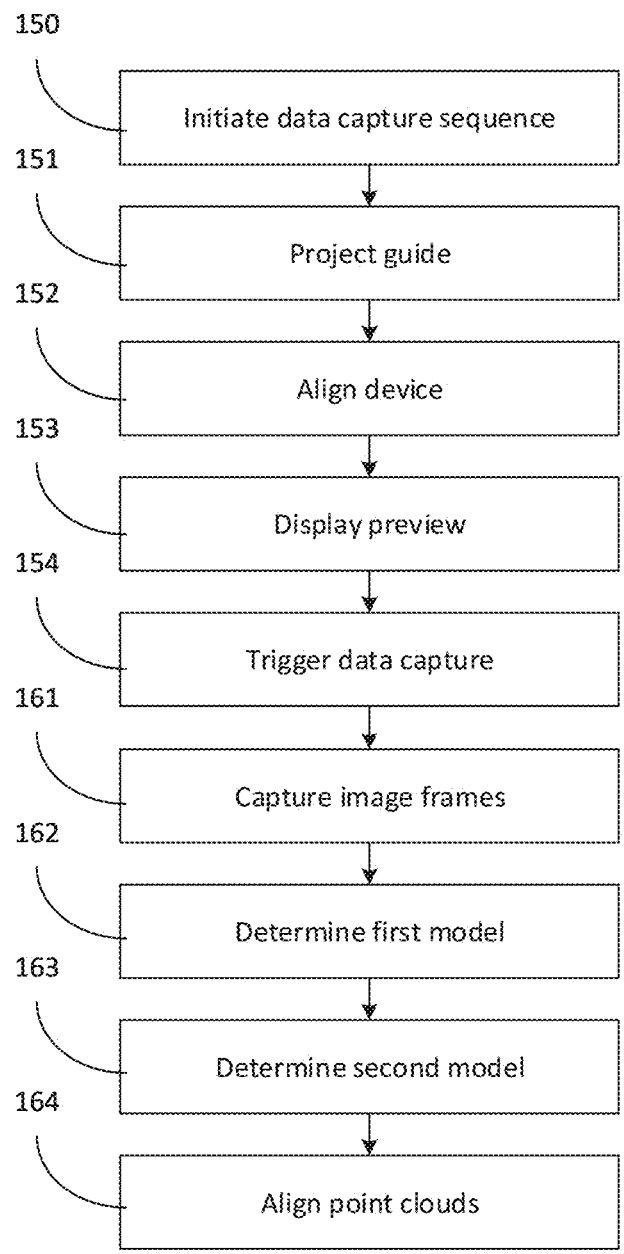
FIG. 17 is a flow chart showing a further data capture sequence.

FIG. 17 shows another embodiment, executing within the facility, in which blocks 150 to 154 are as described above with reference to FIG. 16. At block 161 one or more image frames may be captured. For example, using the capture device camera a high resolution image may be captured, and using the auxiliary device camera a low resolution image may be captured, both with lasers on (possibly multiple frames from each camera to allow the laser beams to be uniquely identified in the captured images). These images should be captured simultaneously or in sequence over a short time period. The image from both cameras will show the same positions of the lasers on the surface.

At block 162, a first model may be determined, based on the image data from the auxiliary device camera and the structured light information in those images.

At block 163 a second model may be determined, based on the image data from the capture device camera and the structured light information in those images. This second model will be inaccurate because its geometry (i.e. the position and/or orientation of the capture device camera relative to the auxiliary device lasers) is not known precisely. It is based on design (nominal) values. However, the first model is accurate because the geometry is fixed within the auxiliary device and the auxiliary device geometry is known or pre-calibrated.

At block 164 the second model point cloud may be aligned to the first model (accurate) point cloud, forming an accurate, hi-resolution model. That accurate, hi-resolution model may be registered with the hi-resolution image.

Alternatively, the extrinsic parameters may be determined based on the first model and the second model may be re-calculated based on triangulation of the laser images from the capture device camera.

Either of the procedures of FIG. 17 may be performed iteratively. They could also be assisted by feature recognition in the texture images.

In some embodiments the Applicant's methods may take advantage of existing device capabilities without the need for separate hardware attachments. In some embodiments the Applicant's methods may avoid any physical contact with the wound. In some embodiments the Applicant's methods may provide a mechanism for determining the scale of an image without requiring a reference object to be placed near the wound. In some embodiments the Applicant's methods may enable the determination of both area and depth or volume of a wound or dimensions of other anatomical surface features.

Where data from different devices (e.g. from one or more cameras and one or more sensors) or a plurality of sets of data from a single device (e.g. two or more images from a single camera) are required to be captured, all such data may be captured simultaneously or sequentially in response to a single capture instruction.

In some embodiments macro and/or wide angle images may be captured. Macro and/or wide angle images may be captured in addition to images at other ranges and/or focal lengths. One or more macro and/or wide angle images may be captured in addition to any number of images at other ranges and/or focal lengths, including any image or number of images according to any embodiment described above.

In some embodiments, a macro image may provide a more detailed view of a surface of an anatomical surface feature. For example, a macro image may provide a more detailed view and allow assessment of features or characteristics within a wound bed.

In some embodiments, a wide angle image may provide a broader view of a surface. For example, a wide angle image may provide a large field of view (encompassing an entire limb, or foot or torso, or even a whole body) to provide a context for where on the body the wound or wounds are.

Any of the guiding arrangements described above may be adapted to guide a user to position the device at a suitable range and/or position and/or orientation for capturing a macro image. In some embodiments the capture device may be arranged to guide the user to two or more desired ranges for capture of different images.

EXAMPLES

Several aspects of the present technology are set forth in the following examples:

1. A method of assessing a feature on a patient's skin surface including:
   i. receiving a first image of the patient's skin surface captured at a first time;
   ii. determining one or more dimensions of the feature at the first time, from the first image, in arbitrary units;
   iii. receiving a second image of the patient's skin surface captured at a second time;
   iv. identifying one or more anatomical features of the patient that are present in both the first and second images;
   v. determining a relative scale factor between the first and second images based on the identified anatomical features; and
   vi. determining one or more dimensions of the feature at the second time, from the second image and the relative scale factor, in the arbitrary units.

2. The method as claimed in example 1 wherein the first time precedes the second time.

3. The method as claimed in example 1 wherein the second time precedes the first time.

4. The method as claimed in any one of examples 1-3, further including performing a registration between the first and second images and wherein the relative scale factor is derived from that registration.

5. The method as claimed in any one of examples 1-4, including determining a trend of the one or more dimensions over time and displaying said trend to a user.

6. The method as claimed in example 5, including comparing said trend to a predicted trend and issuing a notification to a user if said trend departs from the predicted trend.

7. The method of claim any one of examples 1-6, including, subsequently, obtaining calibration data and determining the one or more dimensions at at least one of the first time and the second time, in absolute units.

8. The method as claimed in any one of examples 1-7, including displaying the determined dimensions.

9. The method as claimed in claim any one of examples 1-8, including storing the determined dimensions in memory.

10. The method as claimed in claim any one of examples 1-9, including:
   capturing the first image using a first capture device;
   by a first processor, determining the one or more dimensions of the feature at the first time;
   wherein the first processor is in one of: the first capture device; a personal computing device; and a server computer.

11. The method as claimed in example 10, including:
   capturing the second image using the first capture device or a second capture device;

by the first processor or a second processor determining one or more dimensions of the feature at the second time;
wherein the second processor is in one of: the second capture device; a personal computing device; and a server computer.

12. A method of assessing a feature on a patient's skin surface including:
i. receiving a first image of the patient's skin surface captured at a first time and calibration data associated with the first image;
ii. receiving a second image of the patient's skin surface captured at a second time;
iii. identifying one or more anatomical features of the patient that are present in both the first and second images;
iv. determining a relative scale factor between the first and second images based on the identified anatomical features; and
v. determining one or more dimensions of the feature at the second time, from the second image and the relative scale factor.

13. The method as claimed in example 12 wherein the first time precedes the second time.

14. The method as claimed in example 12 wherein the second time precedes the first time.

15. The method as claimed in any one of examples 12-14 wherein the calibration data includes one or more of:
a. data including an image, captured by a device capable of determining a scale associated with the image;
b. manually obtained measurement data;
c. data including an image, the image including a known-size fiducial.

16. The method as claimed in any one of examples 12-15, including determining a trend of the one or more dimensions over time and displaying said trend to a user.

17. The method as claimed in example 16, including comparing said trend to a predicted trend and issuing a notification to a user if said trend departs from the predicted trend.

18. The method as claimed in either example 16 or 17, including displaying the determined dimensions.

19. The method as claimed in in any one of examples 16-18, including storing the determined dimensions in memory.

20. The method as claimed in any one of examples 16-19, including:
capturing the first image using a first capture device;
by a first processor, determining one or more dimensions of the feature at the first time;
wherein the first processor is in one of: the first capture device; a personal computing device; and a server computer.

21. The method as claimed in example 20, including:
capturing the second image using the first capture device or a second capture device;
by the first processor or a second processor determining the one or more dimensions of the feature at the second time;
wherein the second processor is in one of: the second capture device; a personal computing device; and a server computer.

22. A method of assessing a feature on a patient's skin surface including:
i. displaying a guide image overlaid on a real-time camera view on a display of a capture device, the capture device including a camera, whereby a user may align the camera relative to the feature by moving the capture device to align the real-time camera view with the overlaid guide image; and
ii. capturing an image of the patient's skin surface using the camera.

23. A method as claimed in example 22, wherein the guide image includes one or more of:
a. a previously captured image of the patient's skin surface;
b. one or more portions of a previously captured image of the patient's skin surface;
c. one or more guide masks or markings based on a previously captured image of the patient's skin surface;
d. one or more guide masks or markings selected from a library of available guide masks or markings; and
e. one or more guide patterns that vary with range.

24. A method of assessing a feature on a patient's skin surface including:
i. at a first time, capturing a first image of the patient's skin surface;
ii. at a second time, projecting a guide image onto the patient's skin surface using a projector, the projector being coupled to or incorporated in a capture device including a camera, the guide image including one or more of:
a. all of the first image, or one or more portions of the first image; and
b. one or more markings based on the first image;
whereby a user may align the camera to a position and field of view corresponding to the first image by moving the capture device to align the projected guide with the anatomy of the patient; and
iii. capturing an image of the patient's skin surface using the camera.

25. A method of assessing a feature on a patient's skin surface including:
i. using a capture device including an autofocus camera, capturing an image of the patient's skin surface;
ii. retrieving focal data from the camera;
iii. determining a scale associated with the captured image based on the retrieved focal data;
iv. determining one or more dimensions of the feature based on the image and the determined scale.

26. A method as claimed in example 25, wherein the retrieving focal data from the camera includes:
a) driving the camera through a range of focal distances;
b) capturing a plurality of calibration images at different focal distances within the range;
c) determining a focal metric for each calibration image;
d) fitting a curve through the focal metrics; and
e) determining a focal distance value for a point of peak focal quality.

27. A method as claimed in either example 25 or 26, further including determining a temperature and applying a correction based on the determined temperature to the focal data.

28. The method as claimed in any one of examples 25-27, including
a. at a different time, using the same or a different capture device including an autofocus camera, capturing a further image of the patient's skin surface;
b. retrieving further focal data from the camera;
c. determining a further scale associated with the captured further image based on the retrieved further focal data;
d. determining one or more dimensions of the feature at the different time, based on the further image and the determined further scale; and e. determining a trend of the one or more dimensions over time and displaying said trend to a user.

29. The method as claimed in example 28, including comparing said trend to a predicted trend and issuing a notification to a user if said trend departs from the predicted trend.

30. The method as claimed in any one of examples 25-29, including displaying the determined dimensions.

31. The method as claimed in any one of examples 25-30, including storing the determined dimensions in memory.

32. method as claimed in claim in any one of examples 25-32, including:
by a first processor, determining the one or more dimensions of the feature;
wherein the processor is in one of: the capture device; a personal computing device; and a server computer.

33. A method of assessing a feature on a patient's skin surface including:
i. capturing an image of the patient's skin surface using a capture device including a first camera and an auxiliary camera;
ii. based on a common image region covered by both the first camera and the auxiliary camera and a known baseline between an optical axis of the first camera optical axis and an optical axis of the second camera, determining a range to the patient's skin surface; and
iii. from the range determining a scale associated with the image.

34. A method as claimed in example 33 wherein the auxiliary camera has a different focal length to the first camera.

35. A method as claimed in either example 33 or 34 wherein the auxiliary camera has a different spectral response than the first camera.

36. A method of assessing a feature on a patient's skin surface including:
i. using a capture device including a camera, capturing at least a first image of the patient's skin surface from a first position of the capture device and a second image of the patient's skin surface from a second position of the capture device;
ii. determining at least a distance between the first position and the second position;
iii. based on a common image region present in the first and second images and the determined distance, determining a range to the patient's skin surface; and
iv. from the range determining a scale associated with the image.

37. A method as claimed in example 36, wherein determining at least the distance is performed by an inertial measurement unit.

CONCLUSION

While the present technology has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the present technology in its broader aspects is not limited to the specific details, representative apparatus and method, and illustrative examples shown and described. Accordingly, departures may be made from such details without departure from the spirit or scope of the Applicant's general inventive concept.

We claim:

1. A method of assessing a feature on a patient's skin surface, comprising:
capturing an image of the patient's skin surface with a camera of a portable capture device;
capturing time-of-flight range information for an area of the patient's skin surface with an auxiliary time-of-flight range measurement device separate from the portable capturing device, wherein the range information includes a set of multiple range values corresponding to different portions of the area of the patient's skin surface, and wherein the auxiliary time-of-flight range measurement device is attached to the portable capture device;
determining a single range value between the capture device and the patient's skin surface based on the range information;
determining a scale associated with the image from the single range value; and
determining one or more dimensions of the feature on the patient's skin surface based on the image and the determined scale.

2. The method of claim 1 wherein capturing the range information comprises projecting light onto the area of the patient's skin surface, wherein the area of the patient's skin surface includes at least a portion of the feature and another portion of the patient's skin surface, and wherein the single range value is determined for only the other portion of the patient's skin surface.

3. The method of claim 2 wherein the single range value is a range value in the set of range values corresponding to a first time-of-flight measurement of the projected light.

4. The method of claim 1 wherein capturing the range information comprises projecting light onto the area of the patient's skin surface, and wherein the area of the patient's skin surface includes only a portion of the patient's skin surface apart from the feature.

5. The method of claim 1 wherein capturing the range information comprises projecting light onto the area of the patient's skin surface, wherein the area of the patient's skin surface includes a portion of the feature and another portion of the patient's skin surface, and wherein the single range value is based on an average of the set of range values corresponding to an average time-of-flight value of the projected light.

6. The method of claim 1, further comprising, before capturing the image of the patient's skin surface:
displaying a guide image overlaid on a real-time camera view on a display of the portable capture device; and
aligning the camera of the capture device relative to the feature on the patient's skin surface by moving the portable capture device to align the real-time camera view with the overlaid guide image.

7. The method of claim 6 wherein the guide image includes at least one of:
(a) a previously captured image of the patient's skin surface;
(b) one or more portions of a previously captured image of the patient's skin surface;
(c) one or more guide masks or markings based on a previously captured image of the patient's skin surface;
(d) one or more guide masks or markings selected from a library of available guide masks or markings; and
(e) one or more guide patterns that vary with range.

8. The method of claim 1 wherein the range value is a single absolute numerical value.

9. The method of claim 1 wherein the auxiliary range measurement device is releasably attached to an outer surface of the portable capture device.

10. The method of claim 1 wherein the range information includes time-of-flight measurements of an optical, acoustic, or radio signal emitted from and received by the auxiliary range measurement device.

11. The method of claim 1 wherein the range information includes time-of-flight measurements of an infrared signal emitted from and received by the auxiliary range measurement device.

12. The method of claim 1, further comprising wirelessly transmitting the range information from the auxiliary range measurement device to the portable capture device.

13. The method of claim 12 wherein transmitting the range information includes sending the range information from the auxiliary range measurement device to the portable capture device via a Bluetooth connection.

14. The method of claim 1 wherein the dimensions include at least one of a linear dimension, a perimeter, and an area of the feature.

15. The method of claim 1 wherein the portable capture device is a smartphone or tablet.

16. A system for assessing a feature on a skin surface comprising:
 a handheld portable computing device having a processor, a display, a camera, and a wireless data receiver; and
 an auxiliary device separate from the portable computing device and attached to the portable computing device, the auxiliary device having a light emitter configured to illuminate an area of the skin surface, a light sensor, a time-of-flight calculator configured to calculate time-of-flight measurements of light from the light emitter to the light sensor, wherein the time-of-flight measurements correspond to a set of multiple range values for different portions of the area of the skin surface, and a wireless data transmitter configured to transmit time-of-flight data to the wireless data receiver of the handheld portable computing device;
 wherein the processor is configured to determine—
  a single range value corresponding to a distance from the portable computing device to the skin surface based on the time-of-flight measurements; and
  at least one of a length, an area, and a circumference of the feature based at least in part on an image received from the camera and the single range value.

17. The system of claim 16 wherein the display is on a front side of the handheld portable computing device, wherein the camera is on a back side of the handheld portable computing device, and wherein the auxiliary device is configured to be attached to the back side.

18. The system of claim 16 wherein the handheld portable computing device further includes a wireless transmitter configured to transmit control signals to the auxiliary device.

19. A method of assessing a feature on a patient's skin surface, the method comprising:
 capturing an image of the patient's skin surface with a camera of a portable capture device, wherein the portable capture device is a smartphone or tablet having a front side and a back side opposite the front side, wherein the camera is positioned at a first portion of the backside of the portable capture device, and wherein the front side includes a display configured to display the image of the patient's skin surface;
 capturing time-of-flight range information for an area of the patient's skin surface with an auxiliary time-of-flight range measurement device separate from the portable capture device, wherein the range information includes a set of multiple range values corresponding to different portions of the area of the patient's skin surface, and wherein the auxiliary time-of-flight range measurement device is releasably attached to a second portion of the backside of the portable capture device different than the first portion;
 determining a single range value between the capture device and the patient's skin surface based on the range information;
 determining a scale associated with the image from the single range value; and
 determining one or more dimensions of the feature on the patient's skin surface based on the image and the determined scale.

* * * * *